United States Patent
Eggan et al.

(10) Patent No.: US 9,180,114 B2
(45) Date of Patent: *Nov. 10, 2015

(54) NEURODEGENERATIVE DISEASES AND METHODS OF MODELING

(75) Inventors: Kevin Eggan, Boston, MA (US); Francesco Paolo DiGiorgio, Barletta (IT)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 708 days.

This patent is subject to a terminal disclaimer.

(21) Appl. No.: 12/570,476

(22) Filed: Sep. 30, 2009

(65) Prior Publication Data

US 2010/0130574 A1    May 27, 2010

Related U.S. Application Data

(60) Provisional application No. 61/200,293, filed on Nov. 26, 2008.

(51) Int. Cl.
- *A61K 31/403* (2006.01)
- *A61K 31/40* (2006.01)
- *A61K 31/4164* (2006.01)
- *A61K 31/7052* (2006.01)

(52) U.S. Cl.
CPC ............... *A61K 31/40* (2013.01); *A61K 31/403* (2013.01); *A61K 31/4164* (2013.01); *A61K 31/7052* (2013.01)

(58) Field of Classification Search
CPC . A61K 31/403; A61K 31/40; A61K 31/4164; A61K 31/7052
See application file for complete search history.

(56) References Cited

U.S. PATENT DOCUMENTS

2005/0165033 A1* 7/2005 Baxter et al. ............... 514/266.2

FOREIGN PATENT DOCUMENTS

| WO | WO 03/062200 A2 * | 7/2003 |
| WO | WO 2006/092579 | 9/2006 |
| WO | WO 2006/095183 | 9/2006 |

OTHER PUBLICATIONS

Sargsyan et al. 2005, "Microglia as Potential contributors to motor neuron injury in amyotrophic lateral sclerosis." Glia, vol. 51, pp. 241-253.*
DiGiorgio, F.P. et al., Cell Stem Cell, 3:637-648 (2008). "Human Embryonic Stem Cell-Derived Motor Neurons Are Sensitive to the Toxic Effect of Glial Cells Carrying an ALS-Causing Mutation."
Liang, X. et al., J. Neurochem., 92:477-486 (2005). Prostaglandin D2 mediates neuronal protection via the DP1 receptor.
Saleem, S. et al., Eur. J. Neurosci., 26(1):73-78 (2007). "PGD2 DP1 receptor protects brain from ischemia-reperfusion injury."
Wu, L. et al., Neurosci. Lett., 421(3):253-258 (2007). "Divergent effects of prostaglandin receptor signaling on neuronal survival."
Acsadi, et al., "Increased Survival and Function of SOD1 Mice After Glial Cell-Derived Neurotropic Factor Gene Therapy", Human Gene Therapy 13: 1047-1059 (2002).
Epstein, et al., "Transgenic mice with increased Cu/Zn-superoxide dismutase activity: Animal model of dosage effects in Down syndrome", Proc. Natl. Acad. Sci 84:8044-8048 (1987).
Gurney et al., "Motor Neuron Degeneration in Mice That Express a Human Cu,Zn Superoxide Dismutase Mutation", Science 264:1772-1775 (1994).
Kostic, et al., "Bcl-2: Prolonging Life in a Transgenic Mouse Model of Familial Amyotrophic Lateral Sclerosis", Science 277: 559-562 (1997).
Matzuk, et al., "Ovarian Function in Superoxide Dismutase 1 and 2 Knockout Mice", Endocrinology 139(9): 4008-4011 (1998).
MGI website for SOD1 phenotype analysis, 2013 http://www.informatics.jax.org/searches/allele_report.cgi?_Marker_key=13516 date accessed Sep. 30, 2013.
Reaume, et al., "Motor neurons in Cu/Zn superoxide dismutase-deficient mice develop normally but exhibit enhanced cell death after axonal injury", Nature Genetics 13: 43-47 (1996).
Non-Final Office Action for U.S. Appl. No. 13/750,452, dated Oct. 3, 2013.
Phillips, A., "The challenge of gene therapy and DNA delivery," J Pharm Pharmacology, 53: 1169-1174 (2001).
Vidal et al., "Making sense of antisense," European Journal of Cancer, 41: 28122818 (2005).
Pirollo et al., " Targeted Delivery of Small Interfering RNA: Approaching Effective Cancer Therapies," Cancer Res.; 68(5): 1247-1250 (2008).
Winkler, "Oligonucleotide conjugates for therapeutic applications," Ther. Deliv.; 4: 791-809 (2013).
Van Hecken et al., " the effect of MK-0524, a prostaglandin D2 receptor antagonist, on prostaglandin D2-induced nasal airway obstruction in healthy volunteers," Eur J Clin Pharmacal, 2007; 63: 135-141.
Drachman et al., "Cyclooxygenase 2 Inhibition Protects Motor Neurons and Prolongs Survival in a Transgenic Mouse Model of ALS," Ann Neurol; 52: 771-778 (2002).
Sturino et al., "Discovery of a Potent and Selective Prostaglandin $D_2$ Receptor Antagonist, [(3R)-4-(4uChlorobenzyl)-7 — fluoro-5-(methylsulfonyl)- 1,2,3,4utetrahydrocydopenta[b ]indo1-3-- yl]-acetic Acid (Mk-0524)," J. Med. Chem., 50:794806, (2007).
Liang, et al., "Function of COX-2 and Prostaglandins in Neurological Disease," J Mol Neurosci,; 33: 94-99 (2007).
Non-Final Office Action for U.S. Appl. No. 14/244,554, mailed Aug. 12, 2015.

* cited by examiner

*Primary Examiner* — Kara R McMillian
(74) *Attorney, Agent, or Firm* — Lisa M. Warren, Esq.; Morse, Barnes-Brown & Pendleton, P.C.

(57) ABSTRACT

This invention relates to methods for neuroprotection, promoting survival of motor neurons and the treatment of motor neuron diseases by preventing cell signaling through the classic prostaglandin D2 receptor DP1.

10 Claims, 23 Drawing Sheets

| | SOD1 G93A Glia Days in Culture | | | |
|---|---|---|---|---|
| | 7 | 14 | 21 | 28 |
| GFAP | ++++ (98.6%) | ++++ (92.2%) | ++++ (85%) | ++ (61%) |
| S100 | ++++ (100%) | ++++ (100%) | ++++ (100%) | ++++ (100%) |
| RC2 | + (14.2%) | + (9.5%) | + (8.7%) | + (8.4) |
| Vimentin | - (0%) | - (0%) | - (0%) | - (0%) |
| CD 11b | +/- (2.7%) | +/- (3.1%) | +/- (2.9%) | +/- (2.8%) |
| CNPase | +/- (2.2%) | +/- (2.4%) | +/- (2.5%) | +/- (2.1%) |

*FIG. 7* b  Subset of genes overexpressed exclusively in SOD1G93A glia

| Gene Symbol | Fold diff. G93A vs WT | Gene Description |
|---|---|---|
| Ptgdr | 14.125 | Prostaglandin D receptor |
| Gmfb | 13.07692308 | Glia maturation factor, beta |
| Ccl8 (Mcp2) | 2.776623377 | Chemokine (C-C motif) ligand 8 |
| Shh | 2.475247525 | Sonic Hedgehog |
| Cxcl7 | 2.43324937 | Pro-platelet basic protein (Ppbp) |
| Ccl5 (Rantes) | 2.295539171 | Chemokine (C-C motif) ligand 5 |

*FIG. 14 continued*

SEQUENCE LISTING

<160> NUMBER OF SEQ ID NOS: 12

<210> SEQ ID NO 1

<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
catcagccct aatccatctg a          21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
cgcgactaac aatcaaagtg a          21

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
ctaggccaca gaattgaaag atct          24

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
catcagccct aatccatctg a          21

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
aagttcatct gcaacacc          18

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
tccttgaaga agatggtgcg          20

<210> SEQ ID NO 7
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 7
acaggaccuc ugaagaagct t                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 8
auaugaccag gucaggcagt t                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 9
gggugucagu aggaaucaat t                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 10
ccagugugug acucacugut t                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 11
agcccaccca ggacuuagct t                                              21

<210> SEQ ID NO 12
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 12
acgcagcugc aacugaagct t                                              21
```

NEURODEGENERATIVE DISEASES AND METHODS OF MODELING

RELATED APPLICATIONS

This application claims the benefit under 35 U.S.C. §119 (e) of U.S. Provisional Application No. 61/200,293, filed Nov. 26, 2008. The entire contents of which is hereby incorporated by reference.

GOVERNMENT SUPPORT

This invention was made with Government support under RO1 HD046732-01A1 awarded by the National Institutes of Health. The Government has certain rights in the invention.

BACKGROUND

Amyotrophic Lateral Sclerosis ("ALS"), also known as Lou Gehrig's disease, is a progressive neurodegenerative disease characterized by the loss of upper and lower motor neurons, culminating in muscle wasting and death from respiratory failure (Boillee, S., Vande Velde, C. & Cleveland, D. W. ALS: a disease of motor neurons and their nonneuronal neighbors. Neuron 52, 39-59, 2006). The majority of ALS cases are apparently sporadic, with 90% of patients presenting disease symptoms without a family history of ALS. The remaining 10% of ALS patients are diagnosed with familial ALS (Boillee et al., 1996; Brown, R. H., Jr. Amyotrophic lateral sclerosis. Insights from genetics. Arch Neurol 54, 1246-50, 1997; Cole, N. & Siddique, T. Genetic disorders of motor neurons. Semin Neurol 19, 407-18, 1999). Approximately 25% of the familial cases of ALS are caused by dominant mutations in the gene encoding super oxide dismutase (SOD1) (Rosen, D. R. et al. Mutations in Cu/Zn superoxide dismutase gene are associated with familial amyotrophic lateral sclerosis. Nature 362, 59-62, 1993). Identification of pathogenic alleles of SOD1 has led to the production of transgenic mouse and rat models for the study of ALS (Gurney, M. E. et al. Motor neuron degeneration in mice that express a human Cu, Zn superoxide dismutase mutation. Science 264, 1772-5, 1994; Nagai, M. et al. Rats expressing human cytosolic copper-zinc superoxide dismutase transgenes with amyotrophic lateral sclerosis: associated mutations develop motor neuron disease. J. Neurosci. 21, 9246-54, 2001; Bruijn, L. I. et al. ALS-linked SOD1 mutant G85R mediates damage to astrocytes and promotes rapidly progressive disease with SOD1-containing inclusions. Neuron 18, 327-38, 1997; Wong, P. C. et al. An adverse property of a familial ALS-linked SOD1 mutation causes motor neuron disease characterized by vacuolar degeneration of mitochondria. Neuron 14, 1105-16, 1995). Overproduction of pathogenic human SOD1 protein in mice and rats leads to late onset, progressive neurodegenerative disease (Gurney et al., 1994; Bruijn et al., 1997; Wong et al., 1995). Studies of the SOD1 animal models have led to the identification and study of intrinsic pathogenic characteristics of ALS motor neurons including the formation of protein aggregates, cytoskeletal abnormalities, proteosome dysfunction and increased sensitivity to cell death signals (Boillee et al., 2006; Bruijn, L. I., Miller, T. M. & Cleveland, D. W. Unraveling the mechanisms involved in motor neuron degeneration in ALS. Annu Rev Neurosci 27, 723-49, 2004).

Studies of chimeric mice suggest that non-cell autonomous processes contribute to motor neuron death in ALS (Clement, A. M. et al. Wild-type nonneuronal cells extend survival of SOD1 mutant motor neurons in ALS mice. Science 302, 113-7, 2003). In animals bearing both wild-type cells and cells harboring the SOD1G93A transgene, wild-type neurons surrounded by transgenic non-neuronal cells acquired cellular phenotypes characteristic of ALS (Clement et al., 2003). Conversely, transgenic neurons associated with wild-type non-neuronal cells were increasingly spared. However, these animal studies did not identify which cells were involved in the pathological interactions with motor neurons due to the complex cellular milieu of both the spinal chord and the muscle. Conditional mutagenesis experiments in which the SOD1 transgene was specifically removed from motor neurons and microglial cells led to an increase in animal lifespan, again suggesting the SOD1 protein can have both cell autonomous and non-cell autonomous affects in the disease (Boillee, S. et al. Onset and progression in inherited ALS determined by motor neurons and microglia. Science 312, 1389-92, 2006). However, these experiments could not address the direct effect of cellular interactions with motor neurons in the disease because of the use of death as an endpoint.

BRIEF SUMMARY OF THE INVENTION

This invention relates to methods for neuroprotection, promoting survival of motor neurons and the treatment of motor neuron diseases by preventing cell signaling through the classic prostaglandin D2 receptor DP1.

Embodiments of the present invention provide methods of treating motor neuron disease (MND), the methods comprise administering an inhibitor of a prostaglandin D2 DP1 receptor (also known as AS1, ASRT1, DP, DP1, MGC49004) to a subject in need thereof, wherein the inhibitor inhibits expression or activity the prostaglandin D2 DP1 receptor.

The inhibitor of a prostaglandin D2 DP1 receptor is selected from the group consisting of: a small molecule, a nucleic acid molecule, a protein e.g. an activity-blocking antibody or a peptidominetic, and combinations thereof. For example, a small molecule can be a DP1 receptor specific antagonist; a nucleic acid can be a RNA interference molecule that inhibits the expression of the PTGDR gene; and an anti-DP1 receptor specific antibody can be an antibody or fragment thereof that blocks the receptor-ligand binding, the ligand being prostaglandin.

In one embodiment, the inhibitor is selected from a group consisting of an anti-DP1 antibody, an anti-PGD2 antibody, a DP1 specific RNA interfering agent, MK-0524, BWA868C, ONO-4127Na and resveritrol. Combinations of these inhibitors can be administered to the subject. A combination of routes of administration is also contemplated.

In one embodiment, the inhibitor is administered with therapeutics typically used for the treatment of MND, e.g. riluzole.

In one embodiment of the methods described herein further comprising selecting a subject diagnosed with motor neuron disease. The subject is a mammal having motor neurons, e,g. humans, dogs, cats etc.

In some embodiments, the motor neuron disease includes but is not limited to amyotrophic lateral sclerosis (ALS), primary lateral sclerosis (PLS), progressive muscular atrophy (PMA), pseudobulbar palsy, progressive bulbar palsy, spinal muscular atrophy (SMA) and post-polio syndrome.

In one embodiment, the motor neuron disease is associated with a SOD1 mutation in at least one allele.

BRIEF DESCRIPTION OF THE DRAWING

(FIG. 1A) for human SOD1 and Il2, and (FIG. 1B) for GFP in Hb9::GFP, Hb9::GFP; SOD1 and Hb9GFP; SOD1G93A ES cell lines.

(FIG. 2C) Number of GFP positive motor neurons derived from Hb9GFP and SOD1G93A 15 and 30 days after EB dissociation plated at the concentration of $8 \times 10^5$ (C) and $4 \times 10^5$ (E) per well. (FIGS. 2D, 2F). Same experiments in (FIGS. 2C, 2D) analyzed as percent of GFP positive motor neurons derived from Hb9GFP and SOD1G93A cell lines present at day 15, which still remain at 30 days.

(FIG. 5A) Non transgenic cell line, (FIG. 5B) Hb9GFP, (FIG. 5C) Hb9GFP; SOD1, (FIG. 5D) Hb9GFP; SOD1G93A. The dot plots are representative of one experiment, but the percentages are the average of three different experiments. Calcein blue was used to assay the viability of cells during sorting.

(FIG. 6A) Average area of SOD1 inclusions in SOD1 and SOD1G93A derived motor neurons. (FIG. 6B) Average length of SOD1 inclusions in SOD1 and SOD1G93A derived motor neurons. (FIG. 6C) Integrated Optical Density of SOD1 inclusions in SOD1 and SOD1G93A derived motor neurons. (FIG. 6D) Distribution of inclusion bodies per cell in SOD1 and SOD1G93A derived motor neurons. Results are graphed as mean+/−S.E.M.

(FIGS. 7A, 7B) Summary of immuno-fluorescent analysis of glia markers GFAP, S100, RC2, Vimentin, CD 11b, CNPase for both wt glia (FIG. 7A) and SOD1G93A glia (FIG. 7B) at different time points.

(FIG. 8A) Diagram outlining the protocol used to differentiate human ES cells into motor neurons: Undifferentiated human ES cell colonies are dissociated in collagenase, and grown as EBs for the first 14 days in EB media, then are induced to a rostrocaudal identity with retinoic acid (RA) and Shh for another 14 days. Finally, EBs are matured in the presence of GDNF for 14 more days. At this point the EBs can either be plated whole or dissociated with papain and then plated. (FIG. 8B) Percentage of cells immuno-reactive for HB9 after treatment with or without RA and Shh. (FIG. 8C) Percentage of cells immuno-reactive for HB9 after 42 days of differentiation in different HuES cell lines.

(FIG. 10A) Experimental design: embryonic stem cells were differentiated into motor neurons, and an equal number of cells were plated on two different glial monolayers; one derived from mice over-expressing SOD1G93A, and the other derived from non-transgenic mice (WT). Motor neurons were counted after 10 and 20 days in co-culture. (FIG. 10B) Number of HB9 positive cells 10 days after plating on SOD1G93A or non-transgenic (WT) glia. (FIG. 10C) Number of HB9 positive cells 20 days after plating on SOD1G93A or non-transgenic (WT) glia. (FIG. 10D) Number of Hb9::GFP cells 20 days after plating on SOD1G93A glia or non-transgenic (WT) glia or glia over-expressing the wild type form of human SOD1 (SOD1WT).

(FIG. 11A) Experimental design: embryonic stem cells were differentiated into motor neurons, and an equal number of cells were plated on two different glial monolayers; one derived from mice over-expressing the mutation SOD1G93A, and the other derived from non-transgenic mice (WT). Human ES cell derived interneurons were counted after 20 days in co-culture using two different markers, CHX10 and LHX2. (FIG. 11B) Number of LHX2 positive cells 20 days after plating on SOD1G93A glia or non-transgenic (WT) glia. (FIG. 11C) Number of CHX10 positive cells 20 days after plating on SOD1G93A or non-transgenic (WT) glia. (FIG. 11D) Experimental design: embryonic stem cells were differentiated into motor neurons and same number of cells was plated on two different MEF monolayers; one derived from mice over-expressing the mutation SOD1G93A, and the other derived from non-transgenic mice (WT). (FIG. 11E) Motor neurons were counted after 20 days to compare the two conditions.

(FIG. 12A) Percent of sectioned EBs (n=20) staining positive for PAX6, NKX6.1, ISL1/2, or HB9 at day 0, day 14, day 28, and day 42 of differentiation. (FIG. 12B) Percent of cells per sectioned EB (n=3) staining positive for PAX6, NKX6.1, ISL1/2, or HB9 at day 0, day 14, day 28, and day 42 of differentiation.

DESCRIPTION OF CERTAIN EMBODIMENTS OF THE INVENTION

Figure 1:
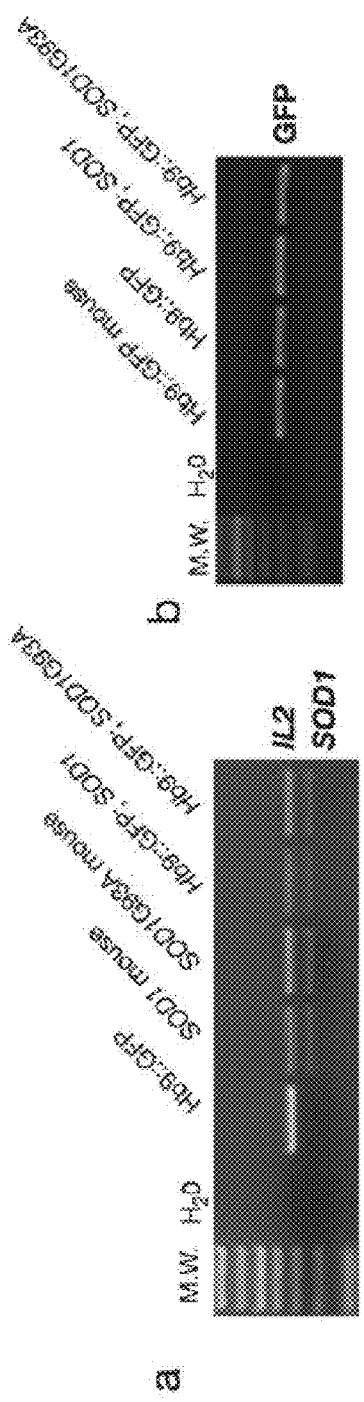
FIG. 1 shows one embodiment of derivation of Hb9GFP; SOD1 mouse ES cell lines. PCRs.

Embodiments of the present invention provide methods of treating motor neuron disease (MND), the methods comprise administering an inhibitor of a prostaglandin D2 DP1 receptor (also known as AS1, ASRT1, DP, DP1, MGC49004) to a subject in need thereof, wherein the inhibitor inhibits expression or activity the prostaglandin D2 DP1 receptor.

The inventors demonstrated that the inhibitor of Prostaglandin D2 receptor (MK 0524) and BW868C significantly reduced neuronal cell death for motor neurons cultured on SOD1G93A glia.

In some embodiments, the inhibitor of a prostaglandin D2 DP1 receptor is selected from the group consisting of: a small molecule, a nucleic acid molecule, a protein, e.g. an activity-blocking antibody or a peptidomimetic, and combinations thereof. For example, a small molecule can be a DP1 receptor antagonist; a nucleic acid can be a RNA interference molecule that inhibits the expression of the PTGDR gene; an anti-DP1 antibody can be an antibody that blocks the receptor-ligand binding.

In one embodiment, the inhibitor is:

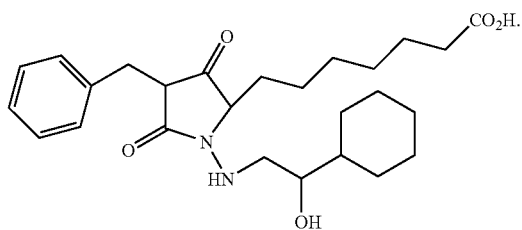 [SMILES: O=C(O)CCCCCCC1C(=O)C(Cc2ccccc2)C(=O)N1NCC(O)C1CCCCC1]

In another embodiment, the inhibitor is:

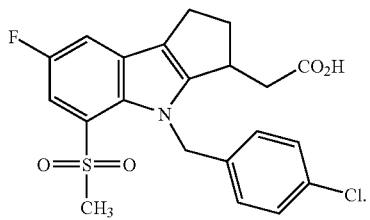 [SMILES: CS(=O)(=O)c1cc(F)cc2c3c(n(Cc4ccc(Cl)cc4)c12)C(CC(=O)O)CC3]

In another embodiment, the inhibitor is:

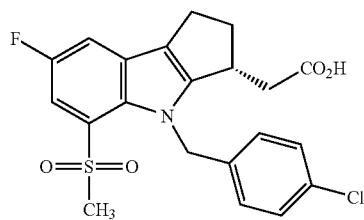 [SMILES: CS(=O)(=O)c1cc(F)cc2c3c(n(Cc4ccc(Cl)cc4)c12)[C@@H](CC(=O)O)CC3]

In one embodiment, the inhibitor is selected from a group consisting of an anti-DP1 antibody, an anti-PGD2 antibody, a DP1 specific RNA interfering agent, DP1 antagonist such as MK-0524, BWA868C, ONO-4127Na and resveritrol. Combinations of these inhibitors can be administered to the subject. A combination of routes of administration is also contemplated.

The present invention also provides a method for treating motor neuron disease (MND) comprising administering the compound of formula (I):

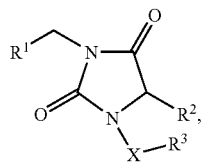

Formula (I)

wherein $R^1$ is cycloalkyl, heterocycloalkyl, aryl, or heteroaryl, each of which can be optionally substituted;

$R^2$ is H, halo, alkyl, alkenyl or alkynyl, each of which can be optionally substituted;

$R^3$ is H, alkyl, alkenyl, alkynyl, cycloalkyl, heterocycloalkyl, aryl, or heteroaryl, each of which can be optionally substituted; and X is NH, C(O) or $CH_2$.

In some embodiments, X is NH.

In some embodiments, $R^1$ is an aryl or heteroaryl. In some embodiments, $R^1$ is a bicyclic aryl or heteroaryl. In some embodiments, $R^1$ is

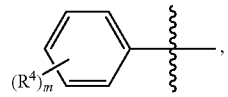

wherein $R^4$ is halo, $C_1$-$C_6$ alkyl, $OR^5$, $NHR^5$, $NO_2$, $CF_3$ or CN; $R^5$ is H or optionally substituted alkyl; and m is 0-5. In some embodiments m is 0 or 1. In some embodiments, $R^1$ is

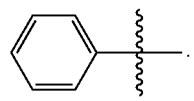 [SMILES: *c1ccccc1]

In some embodiments, $R^5$ is H.

In some embodiments, halo is F.

In some embodiments, $R^2$ is an alkyl, e.g., $C_1$-$C_{10}$ alkyl. In some embodiments, $R^2$ is a substituted $C_1$-$C_{10}$ alkyl and the substituent is selected from the group consisting of $OR^5$, halo, =O, $CO_2R^5$, $NHR^5$, $NO_2$, CN or $CF_3$; and $R^5$ is H or optionally substituted alkyl. In some embodiments, $R^2$ is —$(CH_2)_p$ $CO_2H$, wherein p is 0-9. In some embodiment p is 6.

In some embodiments, $R^3$ is $C_1$-$C_6$ alkyl.

In some other embodiments, $R^3$ is a substituted alkyl. In some embodiments, $R^3$ is an alkyl substituted with an optionally substituted cycloalkyl substituent.

In certain embodiments, $R^3$ is a disubstituted alkyl. In some embodiments, $R^3$ is an alkyl substituted with an optionally substituted cycloalkyl substituent and one other substituent selected from the group consisting of $OR^5$, halo, =O, $CO_2R^5$, $NHR^5$, $NO_2$, CN or $CF_3$; and $R^5$ is H or optionally substituted alkyl. In some embodiments, $R^3$ is an alkyl substituted by two substituents at the same backbone carbon.

In some embodiment, $R^3$ is:

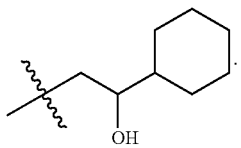 [SMILES: *CC(O)C1CCCCC1]

In one embodiment, compound of formula (I) is:

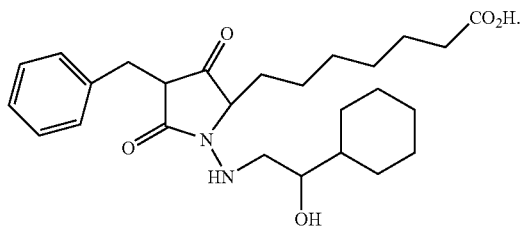 [SMILES: O=C(O)CCCCCCC1C(=O)C(Cc2ccccc2)C(=O)N1NCC(O)C1CCCCC1]

In another embodiment, the present invention provides a method for treating motor neuron disease (MND) comprising administering the compound of formula (II):

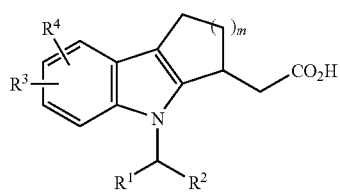

Formula (II)

wherein:

$R^1$ is H or $C_1$-$C_6$ alkyl;

$R^2$ is aryl or heteroaryl, each of which can be optionally substituted;

$R^3$ and $R^4$ are each independently is halo, —$CF_3$, —CN, —$NO_2$, —S(=O)alkyl, —$SO_2$alkyl, $C_1$-$C_6$ alkyl; —C(O)alkyl, —CH(OH)alkyl; and m is 1, 2 or 3.

In some embodiments, m is 1 or 2.

In some embodiments, $R^1$ is H.

In some embodiments, $R^2$ is aryl, e.g., a substituted aryl, e.g., a monosubstituted aryl. In some embodiments, $R^2$ is a substituted phenyl. In some embodiments, $R^2$ is a substituted aryl, wherein the substituent is selected from the group consisting of $OR^5$, halo, =O, $CO_2R^5$, $NHR^5$, $NO_2$, CN or $CF_3$; and $R^5$ is H or optionally substituted alkyl. In some embodiments, $R^2$ is

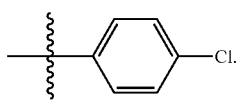 [SMILES: *c1ccc(Cl)cc1]

In some embodiments, the compound of formula (II) is:

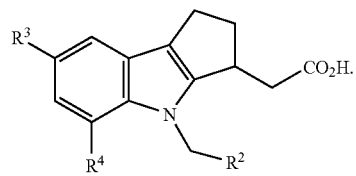

In some embodiments, the compound of formula (II) is:

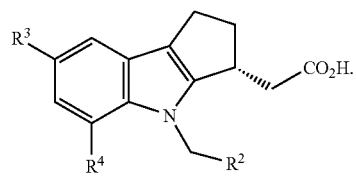

In some embodiments, $R^3$ and $R^4$ is halo and other is —S($O_2$)$CH_3$. In some embodiment, $R^3$ is halo and $R^4$ is —S($O_2$)$CH_3$. In some embodiments, $R^3$ is F and $R^4$ is —S($O_2$)$CH_3$. In some embodiments, $R^4$ is F and $R^3$ is —S($O_2$)$CH_3$.

In some embodiments, both $R^3$ and $R^4$ are halo. In some embodiments, $R^3$ is F and $R^4$ is Br.

In some embodiments, one of $R^3$ and $R^4$ is halo and other is —C(=O)$CH_3$. In some embodiments, $R^3$ is halo and $R^4$ is —C(=O)$CH_3$. In some embodiments, $R^3$ is F and $R^4$ is —C(=O)$CH_3$.

In some embodiments, one of $R^3$ and $R^4$ is halo and other is —CH(OH)$CH_3$. In some embodiments, $R^3$ is halo and $R^4$ is —CH(OH)$CH_3$.

In some embodiments, one of $R^3$ and $R^4$ is —S($O_2$)$CH_3$ and other is —C(=O)$CH_3$ or CH(OH)$CH_3$. In some embodiments, $R^3$ is —S($O_2$)$CH_3$ and $R^4$ is —C(=O)$CH_3$. In some embodiments, $R^3$ is —S($O_2$)$CH_3$ and $R^4$ is —CH(OH)$CH_3$.

In some embodiments, the compound of formula (II) is:

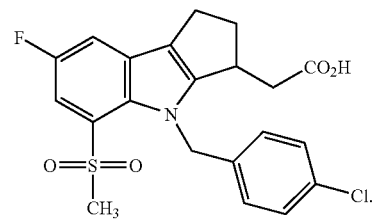

In some embodiments, the compound of formula (II) is:

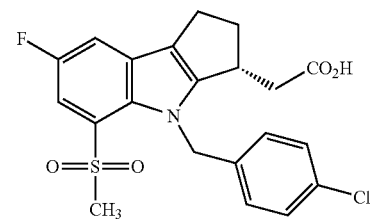 [SMILES: CS(=O)(=O)c1cc(F)cc2c3c(n(Cc4ccc(Cl)cc4)c12)[C@@H](CC(=O)O)CC3]

In one embodiment, the method described herein comprise administering therapeutics typically used for the treatment of MND, e.g. riluzole.

In one embodiment of the methods described herein further comprising selecting a subject diagnosed with motor neuron disease.

In some embodiments, the motor neuron disease includes but is not limited to amyotrophic lateral sclerosis (ALS), primary lateral sclerosis (PLS), progressive muscular atrophy (PMA), pseudobulbar palsy, progressive bulbar palsy, spinal muscular atrophy (SMA) and post-polio syndrome.

In one embodiment, the motor neuron disease is associated with a SOD1 mutation in at least one allele.

In certain embodiments, the present invention provides compositions and methods for detailed mechanistic studies of the interactions between cells such as, without limitation, motor neurons and other cells such as, without limitation, glia. In certain embodiments, a motor neuron of the present invention comprises a mutant motor neuron comprising an allele associates with a neurodegenerative disease, such as, without limitation, ALS. In certain embodiments, a mutant motor neuron comprises a SOD1 mutant allele associated with ALS. For example, a mutant motor neuron may comprise a SOD1G93A allele. In certain embodiments, compositions and methods of the present invention provide an assay for diffusible factor(s), agent(s), etc. toxic to motor neurons. In certain embodiments, the present invention provides a high throughput cell based assay for small molecules that promote survival of mutant SOD1 motor neurons. The present disclosure validates the use of ES cells carrying disease-causing genes to study disease mechanisms.

In certain embodiments, the present invention provides an embryonic stem cell comprising a mutation in a gene involved in motor neuron development and/or maintenance. In certain embodiments, the present invention provides a motor neuron generated by differentiating such an embryonic stem cell under conditions wherein the embryonic stem cell adopts a motor neuron cell fate. In certain embodiments, the present invention provides an embryonic stem cell and/or a motor neuron comprising a mutation in the SOD1 gene. For example, an embryonic stem cell and/or motor neuron of the present invention may comprise a SOD1 mutation wherein a glycine is substituted for the wild type alanine at position 93 of the SOD1 amino acid sequence (referred to herein as a "SOD1G93A" mutation or allele). In certain embodiments, such a mutation in a SOD1 gene is associated with a neurodegenerative disease.

In certain embodiments, an embryonic stem (ES) cell is derived from a mouse bearing a transgene comprising a SOD 1 allele, such as without limitation, a SOD1G93A allele. In certain embodiments, such a mouse bears a transgene comprising a human SOD1G93A allele. Such a transgenic mouse is known to recapitulate many pathologies of the human ALS disease. In certain embodiments, an embryonic stem (ES) cell is a human ES cell bearing a transgene comprising a SOD1 allele, such as without limitation, a SOD1G93A allele. In certain embodiments, transgenic ES cells are differentiated into motor neurons in large numbers (e.g., such as by one or more methods described in Wichterle, H., Lieberam, I., Porter, J. A. & Jessell, T. M. Directed differentiation of embryonic stem cells into motor neurons. Cell 110, 385-97, 2002) and co-cultured either with ES-derived cells that arise during the differentiation process and/or with other cells that contribute to the survival, maintenance and/or differentiation of such transgenic ES cells. For example, transgenic ES cells may be differentiated into motor neurons in the presence of primary mouse and/or human glial cells. In certain embodiments, such primary mouse and/or human glial cells comprise a wild-type genotype. In certain embodiments, such primary mouse and/or human glial cells comprise a non-wild-type genotype. For example, such glial cells may comprise a mutant SOD1 allele, e.g., a SOD1G93A allele. Such a mutant SOD1 allele may be provided as a transgene.

In certain embodiments, motor neurons of such cultures display one or more abnormalities typical of a phenotype observed in a particular disease. In certain embodiments, motor neurons of such cultures display one or more abnormalities typical of a phenotype observed in a neurodegenerative disease. For example, such motor neurons may display abnormalities typical of those seen in the motor neurons of ALS patients and/or ALS transgenic animals.

In certain embodiments, the present invention provides novel in vitro model systems to study ALS and/or other neurodegenerative diseases, in which the factors directly influencing motor neuron development, differentiation and/or survival can be investigated. Certain of such systems are based on the differentiation of embryonic stem (ES) cells derived from mice comprising a mutant SOD1 allele. Certain of such systems are based on the differentiation of human embryonic stem (ES) cells comprising a mutant SOD1 allele. An exemplary mutant SOD1 allele that can be used in accordance with methods and compositions of the present invention is the SOD1G93A mutation, although systems of the present invention are not limited to this mutation.

In certain embodiments, in vitro model systems of the present invention are used to screen for a test agent that affects the development, differentiation and/or survival of motor neurons. In certain embodiments, such in vitro model systems are used to screen for a test agent that affects the survival of wild type motor neurons. In certain embodiments, such in vitro model systems are used to screen for a test agent that affects the development, differentiation and/or survival of motor neurons that comprise one or more mutations. For example, such mutant motor neurons may comprise a mutation associated with a neurodegenerative disease, such as for example, ALS. In certain embodiments, such mutant motor neurons comprise a mutation in the SOD1 gene, e.g. a SOD1G93A mutation. In certain embodiments, the invention provides methods of identifying an agent that affects the survival of a mutant motor neuron. For example, certain of such methods comprise providing a mutant motor neuron comprising a SOD1 mutant allele, providing a test agent, contacting the mutant motor neuron with the test agent, and determining the effect of the test agent on survival of the mutant motor neuron by comparing the survival of the mutant motor neuron to the survival of a control motor neuron lacking the SOD1 mutant allele, which control motor neuron is contacted with the test agent for a period of time and under conditions identical to that of the SOD1 mutant motor neuron. In certain embodiments, a test agent is a cell, a small molecule, a hormone, a vitamin, a nucleic acid molecule, an enzyme, an antibody, an amino acid, and/or a virus. In certain embodiments, the test agent is an agent that reduces the expression or activity of a gene or a product of a gene in Table 2 (e.g., a product of a gene in Table 2 which is involved in inflammation, an immune response, transcription, signaling, or a metabolic pathway). In certain embodiments, the test agent is an agent that reduces the expression or activity of a prostaglandin D receptor.

In certain embodiments, the invention provides methods of identifying a factor that has a non-cell autonomous effect on the survival of a motor neuron. For example, certain of such methods comprise providing a motor neuron, identifying a first cell, which first cell negatively affects survival of the motor neuron, identifying a second cell, which second cell does not negatively affect survival of the motor neuron, isolating a factor from the either the first or second cell, wherein the factor is either: i) a factor from the first cell that contributes to the negative effect on survival of the motor neuron; or ii) a factor from the second cell that contributes to survival of the motor neuron. In certain embodiments, the first cell, second cell or both is a glial cell. In certain embodiments, the first cell, second cell or both comprises a mutation that is associated with amyloid lateral sclerosis, e.g. a SOD1 mutation such as without limitation a SOD1G93A allele.

In certain embodiments, the invention provides methods of identifying a factor that has a non-cell autonomous effect on the survival of a motor neuron. For example, certain of such methods comprise providing a motor neuron, culturing the motor neuron in the presence of a test cell such that survival of the motor neuron is negatively affected as compared to survival of a motor neuron cultured in the presence of a control cell, and identifying a factor present in the test cell, which factor contributes to the negative effect on survival of the motor neuron. In certain embodiments, the invention provides methods of identifying a factor that has a non-cell autonomous effect on the survival of a motor neuron, which methods comprise providing a motor neuron, culturing the motor neuron in the presence of a test cell such that survival of the motor neuron is negatively positively affected as compared to survival of a motor neuron cultured in the presence of a control cell, and identifying a factor that is absent in the test cell, which factor contributes to the positive effect on survival of the motor neuron.

In certain embodiments, the invention provides methods of identifying a test agent that modulates the non-cell autonomous effect of a test cell on the survival of a motor neuron. For example, certain of such methods comprise providing a motor neuron, culturing the motor neuron in the presence of a (i) test cell such that survival of the motor neuron is negatively affected as compared to survival of a motor neuron cultured in the presence of a control cell, and (ii) a test agent, wherein a change in the survival of the motor neuron in the presence of the test agent as compared to the survival of the motor neuron in the absence of the test agent indicates that the test agent modulates the non-cell autonomous effect of a test cell. In certain embodiments, the test agent is an agent that reduces the expression or activity of a gene or a product of a gene in Table 2 (e.g., a product of a gene in Table 2 which is involved in inflammation, an immune response, transcription, signaling, or a metabolic pathway). In certain embodiments, the test agent is an agent that reduces the expression or activity of a prostaglandin D receptor.

In certain embodiments, the invention provides methods of identifying a factor that has a cell autonomous effect on the survival of a motor neuron. For example, certain of such methods comprise providing a mutant motor neuron comprising a first SOD1 mutation, providing a control motor neuron lacking the first SOD1 mutation, culturing the mutant motor neuron, determining the effect of the first SOD1 mutation on survival of the mutant motor neuron by comparing the survival of the mutant motor neuron to the survival of the control motor neuron, which control motor neuron is cultured for a period of time and under conditions identical to that of the mutant motor neuron, and isolating a factor from the either the mutant motor neuron or the control motor neuron, wherein the factor is either: i) a factor from the mutant motor neuron that contributes to the negative effect on survival of the motor neuron; or ii) a factor from the control motor neuron that contributes to survival of the motor neuron.

In certain embodiments, in vitro model systems of the present invention are used to screen for a factor that has a non-cell autonomous effect on the development, differentiation and/or survival of a motor neuron, e.g. a SOD1 mutant motor neuron such as a SOD1G93A mutant motor neuron. In certain embodiments, such a factor comprises a factor originating from another motor neuron. In certain embodiments, such a factor comprises a factor originating from another cell that is not a motor neuron. In certain embodiments, such a factor originates from a glial cell. Such a factor may have a negative effect on the development, differentiation and/or survival of a motor neuron. Alternatively, such a factor may contribute to the development, differentiation and/or survival of a motor neuron such that its absence negatively affects survival of the motor neuron.

In vitro model systems of the present invention are useful for the identification of factors, agents, etc. that both positively and negatively affect motor neuron survival. In certain embodiments, one or more factors, agents, etc. that affect motor neuron survival are identified by using SOD1 mutant glial cells, e.g. glial cells comprising a SOD1G93A mutation. In certain embodiments, in vitro model systems of the present invention utilize human motor neurons and/or other cell types derived from human ES cells. Such in vitro model systems may be advantageously employed for the human physiological validation of findings from animal models, such as, without limitation, animal models that recapitulate neurodegenerative diseases such as ALS and/or other neurodegenerative diseases. Additionally or alternatively, such in vitro model systems may be advantageously employed to identify novel factors, agents, etc. that affect human motor neuron development and/or contribute to a disease state, such as, without limitation, a neurodegenerative disease, e.g. ALS, in the absence of an animal model. Additionally or alternatively, such in vitro model systems may be advantageously employed to illuminate the target, efficacy, toxicity, mode of action, etc. of factors, agents, etc. that affect human motor neuron development and/or contribute to a disease state, such as, without limitation, a neurodegenerative disease, e.g. ALS.

Certain embodiments of the present invention are discussed in detail below. Those of ordinary skill in the art will understand, however, that various modifications to these embodiments are within the scope of the appended claims. It is the claims and equivalents thereof that define the scope of the present invention, which is not and should not be limited to or by this description of certain embodiments.

Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims.

For simplicity, chemical moieties are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms "alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The term "halo" refers to any radical of fluorine, chlorine, bromine or iodine.

The term "acyl" refers to an alkylcarbonyl, cycloalkylcarbonyl, arylcarbonyl, heterocyclylcarbonyl, or heteroarylcarbonyl substituent, any of which may be further substituted by substituents. Exemplary acyl groups include, but are not limited to, $(C_1-C_6)$alkanoyl (e.g., formyl, acetyl, propionyl, butyryl, valeryl, caproyl, t-butylacetyl, etc.), $(C_3-C_6)$cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions.

The term "alkyl" refers to saturated non-aromatic hydrocarbon chains that may be a straight chain or branched chain, containing the indicated number of carbon atoms (these include without limitation methyl, ethyl, propyl, allyl, or propargyl), which may be optionally inserted with N, O, S, SS, $SO_2$, C(O), C(O)O, OC(O), C(O)N or NC(O). For example, $C_1-C_6$ indicates that the group may have from 1 to 6 (inclusive) carbon atoms in it.

The term "alkenyl" refers to an alkyl that comprises at least one double bond. Exemplary alkenyl groups include, but are not limited to, for example, ethenyl, propenyl, butenyl, 1-methyl-2-buten-1-yl and the like.

The term "alkynyl" refers to an alkyl that comprises at least one triple bond.

The term "alkoxy" refers to an —O-alkyl radical.

The term "aminoalkyl" refers to an alkyl substituted with an amino.

The term "mercapto" refers to an —SH radical.

The term "thioalkoxy" refers to an —S-alkyl radical.

The term "aryl" refers to monocyclic, bicyclic, or tricyclic aromatic ring system wherein 0, 1, 2, 3, or 4 atoms of each ring may be substituted by a substituent. Exemplary aryl groups include, but are not limited to, phenyl, naphthyl, anthracenyl, azulenyl, fluorenyl, indanyl, indenyl, naphthyl, phenyl, tetrahydronaphthyl, and the like.

The term "arylalkyl" refers to alkyl substituted with an aryl.

The term "cyclyl" or "cycloalkyl" refers to saturated and partially unsaturated cyclic hydrocarbon groups having 3 to 12 carbons, for example, 3 to 8 carbons, and, for example, 3 to 6 carbons, wherein the cycloalkyl group additionally may be optionally substituted. Exemplary cycloalkyl groups include, but are not limited to, cyclopropyl, cyclobutyl, cyclopentyl, cyclopentenyl, cyclohexyl, cyclohexenyl, cycloheptyl, cyclooctyl, and the like.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Exemplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, and the like.

The term "heteroarylalkyl" refers to an alkyl substituted with a heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Exemplary heterocyclyl groups include, but are not limited to piperazinyl, pyrrolidinyl, dioxanyl, morpholinyl, tetrahydrofuranyl, and the like.

The term "haloalkyl" refers to an alkyl group having one, two, three or more halogen atoms attached thereto. Exemplary haloalkyl groups include, but are not limited to chloromethyl, bromoethyl, trifluoromethyl, and the like.

The term "optionally substituted" means that the specified group or moiety, such as an aryl group, heteroaryl group and the like, is unsubstituted or is substituted with one or more (typically 1-4 substituents) independently selected from the group of substituents listed below in the definition for "substituents" or otherwise specified.

The term "substituents" refers to a group "substituted" on an alkyl, alkenyl, alkynyl, cycloalkyl, aryl, heterocyclyl, heteroaryl, acyl, amino group at any atom of that group. Suitable substituents include, without limitation, halo, hydroxy, oxo, nitro, haloalkyl, alkyl, alkenyl, alkynyl, alkaryl, aryl, aralkyl, alkoxy, aryloxy, amino, acylamino, alkylcarbanoyl, arylcarbanoyl, aminoalkyl, alkoxycarbonyl, carboxy, hydroxyalkyl, alkylthio, $CF_3$, N-morphilino, phenylthio, alkanesulfonyl, arenesulfonyl, alkanesulfonamido, arenesulfonamido, aralkylsulfonamido, alkylcarbonyl, acyloxy, cyano or ureido. In some embodiments, substituent can itself be optionally substituted. In some cases, two substituents, together with the carbons to which they are attached to can form a ring.

An "antibody" that can be used according to the methods described herein includes complete immunoglobulins, antigen binding fragments of immunoglobulins, as well as antigen binding proteins that comprise antigen binding domains of immunoglobulins. Antigen binding fragments of immunoglobulins include, for example, Fab, Fab', F(ab')$_2$, scFv and dAbs. Modified antibody formats have been developed which retain binding specificity, but have other characteristics that may be desirable, including for example, bispecificity, multivalence (more than two binding sites), and compact size (e.g., binding domains alone). Single chain antibodies lack some or all of the constant domains of the whole antibodies from which they are derived. Therefore, they can overcome some of the problems associated with the use of whole antibodies. For example, single-chain antibodies tend to be free of certain undesired interactions between heavy-chain constant regions and other biological molecules. Additionally, single-chain antibodies are considerably smaller than whole antibodies and can have greater permeability than whole antibodies, allowing single-chain antibodies to localize and bind to target antigen-binding sites more efficiently. Furthermore, the relatively small size of single-chain antibodies makes them less likely to provoke an unwanted immune response in a recipient than whole antibodies. Multiple single chain antibodies, each single chain having one VH and one VL domain covalently linked by a first peptide linker, can be covalently linked by at least one or more peptide linker to form multivalent single chain antibodies, which can be monospecific or multispecific. Each chain of a multivalent single chain antibody includes a variable light chain fragment and a variable heavy chain fragment, and is linked by a peptide linker to at least one other chain. The peptide linker is composed of at least fifteen amino acid residues. The maximum number of linker amino acid residues is approximately one hundred. Two single chain antibodies can be combined to form a diabody, also known as a bivalent dimer. Diabodies have two chains and two binding sites, and can be monospecific or bispecific. Each chain of the diabody includes a VH domain connected to a VL domain. The domains are connected with linkers that are short enough to prevent pairing between domains on the same chain, thus driving the pairing between complementary domains on different chains to recreate the two antigen-binding sites. Three single chain antibodies can be combined to form triabodies, also known as trivalent trimers. Triabodies are constructed with the amino acid terminus of a VL or VH domain directly fused to the carboxyl terminus of a VL or VH domain, i.e., without any linker sequence. The triabody has three Fv heads with the polypeptides arranged in a cyclic, head-to-tail fashion. A possible conformation of the triabody is planar with the three binding sites located in a plane at an angle of 120 degrees from one another. Triabodies can be monospecific, bispecific or trispecific. Thus, antibodies useful in the methods described herein include, but are not limited to, naturally occurring antibodies, bivalent fragments such as $(Fab')_2$, monovalent fragments such as Fab, single chain antibodies, single chain Fv (scFv), single domain antibodies, multivalent single chain antibodies, diabodies, triabodies, and the like that bind specifically with an antigen.

Antibodies can also be raised against a polypeptide or portion of a polypeptide by methods known to those skilled in the art. Antibodies are readily raised in animals such as rabbits or mice by immunization with the gene product, or a fragment thereof. Immunized mice are particularly useful for providing sources of B cells for the manufacture of hybridomas, which in turn are cultured to produce large quantities of monoclonal antibodies. Antibody manufacture methods are described in detail, for example, in Harlow et al., 1988 in: Antibodies, A Laboratory Manual, Cold Spring Harbor, N.Y. While both polyclonal and monoclonal antibodies can be used in the methods described herein, it is preferred that a monoclonal antibody is used where conditions require increased specificity for a particular protein.

As used herein, the term "vector" refers to a nucleic acid molecule capable of transporting another nucleic acid to which it has been linked. One type of vector is a "plasmid", which refers to a circular double stranded DNA loop into which additional nucleic acid segments can be ligated. Another type of vector is a viral vector, wherein additional nucleic acid segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors", or more simply "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, lentiviruses, adenoviruses and adeno-associated viruses), which serve equivalent functions. In one embodiment, lentiviruses are used to deliver one or more siRNA molecule of the present invention to a cell.

Within an expression vector, "operably linked" is intended to mean that the nucleotide sequence of interest is linked to the regulatory sequence(s) in a manner which allows for expression of the nucleotide sequence (e.g., in an in vitro transcription/translation system or in a target cell when the vector is introduced into the target cell). The term "regulatory sequence" is intended to include promoters, enhancers and other expression control elements (e.g., polyadenylation signals). Such regulatory sequences are described, for example, in Goeddel; Gene Expression Technology Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). Furthermore, the RNA interfering agents may be delivered by way of a vector comprising a regulatory sequence to direct synthesis of the siRNAs of the invention at specific intervals, or over a specific time period. It will be appreciated by those skilled in the art that the design of the expression vector can depend on such factors as the choice of the target cell, the level of expression of siRNA desired, and the like.

The expression vectors of the invention can be introduced into target cells to thereby produce siRNA molecules of the present invention. In one embodiment, a DNA template, e.g., a DNA template encoding the siRNA molecule directed against the mutant allele, may be ligated into an expression vector under the control of RNA polymerase III (Pol III), and delivered to a target cell. Pol III directs the synthesis of small, noncoding transcripts which 3' ends are defined by termination within a stretch of 4-5 thymidines. Accordingly, DNA templates may be used to synthesize, in vivo, both sense and antisense strands of siRNAs which effect RNAi (Sui, et al. (2002) PNAS 99(8):5515).

"Agent", "Test agent": The terms "agent" and "test agent" as used herein refer to a compound or other entity that is tested to determine whether it has an effect on the differentiation, development and/or survival of a cell. As non-limiting examples, a test agent may comprise a cell, a small molecule, a hormone, a vitamin, a nucleic acid molecule, an enzyme, an amino acid, and/or a virus. Those of ordinary skill in the art will be aware of other test agents that may be tested for their effect(s) on differentiation, development and/or survival of a cell. In certain embodiments, a differentiating cell is subjected to a test agent before, during and/or after differentiation to determine its effect(s) on differentiation, development and/or survival of a cell. For example, an embryonic stem cell undergoing differentiation into a cell type of interest may be subjected to a test agent before, during and/or after differentiation. In certain embodiments, an embryonic stem cell undergoing differentiation into a motor neuron is subjected to a test agent before, during and/or after differentiation. In certain embodiments, a test agent that is identified as having one or more effects on the differentiation, development and/or survival of a cell is used in the treatment, prevention and/or cure of a disease of interest.

"Embryonic stem cell", "ES cell": The terms "embryonic stem cell" and "ES cell" as used herein refer to an undifferentiated stem cell that is derived from the inner cell mass of a blastocyst embryo and is pluripotent, thus possessing the capability of developing into any organ or tissue type or, at least potentially, into a complete embryo. Embryonic stem cells appear to be capable of proliferating indefinitely, and of differentiating into all of the specialized cell types of a mammal, including the three embryonic germ layers (endoderm, mesoderm, and ectoderm), and all somatic cell lineages and the germ line. As non-limiting examples, embryonic stem cells have been shown to be capable of being induced to differentiate into cardiomyocytes (Paquin et al., Proc. Nat. Acad. Sci., 99:9550-9555, 2002), hematopoietic cells (Weiss et al., Hematol. Oncol. Clin. N. Amer., 11(6):1185-98, 1997; also U.S. Pat. No. 6,280,718), insulin-secreting beta cells (Assady et al., Diabetes, 50(8):1691-1697, 2001), and neural progenitors capable of differentiating into astrocytes, oligodendrocytes, and mature neurons (Reubinoff et al., Nature Biotechnology, 19:1134-1140, 2001; also U.S. Pat. No. 5,851,832). One of ordinary skill in the art will be aware of other cell types that have been derived from embryonic stem cells.

"SOD1": As will be clear from context, the term "SOD1" as used herein refers to either the gene encoding superoxide dismutase 1 or the enzyme encoded by this gene. The SOD1 gene or gene product is known by other names in the art including, but not limited to, ALS1, Cu/Zn superoxide dismutase, indophenoloxidase A, IPDA, and SODC_HUMAN. Those of ordinary skill in the art will be aware of other synonymous names that refer to the SOD1 gene or gene product. The SOD1 enzyme neutralizes supercharged oxygen molecules (called superoxide radicals), which can damage cells if their levels are not controlled. The human SOD1 gene maps to cytogenetic location 21q22.1. Certain mutations in SOD1 are associated with ALS in humans including, but not limited to, Ala4Val, Gly37Arg and Gly93Ala, and more than one hundred others. Those of ordinary skill in the art will be aware of these and other human mutations associated with ALS. Certain compositions and methods of the present invention comprise or employ cells comprising a SOD1 mutation.

"SOD 1 mutations" refer to mutations in the human SOD1 gene (NC_000021.8; NT_011512.11; AC_000064.1; NW_927384.1; AC_000153.1; NW_001838706.1 NM_000454.4; NP_000445.1 and NCBI Entrez GeneID: 6647) including but are not limited to Ala4Val, Cys6Gly, Val7Glu, Leu8Val, Gly10Val, Gly12Arg, Val14Met, Gly16Ala, Asn19Ser, Phe20Cys, Glu21Lys, Gln22Leu, Gly37Arg, Leu38Arg, Gly41Ser, His43Arg, Phe45Cys, His46Arg, Val47Phe, His48Gln, Glu49Lys, Thr54Arg, Ser59Ile, Asn65Ser, Leu67Arg, Gly72Ser, Asp76 Val, His80Arg, Leu84Phe, Gly85Arg, Asn86Asp, Val87Ala, Ala89Val, Asp90Ala, Gly93Ala, Ala 95Thr, Asp96Asn, Val97Met, Glu100Gly, Asp101Asn, Ile104Phe, Ser105Leu, Leu106Val, Gly108Val, Ile112Thr, Ile113Phe, Gly114Ala, Arg115Gly, Val118Leu, Ala140Gly, Ala145Gly, Asp124Val, Asp124Gly, Asp125His, Leu126Ser, Ser134Asn, Asn139His, Asn139Lys, Gly141Glu, Leu144Phe, Leu144Ser, Cys146Arg, Ala145Thr, Gly147Arg, Val148Gly, Val148Ile, Ile149Thr, Ile151Thr, and Ile151Ser. SOD1 is also known as ALS, SOD, ALS1, IPOA, homodimer SOD1. "SOD 1 mutation" databases can be found at Dr. Andrew C. R. Martin website at the University College of London (the World Wide Web address at "www" "period" bioinf "period" org "period" uk), the ALS/SOD1 consortium website (the World Wide Web address at "www" "period" alsod "period" org) and the human gene mutation database (HGMD®) at the Institute of Medical Genetics at Cardiff, United Kingdom.

"Stem-cell producing condition": The term "stem-cell producing condition" as used herein refers to a condition or set of conditions that permits and/or drives a cell to become a stem cell. In certain embodiments, an embryonic cell is permitted and/or driven to become an embryonic stem cell by subjecting such an embryonic cell to a stem-cell producing condition. For example, an embryonic blastomere may permitted and/or driven to become an embryonic stem cell by isolating the embryonic blastomere from the inner cell mass of a blastocyst and culturing the embryonic blastomere under stem-cell producing conditions, such that at least one blastomere proliferates into a pluripotent embryonic stem cell. In certain embodiments, a transgenic embryonic stem cell is generated by producing a transgenic cell according to one or more methods of the present invention, allowing the transgenic cell to develop into a transgenic blastocyst comprising a plurality of transgenic blastomeres, isolating one or more transgenic blastomeres from the inner cell mass of the transgenic blastocyst, and culturing the isolated transgenic blastomere(s) under stem-cell producing conditions such that at least one transgenic blastomere develops into a pluripotent transgenic embryonic stem cell.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

In the context of the invention, the term "treating" or "treatment", as used herein, refers to a method that is aimed at delaying or preventing the onset of a pathology (e.g. death of motor neurons), at reversing, alleviating, inhibiting, slowing down or stopping the progression, aggravation or deterioration of the symptoms of the pathology. Treating or treatment mean to relieve or alleviate at least one symptom associated with such condition, or to slow or reverse the progression or anticipated progression of such condition, at bringing about ameliorations of the symptoms of the pathology. In one embodiment, the symptom of a motor neuron disease is alleviated by at least 20%, at least 30%, at least 40%, or at least 50%. In one embodiment, the symptom of a motor neuron disease is alleviated by more that 50%. In one embodiment, the symptom of a motor neuron disease is alleviated by 80%, 90%, or greater.

The pharmaceutical compositions of the invention are administered in a therapeutically effective amount. As used herein, the phrase "therapeutically effective amount" refers to an amount that provides a therapeutic benefit in the treatment, prevention, or management of pathological processes mediated by PGD2 DP1 expression or activity (e.g. death of motor neurons) or an overt symptom of pathological processes mediated by PGD2 DP1 expression or activity. The specific amount that is therapeutically effective can be readily determined by an ordinary medical practitioner, and may vary depending on factors known in the art, such as, for example, the patient's history and age, the stage of pathological processes, and the administration of other agents that inhibit pathological processes in motor neuron disease.

Embryonic Stem Cells and their Generation

Stem cells typically share two important characteristics that distinguish them from other types of cells. First, they are unspecialized cells that are capable of maintaining their unspecialized state and of renewing themselves for long periods through cell division. Second, under appropriate conditions, they can be induced to differentiate into cells with specialized functions. Several types of stem cells have been identified including adult stem cells, umbilical cord stem cells, and embryonic stem cells.

Embryonic stem cells may be characterized by any of several criteria, which criteria will be known by those of ordinary skill in the art. For example, embryonic stem cells are typically capable of continuous indefinite replication in vitro. Continued proliferation for a long period of time (e.g., 6 months, one year or longer) of culture is a sufficient evidence for immortality, as primary cell cultures without this property fail to continuously divide for such a length of time (Freshney, Culture of animal cells. New York: Wiley-Liss, 1994). In certain embodiments, embryonic stem will continue to proliferate in vitro under appropriate culture conditions for longer than one year, and maintain the developmental potential to contribute all three embryonic germ layers throughout this time. Such developmental potential can be demonstrated by the injection of embryonic stem cells that have been cultured for a prolonged period (over a year) into SCID mice and then histologically examining the resulting tumors. However, length of time in culture is not the sole criteria that may be used to identify an embryonic stem cell, and even though cells have grown in culture for less than 6 months, such cells may nevertheless be embryonic stem cells.

Additionally or alternatively, embryonic stem cells may be identified by the expression of certain markers, including but not limited to cell surface markers. As will be understood by those of ordinary skill in the art, embryonic stem cells from different species will exhibit species-specific markers on their cell surfaces. For example, Thomson (U.S. Pat. Nos. 5,843, 780 and 6,200,806, each of which is incorporated herein in its entirety by reference) discloses certain cell surface markers that may be used to identify embryonic stem cells derived from primates. Furthermore, Stage Specific Embryonic Antigens (SSEAs) are monoclonal antibodies that recognize defined carbohydrate epitopes and may also be used to identify embryonic stem cells. Embryonic stem cells derived from different species exhibit different patterns of SSEAs. For example, undifferentiated primate ES cells (including human ES cells) express SSEA-3 and SSEA-4, but not SSEA-1. Conversely, undifferentiated mouse ES cells express SSEA-1, but not SSEA-3 or SSEA-4. Additionally or alternatively, markers that are not exhibited on the surface of a cell may be used to identify an embryonic stem cell. For example, the homeodomain transcription factor Oct 4 (also termed Oct-3 or Oct3/4) is frequently used as a marker for totipotent embryonic stem cells. Those of ordinary skill in the art will be aware of cell surface and other markers that are useful in identifying embryonic stem cells, including markers diagnostic of a given species that can be used to identify an embryonic stem cell from that species.

Additionally or alternatively, embryonic stem cells may be identified by the capacity to develop into all of the specialized cell types of a mammal, including the three embryonic germ layers (endoderm, mesoderm, and ectoderm), and all somatic cell lineages and the germ line. Additionally and/or alternatively, embryonic stem cells may be identified by the capacity to participate in normal development when transplanted into a preimplantation embryo to generate a chimeric embryo.

Cultured cells that have proliferated in cell culture for a long period of time (e.g., six or more months) without differentiating, are pluripotent, and appear genetically normal are typically considered to be embryonic stem cells. In certain embodiments, an embryonic stem cell of the present invention comprises a human embryonic stem cell. In certain embodiments, an embryonic stem cell of the present invention comprises a non-human embryonic stem cell. For example, a non-human embryonic stem cell of the present invention may include, but is not limited to, a mouse, rat, pig, sheep, goat, and/or a primate stem cell. Those of ordinary skill in the art will be aware of other non-human stem cells that may be used in accordance with the present invention.

The capacity of embryonic stem cells (ES) to self renew in culture, while retaining their pluripotent potential, provides the opportunity to produce virtually unlimited numbers of differentiated cell types to replenish those lost as a consequence of disease (Evans, M. J. & Kaufman, M. H. Establishment in culture of pluripotential cells from mouse embryos. Nature 292, 154-6, 1981; Martin, G. R. Isolation of a pluripotent cell line from early mouse embryos cultured in medium conditioned by teratocarcinoma stem cells. Proc Natl Acad Sci USA 78, 7634-8, 1981). An alternative, but equally important potential of ES cells is to provide insights into disease mechanisms (Lerou, P. H. & Daley, G. Q. Therapeutic potential of embryonic stem cells. Blood Rev 19, 321-31, 2005; Ben-Nun, I. F. & Benvenisty, N. Human embryonic stem cells as a cellular model for human disorders. Mol Cell Endocrinol 252, 154-9, 2006). ES cells carrying the genes responsible for a particular disease can be induced to differentiate into the cell types affected in that disease. Studies of the differentiated cells in culture could provide important information regarding the molecular and cellular nature of events leading to pathology.

In certain embodiments, this approach is used to develop an in vitro model of Amyotrophic Lateral Sclerosis ("ALS"). As described more fully below in the Examples section of the present application, embryonic stem cell lines were derived from normal mice, and from mice that over-express either the wild-type human SOD1 transgene or the mutant SOD1G93A transgene, the latter of which is responsible for one type of familial ALS (see Example section). Using the methods established by Wichterle et al (2002) the three ES cell lines were differentiated into motor neurons in culture. The wild-type SOD1 and the mutant SOD1G93A motor neurons produce high levels of the corresponding human SOD1 proteins, and they both display properties that characterize bone fide motor neurons. These motor neurons could be maintained in long-term culture, providing the opportunity to detect differences between the mutant SOD1G93A ES cell-derived motor neurons and those derived from control cell lines.

In certain embodiments, embryonic stem cells are generated by culturing cells from the inner cell mass in a culture dish that is coated with a feeder layer comprising mouse embryonic skin cells that have been treated so they will not divide. Such a feeder layer gives the inner cell mass cells a sticky surface to which they can attach and also releases nutrients into the culture medium. In certain embodiments, cells from the inner cell mass are cultured in a culture dish that is not coated with a feeder layer. Such embodiments provide certain advantages including reduction of the risk that viruses or other macromolecules in the mouse cells may be transmitted to the cultured cells.

In certain embodiments, embryonic stem cells are generated by subjecting cells to stem-cell producing conditions. Stem-cell producing conditions are known to those of ordinary skill in the art and can often vary between species. For example, leukemia inhibitory factor (LIF) is necessary and sufficient to prevent differentiation of mouse embryonic stem cells and to allow them to grow in an undifferentiated state indefinitely. Conversely, for primate embryonic stem cells, at least one group has reported that growth on a fibroblast feeder layer is required to prevent them from differentiating (see e.g., U.S. Pat. Nos. 5,843,780 and 6,200,806, incorporated herein by reference in their entirety). One of ordinary skill in the art will be aware of appropriate stem-cell producing conditions including, but not limited to, culture media and/or culturing conditions that permit and/or drive a cell of a given species to become a stem cell.

In certain embodiments, embryonic stem cells of the present invention are generated by any of a variety of methods disclosed in U.S. Provisional Patent Application No. 60/926,525, filed Apr. 26, 2007, which is incorporated herein by reference in its entirety. For example, in certain embodiments, an embryonic stem cell is generated by transferring nuclear-derived genetic material from a donor cell to a recipient cell to generate a transgenic cell, after which the transgenic cell is allowed to develop into a blastocyst and a blastomere cell from the inner cell mass is isolated and/or cultured (and optionally passaged for several generations) under stem-cell producing conditions, resulting in generation of an embryonic stem cell syngenic with the nuclear-derived genetic material removed from the donor cell used to generate the transgenic cell.

In certain embodiments, embryonic stem cells of the present invention are generated such that the generated embryonic stem cells comprise a mutation associated with a disease of interest. For example, embryonic stem cells may be generated which contain a mutation associated with a neurodegenerative disease. Exemplary neurodegenerative diseases include, but are not limited to: ALS, Parkinson's disease, and Alzheimer's disease. Those of ordinary skill in the art will be aware of other neurodegenerative diseases of interest, as well as mutations associated with such diseases.

In certain embodiments, an embryonic stem cell is generated that comprises a mutation associated with ALS. For example, an embryonic stem cell may be generated that comprises a mutation in the SOD1 gene, e.g., Ala4Val, Gly37Arg and/or Gly93Ala. In certain embodiments, an embryonic stem cell is generated that comprises a SOD1G93A allele. In certain embodiments, an embryonic stem cell is generated that comprises a human SOD1G93A allele.

In certain embodiments, an embryonic stem cell comprises a mutation in a gene associated with neurodegenerative disease, which gene is present as a transgene. For example, an endogenous gene associated with a neurodegenerative disease may be deleted or otherwise inactivated in such an embryonic stem cell by any of a variety of techniques known to those skilled in the art, and a transgene comprising a mutant copy of the endogenous gene may be introduced into the embryonic stem cell by any of a variety of techniques known to those skilled in the art. In certain embodiments, such a transgene is integrated into the genome of the embryonic stem cell. In certain embodiments, such a transgene is not integrated into the genome of the embryonic stem cell.

Once embryonic stem cell lines are established, batches of such embryonic stem cell lines can be frozen and for future culturing and/or experimentation.

Differentiation into Motor Neurons

In certain embodiments of the present invention, an embryonic stem cell is subjected to conditions that result in the embryonic stem cell differentiating into a motor neuron. For example, embryonic stem cells may be dissociated into a single-cell suspension, allowed to spontaneously aggregate into embryoid bodies over a first period of time (e.g. 48 hours, although such a period of time may be increased or decreased depending on other conditions to which the embryonic stem cells are subjected), and then treated with a suitable differentiation factor or factors for a second period of time such that the embryonic stem cells differentiate into motor neurons. By way of example, such differentiation factors may include retinoic acid (RAc) and soluble sonic hedgehog (Shh), which may be administered for, e.g., 5 days. Other differentiation factor(s) and condition(s) will be known to those of ordinary skill in the art.

In certain embodiments, a motor neuron differentiated from an embryonic stem cell comprises a mutation in a gene associated with neurodegenerative disease. As non-limiting examples, such a neurodegenerative disease may include ALS, Parkinson's disease, Alzheimer's disease or any number of other neurodegenerative diseases known to those of skill in the art. A variety of genes are known to be associated with neurodegenerative diseases. As one non-limiting example, mutations in the SOD1 gene are known to be associated with the neurodegenerative disease ALS. For example, in humans, Gly92Ala, Ala4Val and Gly37Arg mutations are associated with the onset and progression of ALS. Those of ordinary skill in the art will be aware of other SOD1 mutations associated with ALS. In certain embodiments, compositions and method of the present invention comprise or employ human motor neurons comprising a SOD1G93A mutation such as Gly92Ala, Ala4Val and/or Gly37Arg.

In mice, the dominant SOD1G93A mutation is associated with ALS-like phenotype. Thus, in certain embodiments, the present invention comprises mouse motor neurons comprising a SOD1G93A mutation. In certain embodiments, the present invention comprises human motor neurons comprising a SOD1G93A mutation.

A number of changes characteristic of neurodegeneration in ALS were observed in mouse mutant SOD1G93A motor neurons between 14 and 28 days (for additional detail, see Examples section below). First, the SOD1G93A protein changed its intracellular localization, forming inclusions that increased in size and density. Second, the levels of ubiquitin increased. Third, some motor neurons expressed activated caspase-3 and displayed cytoplasmic staining with cytochrome c antibodies. Finally, a significant difference in survival was observed between mutant SOD1G93A motor neurons and the controls. Thus, many of the late onset pathologies observed in both human ALS and SOD1G93A mice are recapitulated in this in vitro model, including the loss of motor neurons, which is ultimate cause of symptoms in patients.

In certain embodiments, methods of the present invention comprise using human and/or non-human SOD1 mutant motor neurons to screen for test agents that affect motor neuron differentiation, development and/or survival. In certain embodiments, methods of the present invention comprise using such SOD1 mutant motor neurons to identify a factor that has a non-cell autonomous effect on the differentiation, development and/or survival of a motor neuron.

In certain embodiments, a motor neuron differentiated from an embryonic stem cell comprises a mutation in a gene associated with neurodegenerative disease, which gene is present as a transgene. For example, an endogenous gene associated with a neurodegenerative disease may be deleted or otherwise inactivated in an embryonic stem cell from which such a motor neuron is derived by any of a variety of techniques known to those skilled in the art, and a transgene comprising a mutant copy of the endogenous gene may be introduced into the embryonic stem cell by any of a variety of techniques known to those skilled in the art. In certain embodiments, such a transgene is integrated into the genome of the differentiated motor neuron. In certain embodiments, such a transgene is not integrated into the genome of the differentiated motor neuron.

Conditions Affecting Motor Neuron Differentiation, Development and/or Survival

The present invention encompasses the recognition that proper differentiation, development and/or survival of a cell can be influenced by its environment. For example, non-cell autonomous processes can contribute to the differentiation, development and/or survival of a cell. In certain embodiments, the present invention provides novel system and compositions for studying such non-cell autonomous processes and for identifying factors that mediate such non-cell autonomous processes.

In certain embodiments, methods and compositions of the present invention are used to study non-cell autonomous processes that contribute to the proper differentiation, development and/or survival of a motor neuron. For example, both autonomous defects in motor neurons and toxic non-cell autonomous interactions with other cell types in the spinal cord have been implicated in ALS pathology (Bruijn et al., 2004; Clement et al., 2003; Boillee et al., 1995; Beers, D. R. et al. Wild-type microglia extend survival in PU.1 knockout mice with familial amyotrophic lateral sclerosis. Proc Natl Acad Sci USA 103, 16021-6, 2006). Methods and compositions of the present invention are well suited to the identification and study of factors that mediate non-cell autonomous effects of other cell types on motor neurons, leading to ALS.

Several studies have suggested that cells within the spinal cord may have pathological, non-cell autonomous affects on motor neurons or on the rate of disease progression (Clement et al., 2003; Boillee et al., 2006). However, these studies were of limited utility since they were not able to resolve the identity of cell types that caused these affects and/or were not able to determine whether they acted directly to affect motor neuron survival. The present invention encompasses the discovery and recognition that cultures of ES cell derived motor neurons contain other cell types, including astroglia, and that these ES cell derived cells have a non-cell autonomous affect on motor neuron survival in vitro (see Examples section below). The effects of co-culturing motor neurons with primary glia from SOD1G93A mice and mice expressing the wild-type SOD1 protein were systematically examined. It was discovered that mutant SOD1G93A glia reduced the survival of both wild type and mutant motor neurons. However, the effect was significantly greater on mutant SOD1G93A motor neurons. Therefore, the presently described studies show for the first time that an ALS genotype in glial cells directly and negatively affects the survival of motor neurons and they confirm that there is a cell autonomous component to motor neuron degeneration.

Consistent with the present disclosure, Nagai et al. have shown that primary astrocyte cultures expressing ALS-associated mutant SOD1 proteins contain diffusible factor(s) that are toxic to both primary and ES cell-derived motor neurons (Makiko Nagai, D. B. R., Tetsuya Nagata, Alcmene Chalazonitis, Thomas M. Jessell, Hynek Wichterle, Serge Przedborski. Astrocytes expressing ALS-associated SOD1 mutants release factors selectively toxic to spinal motor neurons. Nature Neuroscience, 2007). In Nagai et al.'s study, motor neurons were the only cell types affected by these mutant glial cells and only SOD1G93A glial cells, not muscle cells or fibroblasts, adversely affected motor neuron survival. Although in Nagai et al's study, mutant primary neurons exhibited morphometric alterations, their survival up to 14 days in culture was indistinguishable from that of their wild-type counterparts. In the presently described studies, differences in survival between wild-type SOD1 and mutant SOD1G93A ES cell-derived motor neurons were observed at 14 and 28 days in culture. The differences between the two studies may originate in the source (embryo or ES cell-derived) or number of the motor neurons used and the timeframe of the investigations.

In certain embodiments, the present invention provides methods for identifying and studying non-cell autonomous factors produced by glial and/or other cells, which factors influence the differentiation, development and/or survival of motor neurons. For example, motor neurons may be cultured in the present of mutant glial cells, and the survival of such motor neurons may be compared to the survival of motor neurons cultured in the presence of wild type glial cells. A difference in survival of motor neurons indicates that a mutation present in such a glial cell is important in mediating proper survival of motor neurons. In certain embodiments, such a mutation in a glial cell results in an alteration in the quantity and/or quality of a protein encoded by a gene in which the mutation is located, which protein may be a factor that contributes to proper survival of motor neurons. In certain embodiments, a mutation in a glial cell results in an alteration in the quantity and/or quality of a protein that is not encoded by gene in which the mutation is located. For example, a mutation may alter the quantity and/or quality of a produced transcription factor, which transcription factor contributes to the proper regulation and/or expression of a second protein, which second protein may be a factor that mediates proper survival of motor neurons. In certain embodiments, a mutation in a glial cell results in an alteration in the quantity and/or quality of a factor that contributes to proper survival of motor neurons, which factor is not a protein (e.g. a small molecule, a lipid, a hormone, etc.). Those of ordinary skill in the art will be aware of a variety of other ways in which a mutation in a particular gene may affect a factor that contributes to the proper survival of motor neurons.

In certain embodiments, embryonic stem cells are induced to differentiate into motor neurons in the presence of glial cells. Such embodiments are useful in the study of normal motor neuron differentiation, development and/or survival, and can be expected to provide useful insights into possible causes, treatments and/or cures of various neurodegenerative diseases.

In certain embodiments, embryonic stem cells are induced to differentiate into motor neurons in the presence of mutant glial cells, and differentiation, development and/or survival of such motor neurons may be compared to differentiation, development and/or survival of motor neurons cultured in the presence of wild type glial cells. A difference in differentiation, development and/or survival of the motor neurons indicates that a mutation present in the glial cell contributes to proper differentiation, development and/or survival of motor neurons. In certain embodiments, a mutation in a glial cell results in an alteration in the quantity and/or quality of a protein encoded by gene in which the mutation is located, which protein is a factor that contributes to proper differentiation, development and/or survival of motor neurons. In certain embodiments, a mutation in a glial cell results in an alteration in the quantity and/or quality of a protein that is not encoded by gene in which the mutation is located. For example, a mutation may alter the quantity and/or quality of a produced transcription factor, which transcription contributes to the proper regulation and/or expression of a second protein, which second protein is a factor that mediates proper differentiation, development and/or survival of motor neurons. In certain embodiments, a mutation in a glial cell results in an alteration in the quantity and/or quality of a factor that is important for proper differentiation, development and/or survival of motor neurons, which factor is not a protein (e.g. a small molecule, a lipid, a hormone, etc.). Those of ordinary skill in the art will be aware of a variety of other ways in which a mutation in a particular gene may affect a factor that is important in the proper survival of motor neurons.

In certain embodiments, mutant glial cells to be used in accordance with the present invention to identify and/or study factors that contribute to proper differentiation, development and/or survival of motor neurons comprise a mutation in a gene associated with a neurodegenerative disease. As but a few non-limiting examples, such a neurodegenerative disease may include ALS, Parkinson's disease, Alzheimer's disease or any number of other neurodegenerative diseases known to those of skill in the art. A variety of genes are known to be associated with neurodegenerative diseases. As one non-limiting example, mutations in the SOD1 gene are known to be associated with the neurodegenerative disease ALS. Thus, in certain embodiments, mutant glial cells to be used in accordance with the present invention to identify and/or study factors that contribute to proper differentiation, development and/or survival of motor neurons comprise a mutation in the SOD1 gene. In humans, Gly92Ala, Ala4Val and Gly37Arg mutations are associated with the onset and progression of ALS. Thus, in certain embodiments, mutant glial cells to be used in accordance with the present invention to identify and/or study factors that contribute to proper differentiation, development and/or survival of motor neurons comprise a SOD1G93A mutation such as Gly92Ala, Ala4Val and/or Gly37Arg. Those of ordinary skill in the art will be aware of a variety of other SOD1 mutant alleles associated with ALS, which mutant alleles can be advantageously used in accordance with one or more of the embodiments described herein.

In certain embodiments, the present invention provides methods for identifying and/or studying non-cell autonomous factors produced by non-glial cells, which factors influence the differentiation, development and/or survival of motor neurons. Non-limiting examples of such non-glial cells that can influence differentiation, development and/or survival of motor neurons include microglial cells, oligodendrocytes, astrocytes, other neuronal cell types in spinal cords (e.g. interneurons) and/or other cells that are in contact with neurons (e.g. muscle cells). Those of ordinary skill in the art will be aware of a variety of other non-glial cells that can influence the differentiation, development and/or survival of motor neurons.

In certain embodiments, methods of the present invention comprise identifying a factor that has a non-cell autonomous effect on survival of a motor neuron. In certain embodiments, such methods comprise providing a motor neuron, identifying a first glial cell, which first glial cell negatively affects survival of the motor neuron, identifying a second glial cell, which second glial cell does not negatively affect survival of the motor neuron, isolating a factor from the either the first or second glial cell, wherein the factor is either: i) a factor from the first glial cell that contributes to the negative effect on survival of the motor neuron; or ii) a factor from the second glial cell that contributes to survival of the motor neuron.

Factors that influence differentiation, development and/or survival can be identified by any of a variety of methods known to those of ordinary skill in the art. In certain embodiments, such a factor is directly identified after determining that a given wild type or mutant cell contributes to proper differentiation, development and/or survival of a cell of interest such as, e.g., a motor neuron. Non-limiting examples of such methods include fractionation, mass spectrometry, protein chip analysis (e.g., if such a factor comprises a protein), chromatography, etc. Those of ordinary skill in the art will be aware of and will be able to employ suitable techniques for directly identifying such a factor.

In certain embodiments, such a factor is identified indirectly. For example, a factor may comprise a protein encoded by a gene. In such embodiments, a gene that encodes such a factor may be identified by any of a variety of techniques such as, for example, differential display, gene chip analysis, RT-PCR, direct sequencing, etc. Those of ordinary skill in the art will be aware of and will be able to employ suitable techniques for identifying such a factor indirectly.

In certain embodiments, a combination of two or more factors may together contribute to differentiation, development and/or survival of a cell of interest such as, for example, a motor neuron. Methods and compositions of the present invention may be advantageously used to identify such a combination of factors.

Disease Modeling and Drug Screening

In certain embodiments, the present invention offers great potential for developing better models for the study of human disease and/or better methods of treatment. In certain embodiments, methods of the present invention employ embryonic stem cells and/or differentiated cells that comprise alterations (e.g., deletions, rearrangements, duplications, substitutions, etc.) in genes associated with a particular disease. In certain embodiments, a disease of interest is a neurodegenerative disease. Exemplary neurodegenerative diseases that can be studied using compositions and methods of the present invention include, but are not limited to, ALS, Parkinson's disease, and Alzheimer's disease. Those skilled in the art will be aware of a number of other neurodegenerative diseases that can be studied using compositions and methods the present invention.

In certain embodiments, a disease of interest is modeled and/or studied by inducing an embryonic stem cell line (that has, for example, been generated by any of the variety of methods of the present invention to contain one or more alterations in one or more genes associated with a disease of interest) to differentiate by culturing such a cell line under appropriate differentiation conditions. For example, an embryonic stem cell line may be generated that contains one or more alterations in one or more genes associated with a neurological degenerative disease, e.g. ALS, or any other neurodegenerative disease of interest. Such an embryonic cell line may be induced to differentiate into motor neurons by subjecting it to appropriate differentiation conditions. Those of ordinary skill in the art will be aware of appropriate differentiation conditions. By observing differentiation, development and/or survival of such a motor neuron and comparing it to differentiation, development and/or survival of a motor neuron derived from an embryonic stem cell line that does not contain the genetic alteration(s) associated with the neurodegenerative disease of interest, the practitioner can achieve a better understanding of the genetic basis of disease progression and pathogenesis.

Additionally or alternatively, an embryonic stem cell line that is generated to contain one or more alterations in one or more genes associated with a disease of interest may be used to screen for agents (e.g., a cell, a small molecule, a hormone, a vitamin, a nucleic acid molecule, an enzyme, an antibody, an amino acid, a virus, etc.) that can be used, for example, in the treatment, prevention and/or cure of that disease. For example, such an embryonic stem cell line may be induced to differentiate into a cell type associated with the disease of interest by placing it under appropriate differentiation conditions. Before, during and/or after differentiation, such a cell may be subjected to a test agent in order to determine whether that agent has an effect on differentiation, development and/or survival of the cell. In certain embodiments, an embryonic stem cell comprising a mutation associated with a neurodegenerative disease is induced to differentiate into a motor neuron, which motor neuron is subjected to an agent before, during and/or after differentiation.

In certain embodiments, compositions and methods of the present invention are useful in studying and/or modeling diseases that to date, have not been amenable to such study and/or modeling. For instance, in many cases, by the time a patient is diagnosed with a particular disease, the early events of disease progression and pathogenesis have already occurred, making it difficult or impossible to determine and track the molecular, cellular, or other changes that occur during the course of the disease. Using inventive methods and compositions disclosed herein, researchers will now be able to determine and study such molecular, cellular, or other changes, leading to a better understanding of disease progression and pointing the way to more effective treatments.

In certain embodiments, methods of the present invention comprise identifying an agent that affects the survival of a SOD1 mutant motor neuron. In certain embodiments, such methods comprise providing a SOD1 mutant motor neuron, providing a test agent, contacting the SOD1 mutant motor neuron with the test agent, and determining the effect of the test agent on survival of the SOD1 mutant motor neuron by comparing the survival of the SOD1 mutant motor neuron to the survival of a control motor neuron lacking the SOD1 mutant allele, which control motor neuron is contacted with the test agent for a period of time and under conditions identical to that of the SOD1 mutant motor neuron. In certain embodiments, a SOD1 motor neuron used in such methods is derived from an embryonic stem cell. In certain embodiments, a SOD1 motor neuron used in such methods comprises a SOD1 mutation associated with a neurodegenerative disease of interest, e.g. ALS.

In certain embodiments, compositions and methods of the present invention are used to study and/or model diseases and/or to screen for agents that can be used in the treatment, prevention and/or cure of diseases, which compositions or methods comprise or make use of human embryonic stem cell lines and/or differentiated cells derived from such human embryonic stem cell lines.

In certain embodiments, compositions and methods of the present invention are used to study and/or model diseases and/or to screen for agents that can be used in the treatment, prevention and/or cure of diseases, which compositions or methods comprise or make use of non-human embryonic stem cell lines and/or differentiated cells derived from such non-human embryonic stem cell lines. Use of non-human stem cell lines and/or differentiated cells derived from them is advantageous when ethical and/or practical limitations prevent the use of human stem cell lines. Non-limiting examples of non-human stem cell lines (and/or differentiated cells derived from them) that may be used in accordance with the present invention to study and/or model diseases and/or to screen for agents that can be used in the treatment, prevention and/or cure of diseases include mouse, rat, and primate stem cell lines. Those of ordinary skill in the art will be aware of a variety of other non-human stem cell lines that will be useful, and those of ordinary skill in the art will be able to generate such stem cell lines by employing one or more methods of the present invention.

Compositions and methods of the present invention may be used to study and/or model of any of a variety of diseases or conditions. Non-limiting examples of such diseases or conditions include childhood congenital malformations, sickle cell anemia, neurological diseases such as amyotrophic lateral sclerosis (also known as Lou Gehrig's disease), Parkinson's disease, Alzheimer's disease or any of a variety of other neurological diseases, Down syndrome (a condition that arises in patients with trisomy for chromosome 21 resulting in dysregulated signaling through the NFAT/calcineurin pathway), etc. One of ordinary skill in the art will be aware of a variety of other disease conditions that may be modeled and/or studied by generating embryonic stem cells according to one or more methods of the present invention.

In certain embodiments, compositions and methods of the present invention comprise or make use of human embryonic stem cell lines and/or differentiated cells derived from a patient suffering from and/or predicted to suffer from a disease of interest. Patient-specific, immune-matched human embryonic stem cells have the potential to be of great biomedical importance for studies of disease and development. For example, certain patients may respond better to a given therapy or drug regimen than other patients. Additionally or alternatively, certain patients may experience fewer and/or less severe side effects after being administered a given therapy or drug regimen than other patients. By utilizing embryonic stem cells that contain the genetic complement of a patient suffering from and/or predicted to suffer from a disease of interest, and permitting such cells to differentiate into a cell type associated with that disease, it will be possible to better predict which therapy or drug regimen will be most beneficial and/or result in the least detrimental side effects.

Furthermore, patient-specific human embryonic stem cells have the potential to be of great biomedical importance for the discovery and/or development of patient-specific agents that can be used to prevent and/or treat a disease of interest. By utilizing embryonic stem cells containing the genetic complement of a patient suffering from a disease of interest, permitting such cells to differentiate into a cell type associated with that disease, and subjecting such cells to one or more test agents before, during and/or after differentiation, discovery and/or development of an agent that will be most beneficial and/or result in the least detrimental side effects for that particular patient will be facilitated. Those of ordinary skill in the art will be able to apply methods and compositions of the present invention to the discovery and/or development of an agent specific for a patient and/or disease of interest.

In certain embodiments, a disease of interest is modeled and/or studied by inducing an embryonic stem cell line to differentiate into a cell type of interest by culturing such a cell line under appropriate differentiation conditions, wherein the embryonic stem cell line is differentiated in the presence of one or more different cell types that contribute to proper differentiation, development and/or survival of the cell type of interest. For example, an embryonic stem cell line containing one or more alterations in one or more genes associated with a neurological degenerative disease, e.g. ALS or any other neurodegenerative disease of interest, may be induced to differentiate into a motor neuron in the presence of one or more glial cells. By observing the differentiation, development and/or survival of such a motor neuron and comparing it to the differentiation, development and/or survival of a motor neuron derived from an embryonic stem cell line that does not contain the genetic alteration(s) associated with the neurodegenerative disease of interest, the practitioner can achieve a better understanding of the genetic basis of disease progression and pathogenesis.

In certain embodiments, an embryonic stem cell line containing a wild type genome is induced to differentiate into a cell type of interest in the presence of one or more different cell types that contribute to proper differentiation, development and/or survival of the cell type of interest. By observing the differentiation, development and/or survival of such a cell type of interest and comparing it to the differentiation, development and/or survival of a cell type of interest in the absence of such different cell types, the practitioner can achieve a better understanding of the genetic basis of normal differentiation, development and/or survival a cell type of interest.

In certain embodiments, a cell type of interest is induced to differentiate in the presence of one or more different cell types that contribute to proper differentiation, development and/or survival of the cell type of interest, wherein the one or more different cell types comprise one or more mutations that affect differentiation, development and/or survival of the cell type of interest. By observing the differentiation, development and/or survival of the cell type of interest in such an environment and comparing it to the differentiation, development and/or survival of a cell type of interest differentiated in the presence of wild type different cell types, the practitioner can achieve a better understanding of non-cell autonomous factors and processes that contribute to proper differentiation, development and/or survival of the cell type of interest.

In certain embodiments, the present invention provides systems and methods for identifying agents (e.g., a cell, a small molecule, a hormone, a vitamin, a nucleic acid molecule, an enzyme, an antibody, an amino acid, a virus, etc.) that can be used, for example, in the treatment, prevention and/or cure of a disease of interest, wherein the differentiation, development and/or survival of a cell type of interest implicated in the onset and/or progression of the disease of interest is influenced by one or more different cell types. For example, such an embryonic stem cell line may be induced to differentiate into a cell type associated with the disease of interest by placing it under appropriate differentiation conditions in the presence of one or more different cell types that contribute to proper differentiation, development and/or survival of the cell type of interest. Before, during and/or after differentiation, such a cell may be subjected to a test agent in order to determine whether that agent has an effect on differentiation, development and/or survival of the cell.

In certain embodiments, an embryonic stem cell comprising a mutation associated with a neurodegenerative disease is induced to differentiate into a motor neuron in the presence of glial cells, which motor neuron is subjected to an agent before, during and/or after differentiation. In certain embodiments, such glial cells are wild type. In certain embodiments, such glial cells comprise one or more mutations that alter the proper differentiation, development and/or survival of the motor neuron. For example, such glial cells may comprise a mutation that induces the motor neuron to display a phenotype characteristic of a disease of interest, such as for example, a neurodegenerative disease including, without limitation, ALS. In certain embodiments, such glial cells comprise a mutation in the SOD1 gene, for example a SOD1G93A mutation. Thus, in certain embodiments, the present invention provides systems and methods for identifying agent(s) that prevent, ameliorate, or reverse the adverse effects of such SOD1G93A mutant glial cells on the proper differentiation, development and/or survival of a motor neuron, including both wild type and mutant motor neurons. In certain embodiments, such identified agents are used to prevent, treat and/or cure ALS.

As described in the Examples herein, it has been discovered that certain genes are overexpressed in glia having a mutation in the SOD1 gene. Moreover, it has been discovered that agents that target such genes or expression products of such genes can promote survival of motor neurons (e.g., motor neurons produced and/or cultured according to a method described herein). Accordingly, in some embodiments, the present invention provides methods of identifying a test agent that modulates survival of a motor neuron, wherein the test agent targets a gene or product of a gene overexpressed in SOD1 mutant glia. In some embodiments, a test agent targets (e.g., inhibits expression or activity of) a gene or product of a gene in Table 2 (e.g., a gene or product of a gene selected from serine (or cysteine) preptidase inhibitor, Glade A, member 1b (Serpina1b); protein tyrosine phosphatase, non-receptor type 7 (Ptpn7); poly (ADP-ribose) polymerase family, member 12 (Zc3hdc1); prostaglandin D2 receptor (Ptgdr); glia maturation factor, beta (Gmfb); ATP-binding cassette, sub-family A (ABC1), member 5 (Abca5); developing brain homeobox 2 (Dbx2); RAB6B, member RAS oncogene family (Rab6b); cut-like 1 (Cutl1); adenosine deaminase (Ada); receptor coactivator 6 interacting protein (Ncoa6ip); interferon-induced protein 35 (ili35); RAB, member of RAS oncogene family-like 2A (Rabl2a); STEAP family member 4 (A1481214); cytoglobin (cygb); Duffy blood group, chemokine receptor (Dfy); chondrolectin (Chodl); neurexin 1 (NRXN1); defensin beta 11 (Defb11); RUN and SH3 domain containing 2 (RUSC2); matrilin-4 (matn4); X-linked lymphocyte-regulated 3A (Xlr3a); C-C motif chemokine 8 (ccl8); T-cell immunoglobulin and mucin domain containing 4 (Timd4); odd-skipped related 2 (osr2); RIKEN cDNA 9130213B05 gene (9130213B05Rik); reversion-inducing-cysteine-rich protein with kazal motifs (Reck); olfactory receptor 116 (Olfr116); protogenin homolog (Prtg; A230098A12Rik); sonic hedgehog (Shh); formyl peptide receptor 1 (Fpr1); pro-platelet basic protein (chemokine (C—X—C motif) ligand 7; CXCL7); DnaJ (Hsp40) homolog, subfamily B, member 3 (DNAJB3); defensin beta 10 (Defb10); apolipoprotein A-II (Apoa2); collagen, type I, alpha 2 (Colla2); islet cell autoantigen 1-like (Ica11; 1700030B17Rik); ATPase, class II, type 9A (Atp9a); chemokine (C-C motif) ligand 5 (CCL5); solute carrier family 39 (zinc transporter), member 14 (Scl39A14); serum amyloid A 3 (Saa3); RIKEN cDNA 3632451O06 gene (3632451006Rik); attractin like 1 (Atrnl1); Alstrom syndrome 1 (Alms1); NK2 homeobox 2 (Nkx2-2); kallikrein related-peptidase 8 (Klk8; Prss19); histone cluster 1, H4k (Hist1h4k); EPH receptor B2 (Ephb2); synaptotagmin XII (Syt12); forkhead box Q1 (Foxq1); splicing factor, arginine/serine-rich 16 (Sfrs16); LanC lantibiotic synthetase component C-like 1 (Lancl1); and MARCKS-like 1 (Mlp)). In some embodiments, a test inhibits expression or activity of a gene or gene product in Table 2 which is involved in inflammation. In some embodiments, a test agent inhibits expression or activity of a prostaglandin D receptor.

In certain embodiments, a test agent that inhibits expression or activity of a gene or product of a gene in Table 2 includes a small molecule, an antibody, a hormone, a vitamin, a nucleic acid molecule, an enzyme, an amino acid, and/or a virus.

In certain embodiments, a test agent is a nucleic acid molecule, e.g., a nucleic acid molecule that mediates RNA interference. RNA interference refers to sequence-specific inhibition of gene expression and/or reduction in target RNA levels mediated by an at least partly double-stranded RNA, which RNA comprises a portion that is substantially complementary to a target RNA. Typically, at least part of the substantially complementary portion is within the double stranded region of the RNA. In some embodiments, RNAi can occur via selective intracellular degradation of RNA. In some embodiments, RNAi can occur by translational repression. In some embodiments, RNAi agents mediate inhibition of gene expression by causing degradation of target transcripts. In some embodiments, RNAi agents mediate inhibition of gene expression by inhibiting translation of target transcripts. Generally, an RNAi agent includes a portion that is substantially complementary to a target RNA. In some embodiments, RNAi agents are at least partly double-stranded. In some embodiments, RNAi agents are single-stranded. In some embodiments, exemplary RNAi agents can include small interfering RNA (siRNA), short hairpin RNA (shRNA), and/or microRNA (miRNA). In some embodiments, an agent that mediates RNAi includes a blunt-ended (i.e., without overhangs) dsRNA that can act as a Dicer substrate. For example, such an RNAi agent may comprise a blunt-ended dsRNA which is >25 base pairs length. RNAi mechanisms and the structure of various RNA molecules known to mediate RNAi, e.g. siRNA, shRNA, miRNA and their precursors, are described, e.g., in Dykxhhorn et al., 2003, Nat. Rev. Mol. Cell. Biol., 4:457; Hannon and Rossi, 2004, Nature, 431: 3761; and Meister and Tuschl, 2004, Nature, 431:343; all of which are incorporated herein by reference.

In some embodiments, a nucleic acid that mediates RNAi includes a 19 nucleotide double-stranded portion, comprising a guide strand and an antisense strand. Each strand has a 2 nt 3' overhang. Typically the guide strand of the siRNA is perfectly complementary to its target gene and mRNA transcript over at least 17-19 contiguous nucleotides and typically the two strands of the siRNA are perfectly complementary to each other over the duplex portion. However, as will be appreciated by one of ordinary skill in the art, perfect complementarity is not required. Instead, one or more mismatches in the duplex formed by the guide strand and the target mRNA is often tolerated, particularly at certain positions, without reducing the silencing activity below useful levels. For example, there may be 1, 2, 3, or even more mismatches between the target mRNA and the guide strand (disregarding the overhangs).

Molecules having the appropriate structure and degree of complementarity to a target gene will exhibit a range of different silencing efficiencies. A variety of additional design criteria have been developed to assist in the selection of effective siRNA sequences. Numerous software programs that can be used to choose siRNA sequences that are predicted to be particularly effective to silence a target gene of choice are available (see, e.g., Yuan et al., 2004, Nuc. Acid. Res., 32:W130; and Santoyo et al., 2005, Bioinformatics, 21:1376; both of which are incorporated herein by reference). Modifications that increase stability and resistance to nuclease breakdown are well known to one skill in the art and are contemplated.

As will be appreciated by one of ordinary skill in the art, RNAi may be effectively mediated by RNA molecules having a variety of structures that differ in one or more respects from that described above. For example, the length of the duplex can be varied (e.g., from about 17-29 nucleotides); the overhangs need not be present and, if present, their length and the identity of the nucleotides in the overhangs can vary (though most commonly symmetric dTdT overhangs are employed in synthetic siRNAs).

In certain embodiments, the present invention provides methods of modulating survival of a motor neuron by contacting a motor neuron (in vitro or in vivo) with an agent that reduces the expression or activity of a prostaglandin D receptor. Agents that reduce expression or activity (e.g., antagonize) prostaglandin D receptors include MK 0524 ((3R)-4-(4-chlorobenzyl)-7-fluoro-5-(methylsulfonyl)-1,2,3,4-tetrahydrocyclopenta[b]indol-3-yl]-acetic acid; Sturino et al., J. Med. Chem. 50(4):794-806, 2007) and analogs thereof, and compounds disclosed in Mitsumori et al., Curr. Pharm. Des., 10(28):3533-8, 2004; Beaulieu et al., Bioorg Med Chem. Lett. 18(8):2696-700, 2008; Torisu et al., Eur J Med. Chem. 40(5):505-19, 2005; U.S. Pat. Pub. Nos. 20010051624, 20030055077, 20040180934, 20070244131, 20070265278, 20070265291, 20080194600, and U.S. Pat. No. 7,153,852.

Human Stem Cells and Cells Derived from Them

Although mouse genetics has provided a sophisticated understanding of the cellular and molecular mechanisms that contribute to familial ALS, it cannot inform us as to the actual relevance of its findings to human patients. In fact, due to the fundamental differences between human and mouse physiology, many observations made in mouse disease models have not translated well to human experimental systems or to the clinic. For example, diabetes has been "cured" many times over in the NOD mouse model of disease. However, few of the observations and experimental therapies developed in this mouse model have proven relevant to the human disease (Shoda, L. K. et al. A comprehensive review of interventions in the NOD mouse and implications for translation. *Immunity*. 23, 115-26, 2005). Similarly, mutations in the RB gene that lead to Retinoblastoma in human patients cause an independent range of tumors in mice carrying the same genetic lesion (Goodrich, D. W. Lee, W. H. Molecular characterization of the retinoblastoma susceptibility gene. *Biochim Biophys Acta*. 1155, 43-61, 1993; Williams B. O. et al. Extensive contribution of Rb-deficient cells to adult chimeric mice with limited histopathological consequences. *EMBO J.*, 13, 4251-9, 1994). As a result many therapeutics developed in animal, or based on drug-targets discovered in animal models, fail in clinical trials (Shoda et al., 2005; Gawarylewski, A. The trouble with animal models. *The Scientist*. 21 (7), 45-51, 2007; Rubin, L. L. Stem cells and drug discovery: the beginning of a new era? *Cell*. 132, 549-52, 2008). The cost of these failures is substantial (Gawarylewski et al., 2007; Rubin, 2008).

Considerable time, effort and expense would be saved if fundamental observations made in animal models could be routinely validated in the relevant human cell types. A potential solution is to use human embryonic stem cells as a renewable source of these cells for the study of disease and for drug target validation. The discoveries described herein have demonstrated the usefulness of motor neurons derived from human ES cells in validating findings from mouse models of ALS (see e.g., Examples 7 and 8 below). It has been found that glia cells over-expressing the SOD1G93A mutation negatively affect the viability of human ES cell derived motor neurons in a time dependent manner. Such non-cell autonomous effect of glia is specific for motor neurons, as it does not seem interfere with the survival of human interneurons.

In certain embodiments, in vitro model systems of the present invention utilize human motor neurons derived from human ES cells. In certain embodiments, a human motor neuron differentiated from a human embryonic stem cell comprises a mutation in a gene associated with neurodegenerative disease. As non-limiting examples, such a neurodegenerative disease may include ALS, Parkinson's disease, Alzheimer's disease or any number of other neurodegenerative diseases known to those of skill in the art. A variety of genes are known to be associated with neurodegenerative diseases. As one non-limiting example, mutations in the SOD1 gene are known to be associated with the neurodegenerative disease ALS. For example, in humans, Gly92Ala, Ala4Val and Gly37Arg mutations are associated with the onset and progression of ALS. Those of ordinary skill in the art will be aware of other SOD1 mutations associated with ALS. In certain embodiments, compositions and method of the present invention comprise or employ human motor neurons comprising a SOD1G93A mutation such as Gly92Ala, Ala4Val and/or Gly37Arg.

In certain embodiments, in vitro model systems of the present invention comprising human motor neurons may be advantageously employed for the human physiological validation of findings from animal models, such as, without limitation, animal models (e.g., mouse) that recapitulate in whole or in part neurodegenerative diseases such as ALS and/or other neurodegenerative diseases.

In certain embodiments, in vitro model systems of the present invention comprising human motor neurons may be advantageously employed to identify novel factors, agents, etc. that affect motor neuron development and/or contribute to a disease state, such as, without limitation, a neurodegenerative disease, e.g. ALS, in the absence of an animal model. In certain embodiments, in vitro model systems of the present invention comprising human motor neurons may be advantageously employed to illuminate the target, efficacy, toxicity, mode of action, etc. of factors, agents, etc. that affect motor neuron development and/or contribute to a disease state, such as, without limitation, a neurodegenerative disease, e.g. ALS.

In certain embodiments, methods of the present invention employ human mutant motor neurons that comprise a mutation in a gene associated with a neurodegenerative disease, for example ALS. One non-liming example of a gene associated with the neurodegenerative disease ALS is SOD1. A variety of SOD1 mutant alleles are known to be associated with ALS, including without limitation, SOD1G93A. In certain embodiments, methods of the present invention utilize human motor neurons comprising a SOD1 mutant allele (e.g., SOD1G93A) to screen for test agents that affect motor neuron differentiation, development and/or survival. In certain embodiments, methods of the present invention comprise using such SOD1 mutant motor neurons to identify a factor that has a non-cell autonomous effect on the differentiation, development and/or survival of a motor neuron.

In certain embodiments, methods of the present invention employ human mutant cells that are not motor neurons, which mutant cells comprise a mutation in a gene associated with a neurodegenerative disease, for example ALS. As but one non-limiting example, certain methods the present invention employ glial cells comprising a mutation in a gene associated with a neurodegenerative disease such as ALS. In certain embodiments, methods the present invention employ glial cells comprising a mutation in a SOD1 gene, such as, without limitation, SOD1G93A.

Those skilled in the art will be aware of other gene mutations associated with neurodegenerative diseases, and will be able to use methods and compositions described herein to validate results of animal models, to identify novel factors, agents, etc. that affect motor neuron development and/or contribute to a disease state, and/or to illuminate the target, efficacy, toxicity, mode of action, etc. of factors, agents, etc. that affect motor neuron development and/or contribute to a disease state.

Non-Human Applications

Embryonic stem cells of the present invention and/or cells derived from them can be advantageously used in the study and/or modeling of human diseases, although one of ordinary skill in the art will understand that the present disclosure is not limited to human applications. Thus, for example, non-human embryonic stem cell lines may be used in the study and/or modeling of diseases associated with pets (e.g., cats, dogs, rodents, etc.) as well as commercially important domestic animals (e.g., cows, sheep, pigs, etc.). Additionally or alternatively, non-human embryonic stem cell lines may be used to screen for agents that can be used in the prevention and/or treatment of diseases associated with pets and/or commercially important domestic animals.

Motor Neuron Disease

The motor neuron diseases (MND) are a group of neurological disorders that selectively affect motor neurons, the nerve cells that control voluntary muscle activity including speaking, walking, breathing, swallowing and general movement of the body. Skeletal muscles are innervated by a group of neurons (lower motor neurons) located in the ventral horns of the spinal cord which project out the ventral roots to the muscle cells. These nerve cells are themselves innervated by the corticospinal tract or upper motor neurons that project from the motor cortex of the brain. On macroscopic pathology, there is a degeneration of the ventral horns of the spinal cord, as well as atrophy of the ventral roots. In the brain, atrophy may be present in the frontal and temporal lobes. On microscopic examination, neurons may show spongiosis, the presence of astrocytes, and a number of inclusions including characteristic "skein-like" inclusions, bunina bodies, and vacuolisation. Motor neuron diseases are varied and destructive in their effect. They commonly have distinctive differences in their origin and causation, but a similar result in their outcome for the patient: severe muscle weakness. Amyotrophic lateral sclerosis (ALS), primary lateral sclerosis (PLS), progressive muscular atrophy (PMA), pseudobulbar palsy, progressive bulbar palsy, spinal muscular atrophy (SMA) and post-polio syndrome are all examples of MND. The major site of motor neuron degeneration classifies the disorders. Common MNDs include amyotrophic lateral sclerosis, which affects both upper and lower motor neurons. Progressive bulbar palsy affects the lower motor neurons of the brain stem, causing slurred speech and difficulty chewing and swallowing. Individuals with these disorders almost always have abnormal signs in the arms and legs. Primary lateral sclerosis is a disease of the upper motor neurons, while progressive muscular atrophy affects only lower motor neurons in the spinal cord. Means for diagnosing MND are well known to those skilled in the art. Non limiting examples of symptoms are described below.

Amyotrophic lateral sclerosis (ALS), also called Lou Gehrig's disease or classical motor neuron disease, is a progressive, ultimately fatal disorder that eventually disrupts signals to all voluntary muscles. In the United States, doctors use the terms motor neuron disease and ALS interchangeably. Both upper and lower motor neurons are affected. Approximately 75 percent of people with classic ALS will also develop weakness and wasting of the bulbar muscles (muscles that control speech, swallowing, and chewing). Symptoms are usually noticed first in the arms and hands, legs, or swallowing muscles. Muscle weakness and atrophy occur disproportionately on both sides of the body. Affected individuals lose strength and the ability to move their arms, legs, and body. Other symptoms include spasticity, exaggerated reflexes, muscle cramps, fasciculations, and increased problems with swallowing and forming words. Speech can become slurred or nasal. When muscles of the diaphragm and chest wall fail to function properly, individuals lose the ability to breathe without mechanical support. Although the disease does not usually impair a person's mind or personality, several recent studies suggest that some people with ALS may have alterations in cognitive functions such as problems with decision-making and memory. ALS most commonly strikes people between 40 and 60 years of age, but younger and older people also can develop the disease. Men are affected more often than women. Most cases of ALS occur sporadically, and family members of those individuals are not considered to be at increased risk for developing the disease. However, there is a familial form of ALS in adults, which often results from mutation of the superoxide dismutase gene, or SOD1, located on chromosome 21. In addition, a rare juvenile-onset form of ALS is genetic. Most individuals with ALS die from respiratory failure, usually within 3 to 5 years from the onset of symptoms. However, about 10 percent of affected individuals survive for 10 or more years.

Progressive bulbar palsy, also called progressive bulbar atrophy, involves the bulb-shaped brain stem—the region that controls lower motor neurons needed for swallowing, speaking, chewing, and other functions. Symptoms include pharyngeal muscle weakness (involved with swallowing), weak jaw and facial muscles, progressive loss of speech, and tongue muscle atrophy. Limb weakness with both lower and upper motor neuron signs is almost always evident but less prominent. Affected persons have outbursts of laughing or crying (called emotional lability). Individuals eventually become unable to eat or speak and are at increased risk of choking and aspiration pneumonia, which is caused by the passage of liquids and food through the vocal folds and into the lower airways and lungs. Stroke and myasthenia gravis each have certain symptoms that are similar to those of progressive bulbar palsy and must be ruled out prior to diagnosing this disorder. In about 25 percent of ALS cases early symptoms begin with bulbar involvement. Some 75 percent of individuals with classic ALS eventually show some bulbar involvement. Many clinicians believe that progressive bulbar palsy by itself, without evidence of abnormalities in the arms or legs, is extremely rare.

Pseudobulbar palsy, which shares many symptoms of progressive bulbar palsy, is characterized by upper motor neuron degeneration and progressive loss of the ability to speak, chew, and swallow. Progressive weakness in facial muscles leads to an expressionless face. Individuals may develop a gravelly voice and an increased gag reflex. The tongue may become immobile and unable to protrude from the mouth. Individuals may also experience emotional lability.

Primary lateral sclerosis (PLS) affects only upper motor neurons and is nearly twice as common in men as in women. Onset generally occurs after age 50. The cause of PLS is unknown. It occurs when specific nerve cells in the cerebral cortex (the thin layer of cells covering the brain which is responsible for most higher level mental functions) that control voluntary movement gradually degenerate, causing the muscles under their control to weaken. The syndrome—which scientists believe is only rarely hereditary—progresses gradually over years or decades, leading to stiffness and clumsiness of the affected muscles. The disorder usually affects the legs first, followed by the body trunk, arms and hands, and, finally, the bulbar muscles. Symptoms may include difficulty with balance, weakness and stiffness in the legs, clumsiness, spasticity in the legs which produces slowness and stiffness of movement, dragging of the feet (leading to an inability to walk), and facial involvement resulting in dysarthria (poorly articulated speech). Major differences between ALS and PLS (considered a variant of ALS) are the motor neurons involved and the rate of disease progression. PLS may be mistaken for spastic paraplegia, a hereditary disorder of the upper motor neurons that causes spasticity in the legs and usually starts in adolescence. Most neurologists follow the affected individual's clinical course for at least 3 years before making a diagnosis of PLS. The disorder is not fatal but may affect quality of life. PLS often develops into ALS.

Progressive muscular atrophy (PMA) is marked by slow but progressive degeneration of only the lower motor neurons. It largely affects men, with onset earlier than in other MNDs. Weakness is typically seen first in the hands and then spreads into the lower body, where it can be severe. Other symptoms may include muscle wasting, clumsy hand movements, fasciculations, and muscle cramps. The trunk muscles and respiration may become affected. Exposure to cold can worsen symptoms. The disease develops into ALS in many instances.

Spinal muscular atrophy (SMA) is a hereditary disease affecting the lower motor neurons. Weakness and wasting of the skeletal muscles is caused by progressive degeneration of the anterior horn cells of the spinal cord. This weakness is often more severe in the legs than in the arms. SMA has various forms, with different ages of onset, patterns of inheritance, and severity and progression of symptoms. Some of the more common SMAs are described below.

SMA type I, also called Werdnig-Hoffmann disease, is evident by the time a child is 6 months old. Symptoms may include hypotonia (severely reduced muscle tone), diminished limb movements, lack of tendon reflexes, fasciculations, tremors, swallowing and feeding difficulties, and impaired breathing. Some children also develop scoliosis (curvature of the spine) or other skeletal abnormalities. Affected children never sit or stand and the vast majority usually die of respiratory failure before the age of 2.

Symptoms of SMA type II usually begin after the child is 6 months of age. Features may include inability to stand or walk, respiratory problems, hypotonia, decreased or absent tendon reflexes, and fasciculations. These children may learn to sit but do not stand. Life expectancy varies, and some individuals live into adolescence or later.

Symptoms of SMA type III (Kugelberg-Welander disease) appear between 2 and 17 years of age and include abnormal gait; difficulty running, climbing steps, or rising from a chair; and a fine tremor of the fingers. The lower extremities are most often affected. Complications include scoliosis and joint contractures—chronic shortening of muscles or tendons around joints, caused by abnormal muscle tone and weakness, which prevents the joints from moving freely.

Symptoms of Fazio-Londe disease appear between 1 and 12 years of age and may include facial weakness, dysphagia (difficulty swallowing), stridor (a high-pitched respiratory sound often associated with acute blockage of the larynx), difficulty speaking (dysarthria), and paralysis of the eye muscles. Most individuals with SMA type III die from breathing complications.

Kennedy disease, also known as progressive spinobulbar muscular atrophy, is an X-linked recessive disease. Daughters of individuals with Kennedy disease are carriers and have a 50 percent chance of having a son affected with the disease. Onset occurs between 15 and 60 years of age. Symptoms include weakness of the facial and tongue muscles, hand tremor, muscle cramps, dysphagia, dysarthria, and excessive development of male breasts and mammary glands. Weakness usually begins in the pelvis before spreading to the limbs. Some individuals develop noninsulin-dependent diabetes mellitus.

The course of the disorder varies but is generally slowly progressive. Individuals tend to remain ambulatory until late in the disease. The life expectancy for individuals with Kennedy disease is usually normal.

Congenital SMA with arthrogryposis (persistent contracture of joints with fixed abnormal posture of the limb) is a rare disorder. Manifestations include severe contractures, scoliosis, chest deformity, respiratory problems, unusually small jaws, and drooping of the upper eyelids.

Post-polio syndrome (PPS) is a condition that can strike polio survivors decades after their recovery from poliomyelitis. PPS is believed to occur when injury, illness (such as degenerative joint disease), weight gain, or the aging process damages or kills spinal cord motor neurons that remained functional after the initial polio attack. Many scientists believe PPS is latent weakness among muscles previously affected by poliomyelitis and not a new MND. Symptoms include fatigue, slowly progressive muscle weakness, muscle atrophy, fasciculations, cold intolerance, and muscle and joint pain. These symptoms appear most often among muscle groups affected by the initial disease. Other symptoms include skeletal deformities such as scoliosis and difficulty breathing, swallowing, or sleeping. Symptoms are more frequent among older people and those individuals most severely affected by the earlier disease. Some individuals experience only minor symptoms, while others develop SMA and, rarely, what appears to be, but is not, a form of ALS. PPS is not usually life threatening. Doctors estimate the incidence of PPS at about 25 to 50 percent of survivors of paralytic poliomyelitis.

Prostaglandin D2 Receptors

There are two identified PGD2 receptors: PGD2 receptor 1 (often known as the classic PGD2 receptor, is also called AS1, DP1, DP, ASRT1, MGC49004, PTGDR) and G protein-coupled receptor 44 or "chemoattractant receptor-homologous molecule expressed on TH2 cells" (also known as DP2, CD294, GPR44, and CRTH2). Both are G protein-coupled 7-transmembrane receptors but there are distinct differences between these two receptors with respect to their gene encoding the receptor, cell expression and signaling responses to ligands.

The human gene for the prostaglandin D2 receptor DP1 (NM_000953.2; NP_000944.1; NCBI Entrez GeneID: 5729) is located on chromosome 14 and it encodes a G-protein-coupled protein 7-transmembrane receptor that has been shown to function as a prostanoid DP receptor. The activity of this receptor is mainly mediated by G-stimulatory proteins that stimulate adenylate cyclase with an elevation of intracellular cAMP and $Ca^{2+}$ but without an observed increase in IP3. On the other hand, the human gene for the prostaglandin D2 receptor CRTH2 (NM_004778.2; NP_004769.2; NCBI Entrez GeneID: 11251) is located on chromosome 11 and it encodes a G-protein-coupled protein 7-transmembrane receptor. The activity of this receptor is mainly mediated by G-inhibitory proteins.

In normal subjects, DP2 is selectively expressed by T helper 2 cells but not T helper 1 cells among circulating CD4+ lymphocytes. DP2 does not mediate Nicotinic acid (NA)-induced vasodilation; the DP2-specific agonist DK-PGD2 (13,14-dihydro-15-keto-PGD2) did not induce cutaneous vasodilation, and $DP2^{-/-}$ mice have a normal vasodilatory response to NA. By contrast, BW245C, a DP1-selective agonist, induced vasodilation in mice, and MK-0524, a DP1-selective antagonist, blocked both PGD2- and NA-induced vasodilation.

In response to the ligand prostaglandin D2, DP1 induces $Ca^{2+}$ influx and cAMP generation through Gαs-type G protein, which leads to vasodilation, relavation of smooth muscles, and inhibition of dendritic cell migration. In contrast, CRTH2 is coupled with Gαi-type G protein and induces cell migration in eosinophil, basophils, and TH2 lines.

Several literatures have indicated that activation and signaling through the classic DP1 receptor provides neuroprotection for motor neurons in organotypic models of ALS (Liejun Wu, et al, 2007, Neurasci. Letts. 421:253-258); provides neuroprotection against glutamate toxicity in cultured hippocampal neurons and organotypic slices while activation of CRTH2 promoted neuron loss (Liang X., et al., 2005, J. Neurochem. 92:477-486); and provides neuroprotection against ischemia-reperfusion injury in primary cultures of corticostriatal neurons (Sofiyan Saleem, et al., 2007, Eur. J. Neurosci. 26:73-78).

Inhibition of the Expression and/Activity of Prostaglandin D2 DP1 Receptor

In some embodiments, the methods of neuroprotecting motor neurons, promoting survival of motor neurons and/or treating of motor neuron diseases comprise preventing, blocking, stopping, and/or reducing the activation and signaling from the classic prostaglandin D2 receptor, DP1 by way of an inhibitor.

Embodiments of the invention also provide methods for increasing motor neuron survival in a subject with motor neuron disease comprising administering to a subject an inhibitor of expression and/or activity of the prostaglandin D2 DP1 receptor.

In some embodiments, the inhibitor is selected from the group consisting of: a small molecule, a nucleic acid molecule, a protein, e.g. an activity-blocking antibody, and combinations thereof.

In one embodiment, the inhibitor functions by inhibiting, preventing, blocking, stopping, and/or reducing the expression of the DP1 and the inhibitor is selected from a small molecule and a nucleic acid. Such an inhibitor of DP1 expression would reduce the mRNA or protein level of DP1 by at least 20%, at least 30%, at least 40%, at least 50%, at least 60%, at least 70%, at least 80%, at least 90%, at least 100%, including all the percentages between 20% to 100%. The changes in mRNA or protein level can be assessed by any method known to one skilled in the art, e.g. quantitative RT-PCR to determine the mRNA synthesized and Western Blot analysis for determining the protein amount. Antibodies against the human DP1 are commercially available, e.g. at ABNOVA Catalog #: H00005729-B01P. In a preferred embodiment, the inhibitor is a nucleic acid comprising a DP1 (human PTGDR) specific RNA interference agent or a vector encoding a human PTGDR specific RNA interference agent. In a some embodiment, the RNA interference agent comprises one or more of the nucleotide sequences of the following sequences:

| | |
|---|---|
| ACAGGACCUCUGAAGAAGCtt; | (SEQ ID NO: 7) |
| AUAUGACCAGGUCAGGCAGtt; | (SEQ ID NO: 8) |
| GGGUGUCAGUAGGAAUCAAtt; | (SEQ ID NO: 9) |
| CCAGUGUGUGACUCACUGUtt; | (SEQ ID NO: 10) |

```
AGCCCACCCAGGACUUAGCtt;      (SEQ ID NO: 11)

ACGCAGCUGCAACUGAAGCtt.      (SEQ ID NO: 12)
```

Alternatively, specific RNA interference agent for the human PTGDR or a vector encoding a human PTGDR specific RNA interference agent such as siRNA and shRNA reagents against the human PTGDR are commercially obtainable from INVITROGEN Inc., STEALTH SELECT RNAi™ siRNA (Catalog#1299003 for the set of three oligos); or single oligos (cat. Log # HSS108762; HSS108763; HSS108764); Applied Biosystems SILENCER® siRNAs: NM_000953; ABNOVA.

In one embodiment, the inhibitor functions by inhibiting, preventing, blocking, stopping, and/or reducing DP1 signaling activity. The inhibitor is an antagonist of the DP1 receptor and is selected from the group consisting of an activity-blocking antibody against DP1, an antibody against the ligand prostaglandin D2 (i.e. an anti-PGD2 antibody), an antigen-binding fragment thereof of any of the described antibodies or a small molecule antagonist of the DP1 receptor.

In one embodiment, antibodies that specifically bind DP1 or PGD2 can be used for the inhibition of the DP1 signaling in vivo. Antibodies to DP1 are commercially available (e.g. ABNOVA, Catalog #: H00005729-B01P) and can be raised by one of skill in the art using well known methods, e.g. as disclosed in PCT publication WO 97/40072 or U.S. Application. No. 2002/0182702, which are herein incorporated by reference. The processes of immunization to elicit antibody production in a mammal, the generation of hybridomas to produce monoclonal antibodies, and the purification of antibodies may be performed by described in "Current Protocols in Immunology" (CPI) (John Wiley and Sons, Inc.) and Antibodies: A Laboratory Manual (Ed Harlow and David Lane editors, Cold Spring Harbor Laboratory Press 1988) which are both incorporated by reference herein in their entireties; Brown, "Clinical Use of Monoclonal Antibodies," in. The DP1 inhibitory activity of a given antibody, or, for that matter, any DP1 inhibitor, can be assessed using methods known in the art or described herein—to avoid doubt, an antibody that inhibits DP1 activity will cause a decrease in cAMP production and $Ca^{2+}$ influx in the presence of an activity-blocking antibody compared to in the absence of such an antibody. Biochemical assays for determining DP1 (PTGDR) activity are available from INVITROGEN™ Inc., MILLIPORE®, R&D Systems and BIOMOL® to name a few. A decrease in in cAMP production, $Ca^{2+}$ influx and/or DP1 signaling activity is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower or more in the presence of the anti-DP1 antibody, anti-PGD2 antibody, and/or inhibitor of DP1 activity, including the percentages in between herein disclosed, compared to control which is in the absence of any DP1 antibody, PGD2 antibody, and/or DP1 activity inhibitor.

Antibody inhibitors of DP1 or PGD2 can include polyclonal and monoclonal antibodies and antigen-binding derivatives or fragments thereof. Well known antigen binding fragments include, for example, single domain antibodies (dAbs; which consist essentially of single VL or VH antibody domains), Fv fragment, including single chain Fv fragment (scFv), Fab fragment, and F(ab')2 fragment. Methods for the construction of such antibody molecules are well known in the art.

In one embodiment, the inhibitor of DP1 activity interferes with DP1 interaction with its ligand PGD2, e.g. an anti-PGD2 antibody which serves to sequester the PGD2 away from the receptor and thus prevent any signaling from the receptor. Anti-PGD2 antibodies are commercially available, e.g. at BIOMOL® Cat. #905-047. An anti-DP1 antibody also serves to interfere with DP1 receptor interaction with its ligand PGD2, especially when the antibody binds to the extracellular PGD2-binding region of the receptor. The extracellular regions are found on amino acids 1-19, 85-103, 169-193 and 288-307 of the 360 amino acid residue of the human DP1 protein.

In one embodiment, the inhibitor of DP1 activity is a small molecule antagonist of PGD2 DP1 receptor function. Examples include but are not limited to: MK-0524, BWA868C, ONO-4127Na, resveritrol, the 2,6-substituted-4-mono substituted amino-pyrimidine compounds described in WO/2007/121280 and the 2-phenyl-indole compounds described in US 2009176804 and WO 2008014186. Resveritrol is a natural compound found in grapes, mulberries, peanuts, and other plants or food products, especially red wine that may protect against cancer and cardiovascular disease by acting as an antioxidant, anti-mutagen, and anti-inflammatory. Other antagonists are described in US 2005/0215609, WO 2005/079793, and WO 2001/078697, all the patent applications are hereby incorporated by reference in their entirety.

Administration and Formulations

In one embodiment, the methods described herein comprise administering a pharmaceutical composition comprising of an inhibitor of a prostaglandin D2 DP1 receptor, including anti-DP1 antibody, anti-PGD2 antibody, DP1 specific RNA interfering agents, MK-0524, BWA868C, ONO-4127Na, resveritrol and other DP1 antagonists, and a pharmaceutically acceptable carrier or diluent. In one embodiment, the pharmaceutical composition is administered by injection, infusion, instillation, or ingestion. The pharmaceutical compositions of the invention are administered in a therapeutically effective amount.

As used herein, the term "pharmaceutically acceptable", and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. Each carrier must also be "acceptable" in the sense of being compatible with the other ingredients of the formulation. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. The pharmaceutical formulation contains a compound of the invention in combination with one or more pharmaceutically acceptable ingredients. The carrier can be in the form of a solid, semi-solid or liquid diluent, cream or a capsule. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the invention that will be effective in the treatment of a particular disorder or condition will depend on the nature of the disorder or condition, and can be determined by standard clinical techniques. The phrase "pharmaceutically acceptable carrier or diluent" means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body.

As used herein, "administered" refers to the placement of an inhibitor of a prostaglandin D2 DP1 receptor, into a subject by a method or route which results in at least partial localization of the inhibitor at a desired site. An inhibitor of a prostaglandin D2 DP1 receptor, including anti-DP1 antibody, anti-PCD2 antibody, DP1 specific RNA interfering agents, MK-0524, BWA868C, ONO-4127Na, resveritrol and other small molecule DP1 antagonists, can be administered by any appropriate route which results in effective treatment in the subject, i.e. administration results in delivery to a desired location in the subject where at least a portion of the composition delivered, i.e. at least one inhibitor of DP1, is active in the desired site for a period of time. The period of time the inhibitor is active depends on the half life in vivo after administration to a subject, and can be as short as a few hours, e.g. twenty-four hours, to a few days, to as long as several years. Modes of administration include injection, infusion, instillation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion.

Inhibitor(s) of a prostaglandin D2 DP1 receptor, including anti-DP1 antibody, anti-PCD2 antibody, DP1 specific RNA interfering agents, MK-0524, BWA868C, ONO-4127Na, resveritrol and other DP1 antagonists, can be employed, either alone or in combination with one or more other therapeutic agents, e.g. administered as a "cocktail" formulation with other therapeutics typically prescribed for MND, e.g. riluzole, massage, aromatherapy and reflexology. The administration can be a coordinated administration for simultaneous, sequential or separate use, of one or more inhibitors of the invention together with one or more other active therapeutics.

Inhibitor(s) of a prostaglandin D2 DP1 receptor, including anti-DP1 antibody, anti-PCD2 antibody, DP1 specific RNA interfering agents, MK-0524, BWA868C, ONO-4127Na, resveritrol and other DP1 antagonists can be administered either as the sole active therapeutic or in a coordinated regime with one or more other therapeutics can be administered by a variety of routes, such as orally or by injection, e.g., intramuscular, intraperitoneal, subcutaneous or intravenous injection, or topically such as transdermally, vaginally and the like. Small molecule inhibitors surh as the pyrrolidine inhibitor compounds can be suitably administered to a subject in the protonated and water-soluble form, e.g., as a pharmaceutically acceptable salt of an organic or inorganic acid, e.g., hydrochloride, sulfate, hemi-sulfate, phosphate, nitrate, acetate, oxalate, citrate, maleate, mesylate, etc. If the compound has an acidic group, e.g., a carboxy group, base addition salts may be prepared. Lists of additional suitable salts may be found, e.g., in Part 5 of Remington's Pharmaceutical Sciences, 20th Edition, 2000, Marck Publishing Company, Easton, Pa.

Inhibitor(s) of a prostaglandin D2 DP1 receptor, including anti-DP1 antibody, anti-PCD2 antibody, DP1 specific RNA interfering agents, MK-0524, BWA868C, ONO-4127Na, resveritrol and other DP1 antagonists can be employed, either alone or in combination with one or more other therapeutic agents as discussed above, as a pharmaceutical composition in a mixture with conventional excipients, i.e., pharmaceutically acceptable organic or inorganic carrier substances suitable for oral, parenteral, enteral or topical application which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

For oral administration, pharmaceutical compositions containing Inhibitor(s) of a prostaglandin D2 DP1 receptor, including anti-DP1 antibody, anti-PCD2 antibody, DP1 specific RNA interfering agents, MK-0524, BWA868C, ONO-4127Na, resveritrol and other DP1 antagonists, can be formulated as e.g., tablets, troches, lozenges, aqueous or oily suspensions, dispersible powders or granules, emulsions, hard or soft capsules, syrups, elixers and the like. Typically suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

For parenteral application, e.g., sub-cutaneous, intraperitoneal or intramuscular, particularly suitable are solutions, preferably oily or aqueous solutions as well as suspensions, emulsions, or implants, including suppositories. Ampules are convenient unit dosages. It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines. See also Remington's Pharmaceutical Sciences, supra. In general, a suitable effective dose of one or more 1,2-substituted 5-pyrrolidinone compounds of the invention, particularly when using the more potent compound (s) of the invention, will be in the range of from 0.01 to 100 milligrams per kilogram of bodyweight of recipient per day, preferably in the range of from 0.01 to 20 milligrams per kilogram bodyweight of recipient per day, more preferably in the range of 0.05 to 4 milligrams per kilogram bodyweight of recipient per day. The desired dose is suitably administered once daily, or several subdoses, e.g., 2 to 4 sub-doses, are administered at appropriate intervals through the day, or other appropriate schedule. Such sub-doses may be administered as unit dosage forms, e.g., containing from 0.05 to 10 milligrams of compound (s) of the invention, per unit dosage.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual compositions encompassed by the invention can be made using conventional methodologies or on the basis of in vivo testing using an appropriate animal model, as known in the art, or as described herein.

The nucleic acid inhibitor can comprise a delivery vehicle, including liposomes, for administration to a subject, carriers and diluents and their salts, and/or can be present in pharmaceutically acceptable formulations. Methods for the delivery of nucleic acid molecules are described in Akhtar et al., Trends in Cell Bio. 2:139, 1992; Delivery Strategies for Antisense Oligonucleotide Therapeutics, ed. Akhtar, 1995; Maurer et al., Mol. Membr. Biol., 16:129, 1999; Hofland and Huang, Handb. Exp. Pharmacol. 137:165, 1999; and Lee et al., ACS Symp. Ser. 752:184, 2000, all of which are incorporated herein by reference. Beigelman et al., U.S. Pat. No. 6,395,713 and Sullivan et al., PCT WO 94/02595 further describe the general methods for delivery of nucleic acid molecules. Nucleic acid molecules can be administered to cells by a variety of methods known to those of skill in the art, including, but not restricted to, encapsulation in liposomes, by ionophoresis, or by incorporation into other vehicles, such as hydrogels, cyclodextrins (see for example Gonzalez et al., Bioconjugate Chem. 10:1068, 1999), biodegradable nanocapsules, and bioadhesive microspheres, or by proteinaceous vectors (O'Hare and Normand, International PCT Publication No. WO 00/53722).

In the present methods, the RNA interference agent can be administered to the subject either as naked RNA interference agent, in conjunction with a delivery reagent, or as a recombinant plasmid or viral vector which expresses the RNA interference agent. Preferably, the RNA interference agent is administered as naked RNA interference agent.

The RNA interference agent of the invention can be administered to the subject by any means suitable for delivering the RNA interference agent to the cells of the tissue at or near the area of with motor neurons. For example, the RNA interference agent can be administered by gene gun, electroporation, or by other suitable parenteral administration routes.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages may mean ±1%.

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

This invention is further illustrated by the following example which should not be construed as limiting. The contents of all references cited throughout this application, as well as the figures and table are incorporated herein by reference.

EXAMPLES

Example 1

Derivation of ES Cell Lines from the SOD1G93A ALS Mouse Model

Embryonic stem cell lines were derived by crossing hemizygous mice carrying either the pathogenic (mutant) SOD1G93A transgene or the non-pathogenic (wild-type) SOD1 transgene (Gurney et al., 1994) with hemizygous mice carrying a transgenic reporter gene in which green fluorescent protein (GFP) expression is controlled by promoter elements from the Hb9 gene (Hb9::GFP) (Wichterle et al., 2002). The Hb9 gene encodes a homeodomain transcription factor that is expressed in postmitotic motor neurons (Arber, S. et al. Requirement for the homeobox gene Hb9 in the consolidation of motor neuron identity. Neuron 23, 659-74, 1999; Thaler, J. et al. Active suppression of interneuron programs within developing motor neurons revealed by analysis of homeodomain factor HB9. Neuron 23, 675-87, 1999). This Hb9::GFP transgene provides a marker for the differentiation of ES cells into motor neurons (Wichterle et al., 2002). Blastocyst stage embryos were retrieved from the progeny of these crosses and used to derive ES cell lines that were genotyped using the polymerase chain reaction (PCR) (FIG. 1A,B). These analyses identified ES cell lines that carried only the Hb9::GFP transgene (Hb9GFP), lines that carried both Hb9::GFP and the wild-type SOD1 transgene (SOD1), and a line that carried both Hb9::GFP and the mutant SOD1G93A transgene (SOD1G93A).

To determine whether these ES cells recapitulate the proper expression pattern of the Hb9::GFP reporter transgene, we assessed GFP fluorescence in the undifferentiated ES cells and in chimeras created by injecting these cells into non-transgenic blastocysts. Each of the undifferentiated cell lines lacked obvious GFP expression (data not shown). However, in E10.5 chimeras created with these cells, highly specific GFP expression was observed in the developing eye, hindbrain and spinal chord where Hb9 is known to be expressed (data not shown) (Wichterle et al., 2002; Thaler et al., 1999). Immunostaining with antibodies that preferentially recognize the human SOD1 protein confirmed the PCR genotyping of the cell lines and showed that both the SOD1 and SOD1G93A transgenes are expressed in the undifferentiated ES cells (data not shown).

Example 2

Production and Characterization of Motor Neurons by In Vitro Differentiation of SOD1G93A ES Cells To determine whether pathogenic properties associated with ALS can be recapitulated in vitro, we generated motor neurons by differentiating the transgenic ES cell lines as previously described (Wichterle et al., 2002). Briefly, ES cells were dissociated into a single cell suspension, allowed to spontaneously aggregate into embryoid bodies (EBs) over 48 hours and then treated with retinoic acid (RA) and soluble Sonic Hedgehog (Shh) protein[1] (Wichterle et al., 2002) for 5 days.

Figure 5:
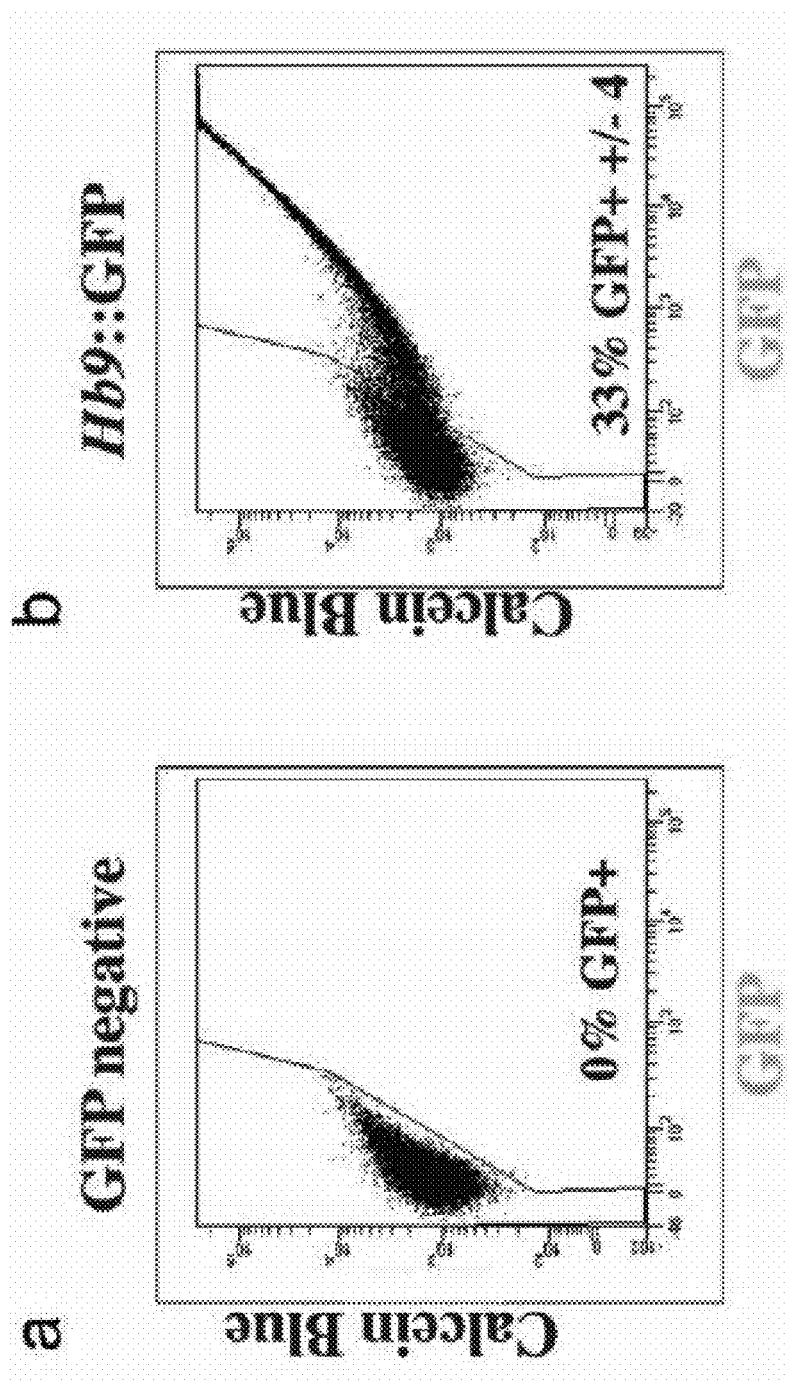
FIG. 5 shows the percentage of differentiating EB cells that express GFP. FACS analysis of cells dissociated from EBs after 5 days of treatment with retinoic acid and shh.
Figure 5:
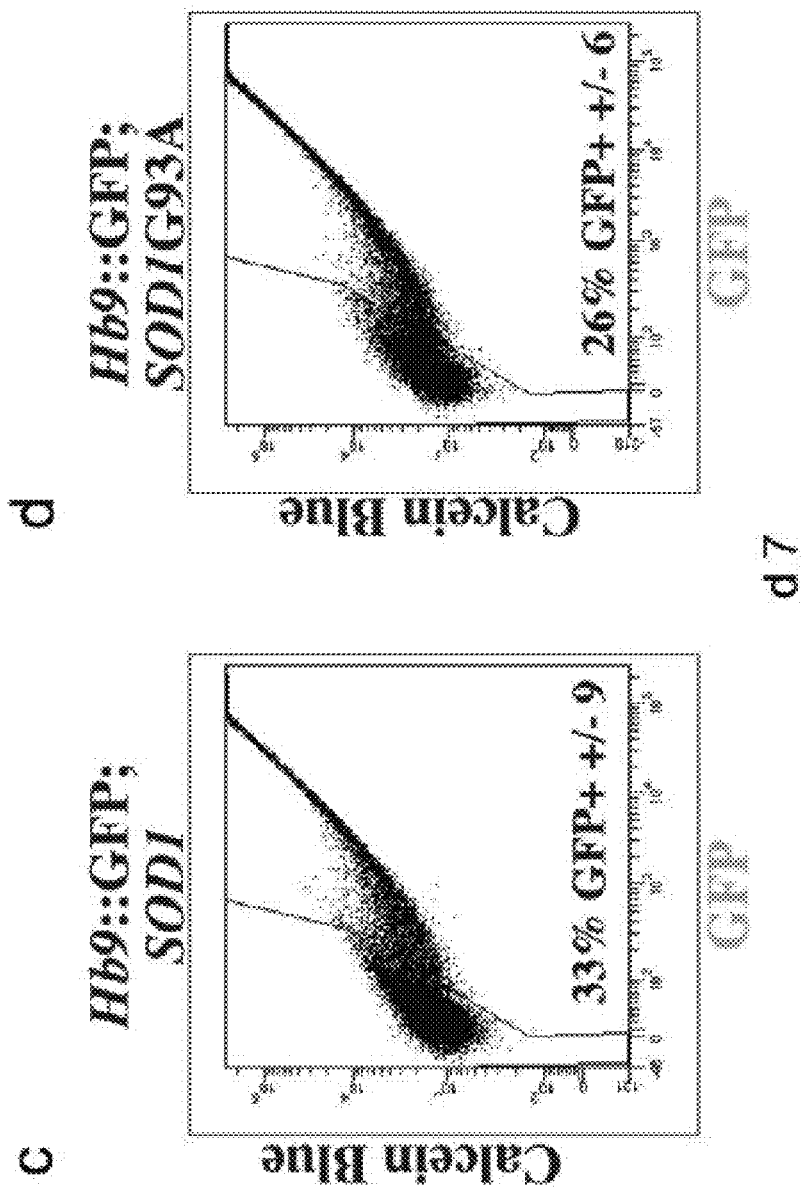

We found that the SOD1G93A genotype does not interfere with the initial specification or differentiation of motor neurons, as no significant qualitative or quantitative differences were observed in the differentiation of the three cell lines. GFP expression in EBs derived from the different cell lines, including SOD1G93A, first appeared 5 days after treatment with Shh and RA (data not shown). Two days later, when EBs were dissociated with papain and plated, GFP positive cells with an obvious neuronal morphology could be observed (data not shown). We used fluorescence activated cell sorting (FACS) to determine the percentage of differentiating ES cells that expressed GFP and found no statistically significant differences between the three cell lines (Hb9GFP 33%+/−4%, SOD1 33%+/−9%, SOD1G93A 26%+/−6%) (see FIG. 5).

To confirm that the EB cells expressing GFP differentiated into bone fide motor neurons, we dissociated the EBs and performed immunostaining with antibodies that recognize proteins known to be expressed in motor neurons (data not shown). As was previously observed with normal ES cell lines (Wichterle et al., 2002), we found that GFP positive cells derived from the SOD1G93A cell line expressed a neuronal form of tubulin (data not shown), the transcription factors Hb9 and Isl1/2 (data not shown) and the enzymatic machinery required to generate acetylcholine (data not shown).

Example 3

The SOD1G93A Genotype Affects the Survival of Motor Neurons in Culture

Figure 2:
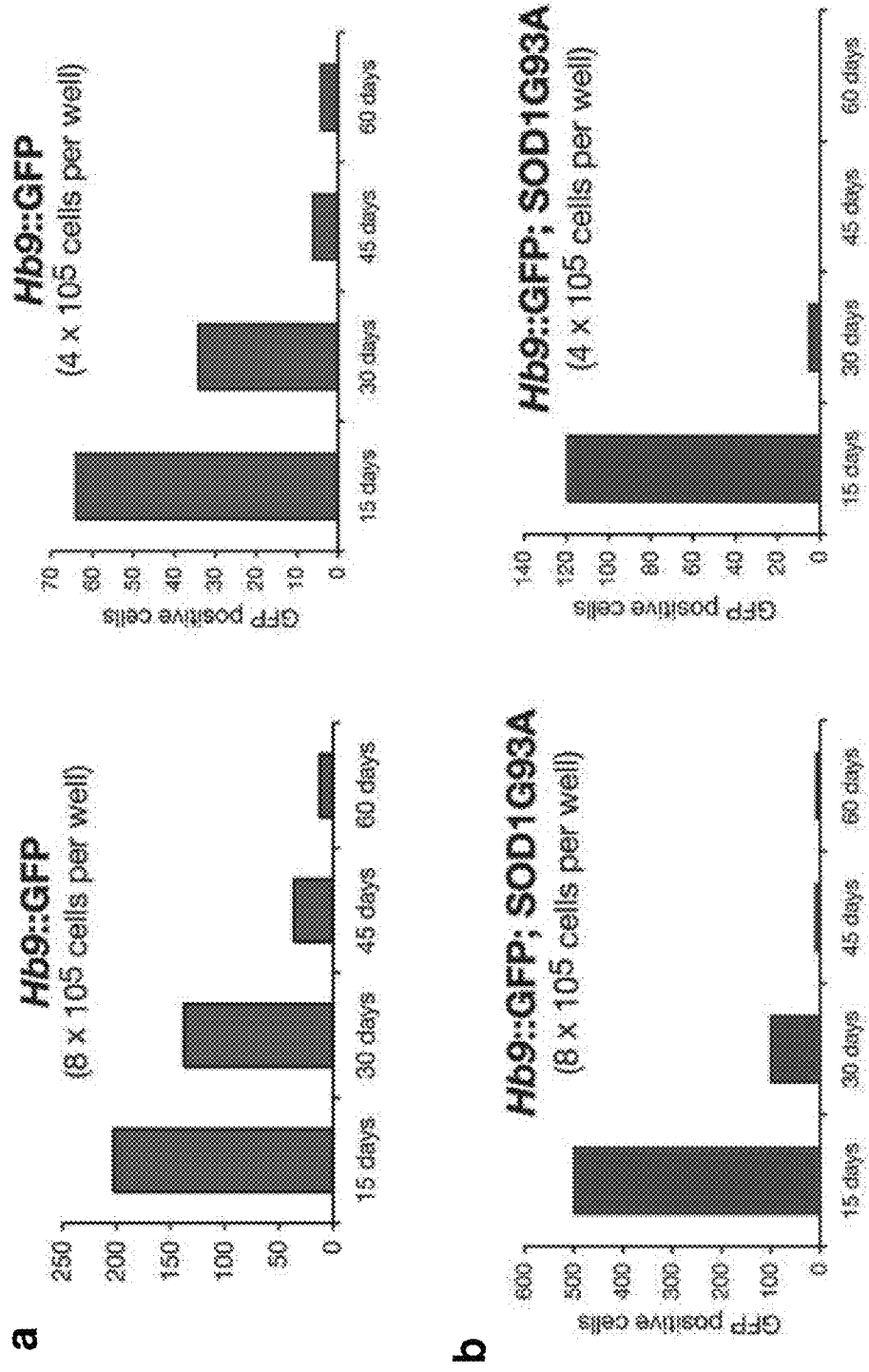
FIG. 2 shows the effect of genetic background on motor neuron survival. Number of GFP positive cells derived from (FIG. 2A) Hb9GFP and (FIG. 2B) SOD1G93A ES cell lines present 15, 30, 45 and 60 days after dissociation of EBs plated at two different concentrations ($8 \times 10^5$ and $4 \times 10^5$ per well).
Figure 2:
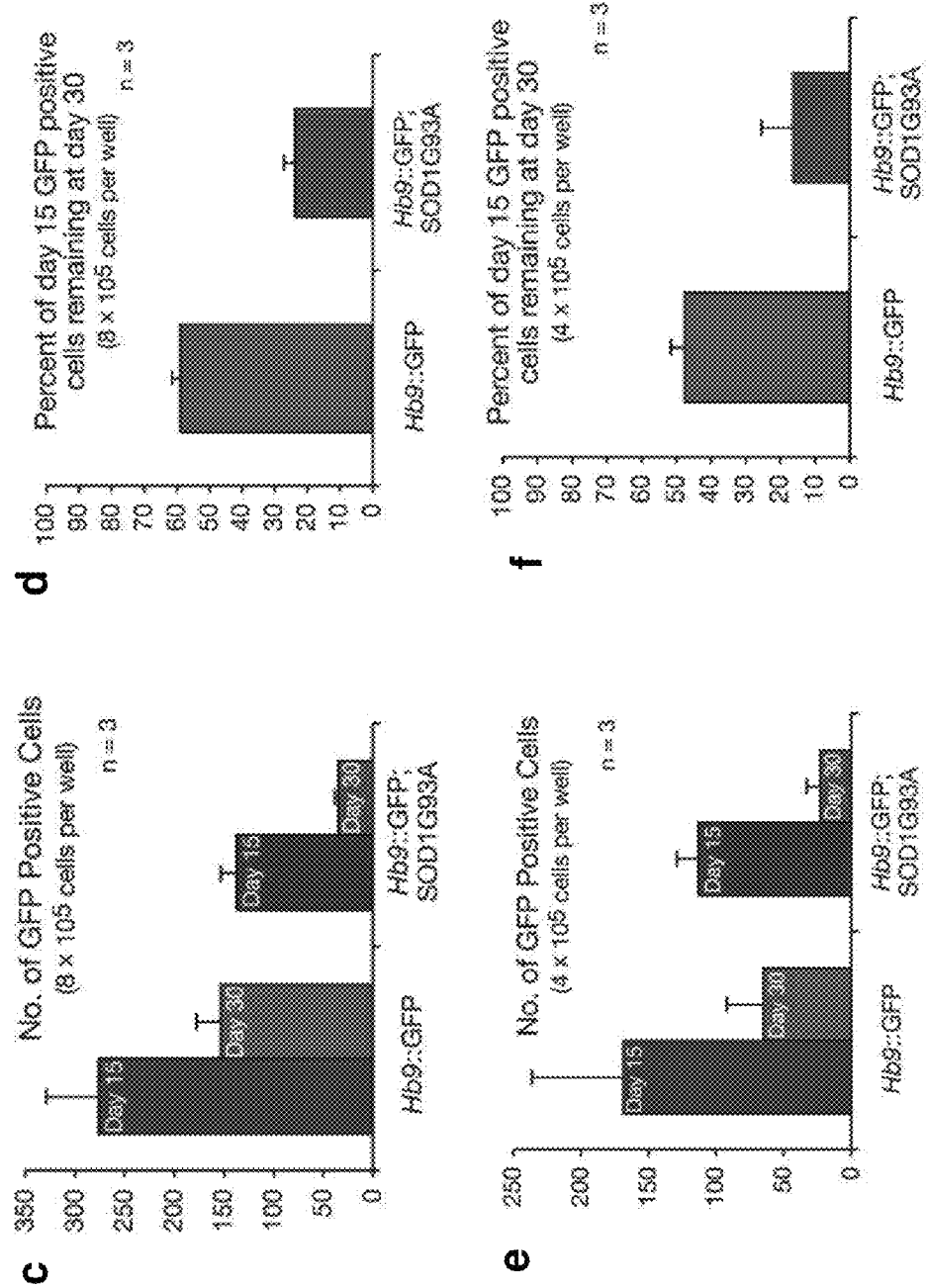

ALS is a late onset, progressive neurodegenerative disease, and mice carrying the human SOD1G93A transgene develop symptoms as a consequence of motor neuron loss after several weeks. Therefore, it seemed possible that motor neurons derived from ES cells might display neurodegenerative properties only after they have been maintained in culture for a prolonged length of time. To determine the period of time that ES cell derived motor neurons can survive in culture, we dissociated day 7 Hb9GFP and SOD1G93A EBs and plated the resulting mixture of GFP positive and negative cells at two different densities in the presence of neurotrophic factors (Wichterle et al., 2002) (FIG. 2). We observed that the number of GFP positive cells decreased precipitously during the first two weeks, and then continued to decrease over the following weeks. However, GFP positive cells could still be detected in both HB9GFP and SOD1G93A derived cultures 54 days after plating (data not shown). Although GFP positive cells were present in both cultures at later time points, the number of cells expressing GFP decreased more rapidly in the SOD1G93A (FIG. 2B) cultures than in Hb9GFP control cultures (FIG. 2A).

To confirm the affect of the SOD1G93A genotype on the number of GFP positive cells, we differentiated both the SOD1G93A and Hb9GFP ES cells into motor neurons, plated equal numbers of cells at two different concentrations ($8 \times 10^5$ (n=3) and $4 \times 10^5$ (n=3) EB cells per well) and counted the number of GFP positive neurons in the cultures at 2 and 4 weeks (FIG. 2C-F). Under both plating conditions, significantly fewer GFP positive cells were observed in the SOD1G93A cultures at both 2 and 4 weeks (FIG. 2C-F).

Example 4

Histopathological Hallmarks of ALS can be Observed in ES Cell-Derived Motor Neurons Hb9GFP and SOD1G93A ES cells differentiate into motor neurons at a similar efficiency, but the cultures show differences in the number of GFP positive cells over time. Thus, a pathological process may underlie the preferential loss of GFP positive cells in the SOD1G93A cultures. To investigate these processes and to determine whether they mirror events that occur during the progression of ALS, we examined motor neurons in culture for the presence of histopathological hallmarks of the disease. Motor neurons in ALS patients and transgenic mice carrying the SOD1G93A allele accumulate protein inclusions that are recognized by antibodies specific to the SOD1 protein (Boillee et al., 2006; Bruijn et al., 19970. We therefore determined whether aggregation of the mutant SOD1 protein accompanies the loss of GFP positive motor neurons in SOD1G93A cultures by staining with antibodies specific to the human SOD1 protein at 7, 14 and 21 days following EB dissociation (data not shown). At 7 and 14 days following dissociation both the wild-type SOD1 protein and the mutant SOD1G93A protein were localized broadly and evenly in the cytoplasm of GFP positive motor neurons (data not shown). However, at 14 days punctate structures staining brightly with the SOD1 antibody could be observed in a small proportion of motor neurons expressing the SOD1G93A protein, (data not shown).

Figure 3:
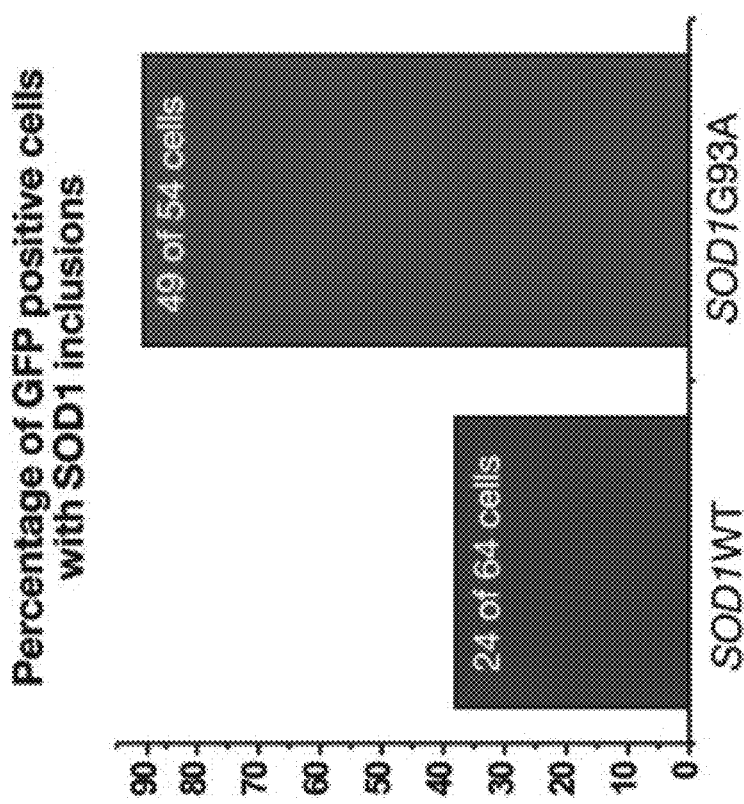
FIG. 3 shows intracellular aggregation of SOD1 protein in cultured motor neurons. Percentage of GFP-Positive motor neurons with SOD1 inclusions present after 21 days in culture.
Figure 6:
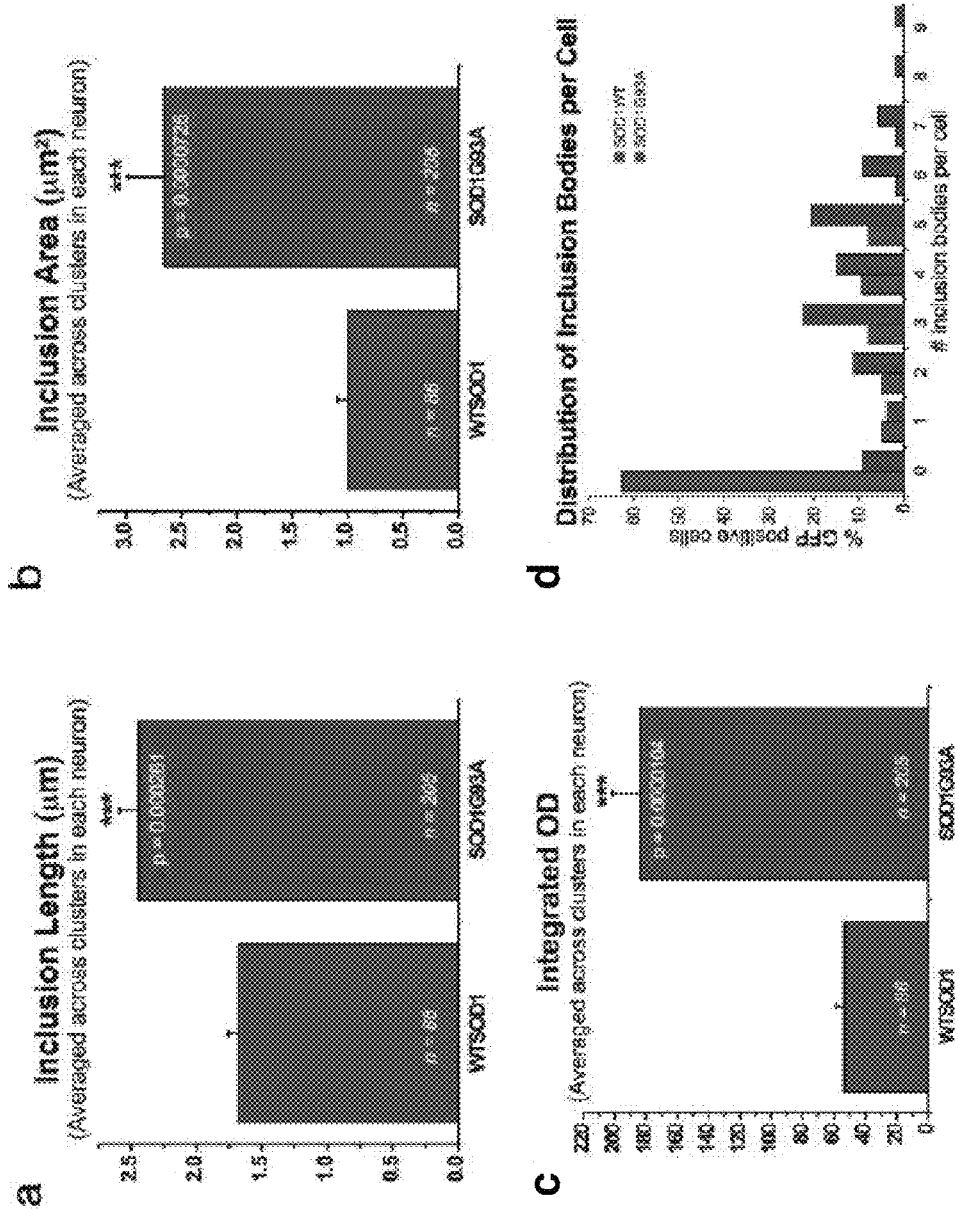
FIG. 6 shows quantitative and qualitative analysis of SOD1 protein inclusions in ES cell derived motor neurons.

When cultures were examined 21 days after dissociation, a shift in protein localization was observed in the SOD1G93A motor neurons. In 49/54 (79.75±7.75%) of the motor neurons selected at random for analysis by GFP expression, the SOD1G93A protein localized to inclusions in the perinuclear space, in the cell body and also in the neural processes (FIG. 3). When control motor neurons expressing wild-type SOD1 were examined 21 days after differentiation (FIG. 3), we observed inclusions in a smaller proportion of cells 24/64 (35.93±0.43%). The inclusions in motor neurons expressing the SOD1 G93A allele were also significantly larger in area (FIG. 6A), significantly longer (FIG. 6B) and displayed a higher optical density, suggesting that they contained more SOD1 protein at a higher concentration (FIG. 6C).

The levels of ubquitinated proteins are significantly elevated in motor neurons of ALS patients and SOD1G93A transgenic animals during neural degeneration (Bruijn et al., 1997; Ince, P. G., et al., Amyotrophic lateral sclerosis associated with genetic abnormalities in the gene encoding Cu/Zn superoxide dismutase: molecular pathology of five new cases, and comparison with previous reports and 73 sporadic cases of ALS. J Neuropathol Exp Neurol 57, 895-904, 1998; Wang, J. et al. Copper-binding-site-null SOD1 causes ALS in transgenic mice: aggregates of non-native SOD1 delineate a common feature. Hum Mol Genet. 12, 2753-64, 2003; Watanabe, M. et al. Histological evidence of protein aggregation in mutant SOD1 transgenic mice and in amyotrophic lateral sclerosis neural tissues. Neurobiol Dis 8, 933-41, 2001). Examination of the ES cell-derived motor neurons revealed an increase in staining with anti-ubiquitin antibodies, relative to other cells in the culture. This staining often colocalized with the SOD1 protein inclusions (data not shown).

The death of motor neurons in ALS patients and transgenic mice carrying mutant SOD1 genes occurs through activation of programmed cell death pathways. Apoptosis in these cells has been proposed to be mediated through the release of cytochrome c and the activation of caspase-3 (Pasinelli, P., Houseweart, M. K., Brown, R. H., Jr. & Cleveland, D. W. Caspase-1 and -3 are sequentially activated in motor neuron death in Cu, Zn superoxide dismutase-mediated familial amyotrophic lateral sclerosis. Proc Natl Acad Sci USA 97, 13901-6, 2000; Raoul, C. et al. Motoneuron death triggered by a specific pathway downstream of Fas. potentiation by ALS-linked SOD1 mutations. Neuron 35, 1067-83, 2002). Examination of the SOD1G93A motor neurons 14 days after dissociation of EBs, revealed that some neurons expressed activated caspase-3 and contained diffuse cytoplasmic staining with cytochrome c specific antibodies (data not shown). Thus, the SOD1G93A motor neurons appear to initiate cell death pathways in vitro that are similar to those activated in vivo during the course of disease (Pasinelli et al., 2000).

Example 5

SOD1G93A Glial Cells Adversely Affect Survival of ES Cell Derived Motor Neurons

Both autonomous defects in motor neurons and toxic non-cell autonomous interactions with other cell types in the spinal cord have been implicated in ALS pathology (Bruijn et al., 2004; Clement et al., 2003; Boillee et al., 2006). Only a subset of cells in EBs became motor neurons under our differentiation conditions. We therefore considered the possibility that cells within the EBs might also develop into other cell types that normally associate with neurons in the spinal cord. These additional cells might, as suggested by chimeric experiments, contribute non-cell autonomously to the loss of neurons in SOD1G93A cultures. Glial cells are closely associated with motor neurons, and both are derived from a common progenitor in vivo (Zhou, Q. & Anderson, D. J. The bHLH transcription factors OLIG2 and OLIG1 couple neuronal and glial subtype specification. Cell 109, 61-73, 2002). We therefore addressed the possibility that glial cells are present in our cultures. To determine if these cells, were also produced by our differentiation protocol, we stained SOD1G93A cultures with antibodies specific to the glial fibrillary acidic protein (GFAP) (Bignami, A. & Dahl, D. Astrocyte-specific protein and neuroglial differentiation. An immunofluorescence study with antibodies to the glial fibrillary acidic protein. J Comp Neurol 153, 27-38, 1974). Indeed, GFAP positive cells were found in close association with GFP positive motor neurons (data not shown). We found that approximately 30% of the cells at 28 days were GFAP positive (Hb9GFP: 31%, SOD1: 32%, SOD1G93A: 36%). Thus, it seemed possible that the SOD1G93A glial cells in these cultures might be adversely affecting motor neuron survival.

Figure 4:
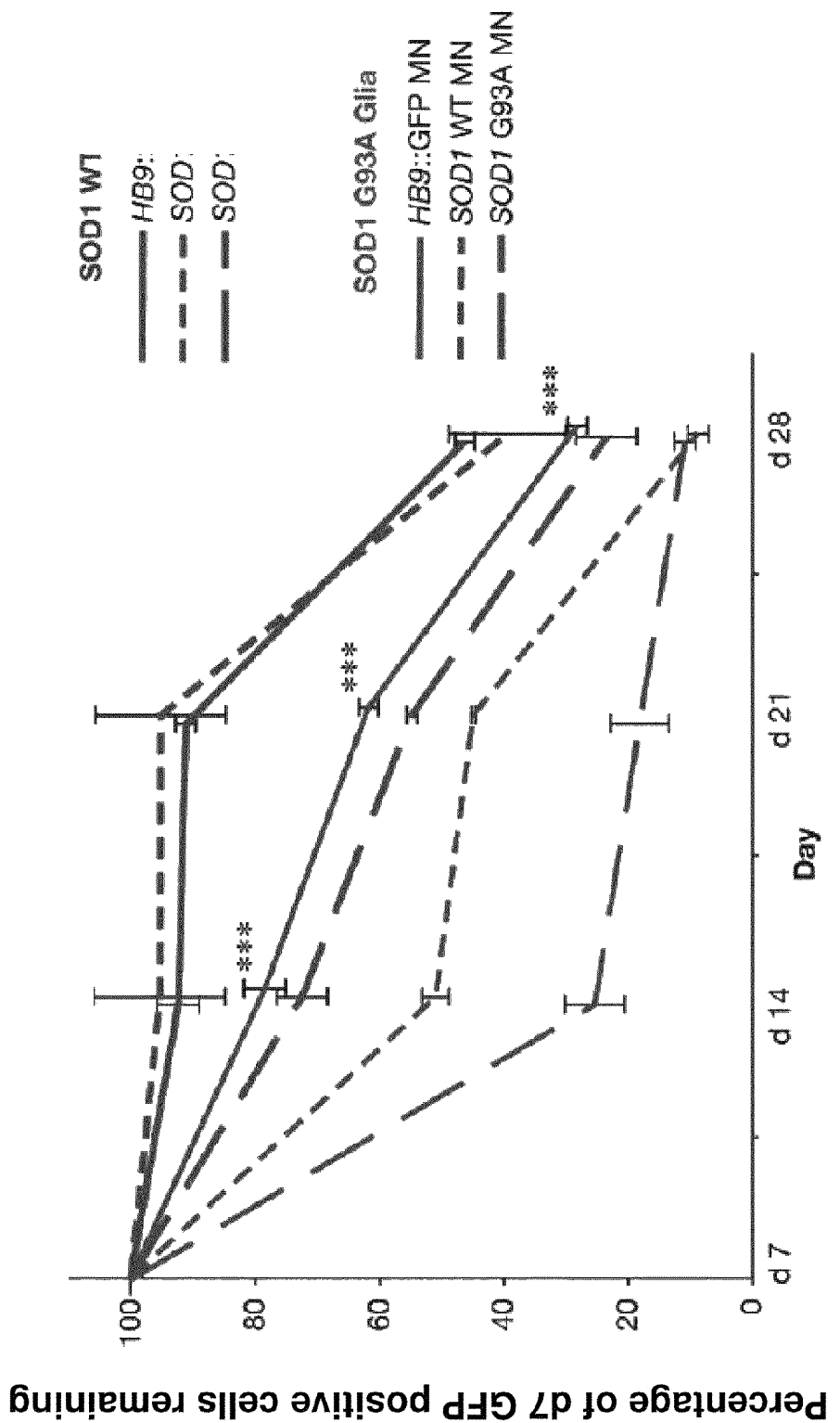
FIG. 4 shows the graph shows percentage of Hb9GFP positive cells over time in all the conditions studied. Glial cell genotype directly affects motor neuron survival in culture. Experiments were made in triplicate and results were normalized to the number of cells found at 7 days in vitro.

To examine this possibility, we differentiated the three ES cell lines (Hb9GFP, SOD1 and SOD1G93A) into motor neurons and plated them on established monolayers of primary glia isolated from the cortex of neonatal mice with differing SOD1 genotypes (wild-type SOD1, and the mutant SOD1G93A) (Banker, G. & Goslin, K. Culturing nerve cells, xii, 666, 11 of plates (MIT Press, Cambridge, Mass., 1998). During the first seven days after plating on either glial monolayer, motor neurons of all genotypes increased in size and took on a more mature morphology (data not shown). However, by 14 days after plating there was a 50% decrease in the number of wild-type SOD1 derived motor neurons in co-cultures with SOD1G93A glia compared to the same preparation of neurons plated on wild-type SOD1 glia. Similarly, we did not see a significant reduction in the number of Hb9GFP motor neurons when plated on SOD1 glia, but did see a reduction of 30% if the same neurons were co-cultured with SOD1G93A glia (FIG. 4). These data suggest that wild-type SOD1 glia provide a permissive environment for motor neuron growth and differentiation, comparable to other well-established in vitro systems for motor neuron culture (Ullian, E. M., Harris, B. T., Wu, A., Chan, J. R. & Barres, B. A. Schwann cells and astrocytes induce synapse formation by spinal motor neurons in culture. Mol Cell Neurosci 25, 241-51, 2004; Allen, N. J. & Barres, B. A. Signaling between glia and neurons: focus on synaptic plasticity. Curr Opin Neurobiol 15, 542-8, 2005; Ullian, E. M., Christopherson, K. S. & Barres, B. A. Role for glia in synaptogenesis. Glia 47, 209-16, 2004). In contrast, when we co-cultured wild type motor neurons (SOD1 or Hb9GFP) with glia from SOD1G93A mice, we observed a marked reduction in survival (FIG. 4).

We next investigated the affect of the presence of the mutant SOD1 transgene in motor neurons in the co-culture system. When mutant SOD1G93A motor neurons were plated on wild-type SOD1 glial cells, there was a 27% decrease in the number of neurons between 7 and 14 days. The loss of motor neurons increased to 75% when the mutant SOD1G93A motor neurons were cultured with mutant SOD1G93A glia (FIG. 4).

Together, our results show that the SOD1G93A genotype in glial cells has a negative effect on motor neuron survival regardless of the motor neuron genotype. However, a greater negative effect is observed with the SOD1G93A motor neurons. Thus, glial cells have a non-cell autonomous effect on motor neuron survival and mutant motor neurons are more sensitive to the effect.

Figure 7:
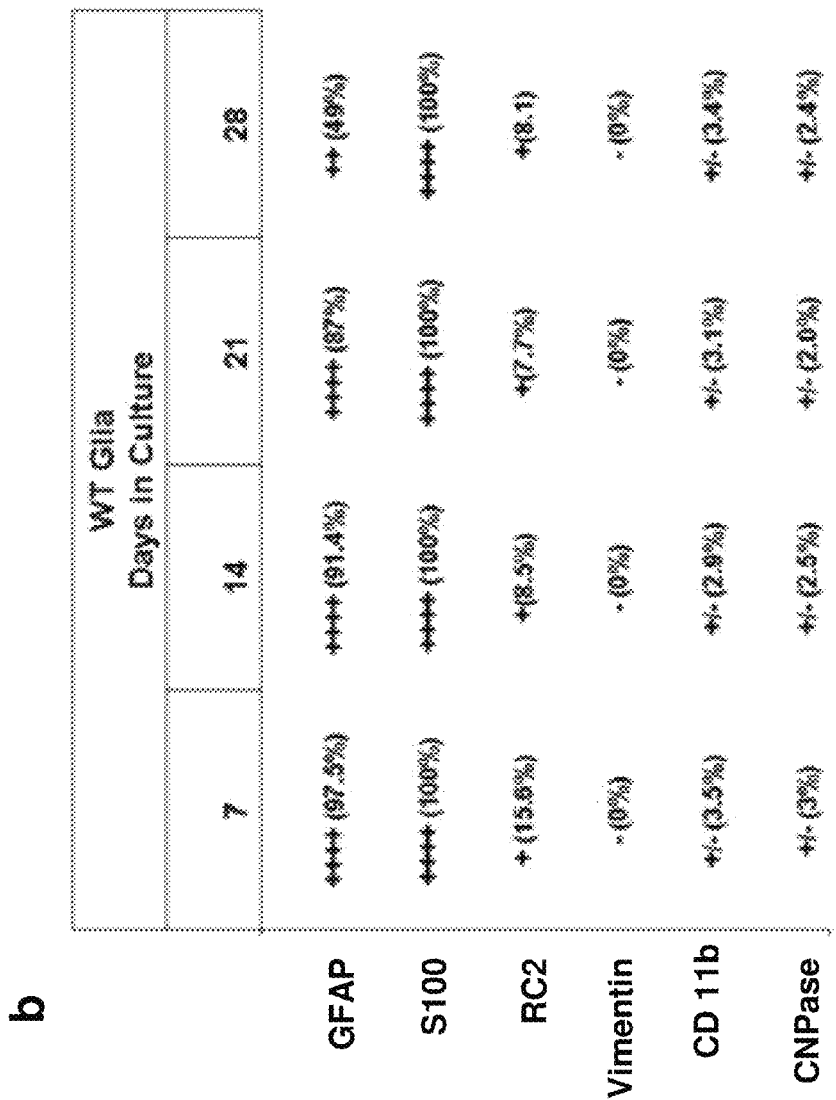
FIG. 7 shows characterization of primary glial monolayers derived from SOD1 and SOD1G93A mice.

To determine whether the differing influences of the wild-type SOD1 and the mutant SOD1G93A glial cell cultures could be explained by the presence of different proportions of distinct glial cell types, we characterized the two populations by immunostaining with established glial markers. We did not observe a significant difference in the wild-type SOD1 and the mutant SOD1G93A glial populations over time (FIG. 7).

Example 6

Methods

Examples 1 through 5 were performed using the following methods:

Derivation of mouse Embryonic Stem Cells. ES cell lines were derived from crosses between mice transgenic for Hb9:GFP (Jackson lab, Stock Number: 005029) and mice transgenic for SOD1$^{G93A}$ (Jackson lab, Stock Number: 004435) or SOD1$^{WT}$ (Jackson lab, Stock Number: 002297). Transgenic Hb9:GFP females were injected IP with 7.5 units of pregnant mares' serum (Calbiochem) followed 46-50 h later with 7.5 units of human chorionic gonadotropin (HCG) (Calbiochem). After administration of HCG, females were mated with either SOD1G93A or SOD1 transgenic males. Females were scarified three days later and blastocysts were flushed from the uterine horn with mES cell media (Knockout-DMEM (GIBCO), 15% Hyclone Fetal Bovine Serum (Hyclone), 10.000 unit Penicillin and 1 mg/ml Streptomicin (GIBCO), 2 mM Glutamine (GIBCO), 100 mM non-essential aminoacid (GIBCO), 55 mM beta-mercapto-ethanol (GIBCO), 1,000 units/ml leukocyte inhibiting factor (Chemicon)). Blastocysts were then plated individually into one mm-well of a tissue culture dish containing a feeder layer of mitotically inactivated mouse embryonic fibroblast, in the presence of mES cell media supplemented with the MEK kinase inhibitor PD98059 (cell signaling, inc). 48 hours after plating embryos, one half volume of fresh media was added to each culture well. Starting three days after plating, the culture media was changed.

Four to five days after plating, ICM-derived outgrowth were observed, dislodged from the rest of the cells with a Pasteur pipette, washed once in a drop of PBS and then incubated for 10 minutes in a drop of 0.25% trypsin at 37 C. The ES cells clumps were then gently dissociated with a Pasteur pipette filled with mouse ES cell media and transferred onto a fresh layer of fibroblasts in a 10 mm tissue culture well. For routine culture, the mouse ES cells are generally split 1:6 with a solution of 0.25% trypsin (GIBCO) every 2-3 days.

Generation of Chimeric embryos. Chimeric embryos were generated as previously described (Hogan, B. in "Manipulating the mouse embryo: a laboratory manual", xvii, 497 p. (Cold Spring Harbor Laboratory Press, Plainview, N.Y., 1994). Blastocysts were collected from the uterus of non-transgenic pregnant females mice 3.5 days postcoitum. The ES cells were injected (about 10 for each blastocyst) using a microinjection pipette with a diameter of 12-15 μm applying a brief pulse of the Piezo (Primetech, Ibaraki, Japan) on one side of the blastocyst and pushing the needle through the zona and trophectoderm layer into the blastocoel cavity. Ten injected blastocysts were transferred to each uterine horn of 2.5 days postcoitum pseudopregnant Swiss females that had mated with vasectomized males. Recipient mothers were sacrificed at 10.5 days postcoitum, and embryos were quickly removed from the uterus and placed in a dish with cold PBS for whole mount analysis of GFP fluorescence.

Differentiation of mES cells into motor neurons. Mouse ES cells were differentiated into motor neurons according to methods previously described (Boillee et al., 2006). The ES cells were grown at 70-80% confluence in a 10 cm plate (Falcon) in mouse ES cells media. To form EB's, cells were washed once with a PBS solution to eliminate the traces of media and then incubated with 1 ml of 0.25% trypsin (GIBCO) for 5-10 minutes at room temperature. After this the cells were resuspended in 10 ml of DM1 media (DMEM-F12 (GIBCO), 10% Knockout serum (GIBCO), pen strep, glutamine (GIBCO) and 2-mercaptoethanol (GIBCO)), they were counted and plated at a concentration of 200.000/ml in Petri dishes (Falcon). After 2 days the embryoid bodies were split from 1 dish into 4 new Petri dishes containing DM1 medium supplemented with RA (100 nM μM; stock: 1 mM in DMSO, Sigma) and sonic hedgehog (300 nM, R&D Systems). The media is changed after 3-4 days. On day 7 the embryoid bodies were dissociated in single cells suspension. The EBs were collected in a 15 ml falcon tube, centrifuged at 1000 rpm for 5 min, washed once with PBS and incubated in Earle's Balanced Salt Solution with 20 units of papain and 1000 units of Deoxyribonuclease I (Worthington Biochemical Corporation) for 30-60 minutes at 37° C. The mixture was then triturated with a 10 ml pipette and centrifuged for 5 minutes at 1000 RPM. The resulting cell pellet was washed once with PBS and finally resuspended in supplemented F12 media (F12 medium (GIBCO) with 5% horse serum (GIBCO), B-27 supplement (GIBCO), N2 supplement (GIBCO)) with neurotrophic factors (GDNF, CNTF, and BDNF (10 ng/ml, R&D Systems)). The cells were then counted and plated on Poly-D-Lysine/Laminin CultureSlides (BD biosciences) or on a layer of primary glia cells. For the motor neurons survival experiments, GFP positive cells with visible axons and dendrites were counted at different time points after plating (7, 14, 21, 28 days).

Polymerase chain reaction. All PCR reactions were performed using an MJ Research Thermal Cycler, and TaKaRa Ex Taq HS (Takara) enzymes. For the SOD1 genotyping of the newly derived ES cell lines and transgenic mice the forward primer: CAT CAG CCC TAA TCC ATC TGA (SEQ ID NO:1) and reverse primer: CGC GAC TAA CAA TCA AAG TGA (SEQ ID NO:2) amplified a 236 by fragment in the 4$^{th}$ exons of the gene. As an internal control a set of primers that amplified a 324 by fragment of the IL-2 gene (forward: CTA GGC CAC AGA ATT GAA AGA TCT (SEQ ID NO:3), reverse: CAT CAG CCC TAA TCC ATC TGA (SEQ ID NO:4)) were used. The annealing temperature for this reaction was 60° C. for 35 cycles. For GFP a set of primers (forward: AAG TTC ATC TGC AAC ACC (SEQ ID NO:5), reverse: TCC TTG AAG AAG ATG GTG CG (SEQ ID NO:6)) that amplified a fragment of 173 by of the gene were used, with an annealing temperature of 60° C. for 35 cycles.

FACS. For FACS analysis a BD biosciences LSRII flow cytometer was used. The embryoid bodies were dissociated with papain and resuspended in cold PBS with 2% FBS, Calcein blue (INVITROGEN™) was used to assay the cell viability. The cells were then analyzed using a non transgenic mouse embryonic stem cell lines as a negative control. The FACS Diva software package (BD Biosciences) was used for data analysis Glia Cultures. Glia monolayers were obtained from P2 mice born from matings between transgenic SODG93A. Tissue was isolated in Calcium and Magnesium Free-Hanks's BSS (HBSS). Under a dissecting microscope the cortex was isolated and carefully striped of the meninges. The tissue was split in small pieces then transferred to a 50 ml centrifuge tube in a final volume of 12 ml of HBSS. Tissue digestion was performed using trypsin-EDTA (GIBCO BRLno.25200) and 1% DNAse (Sigma no.DN-25) at 37° C. for 15 min, swirling the mixture and periodically. We collected the dissociated tissue and triturated using a fire polish Pasteur glass pipette and filtered the combined supernatant through a 72 µm nylon mesh (NITEX 100% polyamide Nylon Fiber TETKO Inc.) to remove any undissociated tissue. The filtered material was centrifuged at 1000 rpm for 5 min to pellet the cells, resuspend in 2 ml of Glia medium (Minimum Essential Medium with Earl's salts, GIBCO BRL no. 11095-080, 20% Glucose, Penicillin-streptomycin, GIBCO BRL no.15145-014, and 10% Horse Serum GIBCO BRL no.26050-070) and cell number was counted. The yield from one brain was generally enough to plate one T75 flask (Falcon no.3084). Once monolayers were confluent (generally in 10 to 14 days) cells were replated on 24 or 12 well multiwell dishes over poly-D-Lysine (0.5 mg/ml for 30 min RT) coated glass cover slips.

Immunocytochemistry analysis. The cells were fixed with 4% paraformaldehyde-PBS, blocked and permeabilized with BSA (1%)-Triton X100 (0.1%). After incubating overnight with the following antibodies: mouse monoclonal anti-Tuj1 (Covance), Islet 1 Islet2, RC2 (Developmental Studies Hybridoma Bank University of Iowa, IA, USA) anti-sod1 (SIGMA), S100 (Chemicon), CNPase (Abcam) and rabbit anti-HB9 (Tom Jessell, Columbia University), GFAP (Chemicon) anti-ubiquitin (DAKO); goat anti-Vimentin (Chemicon); rat anti-CD 11b (Abcam) (see Table 1)
Table 1 Describes Primary Antibodies Used. Antiserum (Host Species), Working Dilution and Source.

| Antiserum | Dilution | Source |
| --- | --- | --- |
| Tuj 1 (anti-Mouse) | 1/1000 | Covance |
| Islet 1 (anti-Mouse) | 1/1 | Hybridoma Bank |
| ChAT (anti-Goat) | 1/100 | Chemicon |
| Hb9 (anti-Rabbit) | 1/1000 | Jessel Lab |
| GFAP (anti-Rabbit) | 1/1000 | Chemicon |
| S100 (anti-Mouse) | 1/100 | Chemicon |
| RC2 (anti-Mouse) | 1/1 | Hybridoma Bank |
| Vimentin (anti-goat) | 1/100 | Chemicon |
| CD 11b (anti-Rat) | 1/100 | Abcam |
| hSOD1 (anti-Mouse) | 1/200 | Sigma |
| Caspase 3 (anti-Rabbit) | 1/2000 | BD Pharmingen |
| Ubiquitin (anti-Rabbit) | 1/200 | DAKO |
| Cytochrome C (anti-Mouse) | 1/200 | Abcam |

The cells were then incubated with Donkey anti-rabbit conjugated to Cy3 (1:100; 2 h) and Donkey anti mouse conjugated to Cy5 second antibodies (1:100; 2 h; Jackson ImmunoResearch (West Grove, Pa., USA). After mounting the samples in Vectashield (Vector Labs, Burlingame, Calif., USA), confocal or epi-fluorescence microscopy was performed using Olympus FV 1000, 40× and 60× oil immersion objective 1.45NA or fluorescent microscope Olympus IX70. Image acquisition was performed using FLUOVIEW software 4.0 for relative fluorescence analysis, all settings such as exposure time, magnification and gain were maintained constant for all samples. Offline analysis of relative intensities for all the samples was done using Metamorph 4.5 (Downingtown, Pa., USA). Only cells having morphological features of neurons (i.e., phase bright soma and several neurites) were considered for subsequent analysis.

Neuronal Density. HB9-GFP positive motor neurons were counted for condition studied (Zeiss microscope, 40×1.3 NA, oil immersion objective). The density of neurons, normalize as a percent of initial number counted at 7 DIV or 14 DIV was established for all conditions studied. These experiments were carried out three times as independent experiments.

Data analysis. The data was obtained from control and SOD1G93A motor neurons in parallel conditions (sister plates) to reduce dispersion. Statistical analysis were performed using Student's t-Test or ANOVA and are expressed as arithmetic mean±S.E.M.; t-test values of * $P<0.05$,  $P<0.01$, * $P<0.005$ were considered statistically significant. Each set of data presented was performed in sister cultures to reduce variability. Similar significances were found expressing the data in cumulative distributions plots. Therefore, we chose to present the data as mean±E.M. to simplify its presentation. The kinetic analysis was done using Mini-Analysis 5.0 (Synaptosoft).

Example 7

Human ES Cell Lines are Sensitive to SOD1G93A Glia

Figure 8:
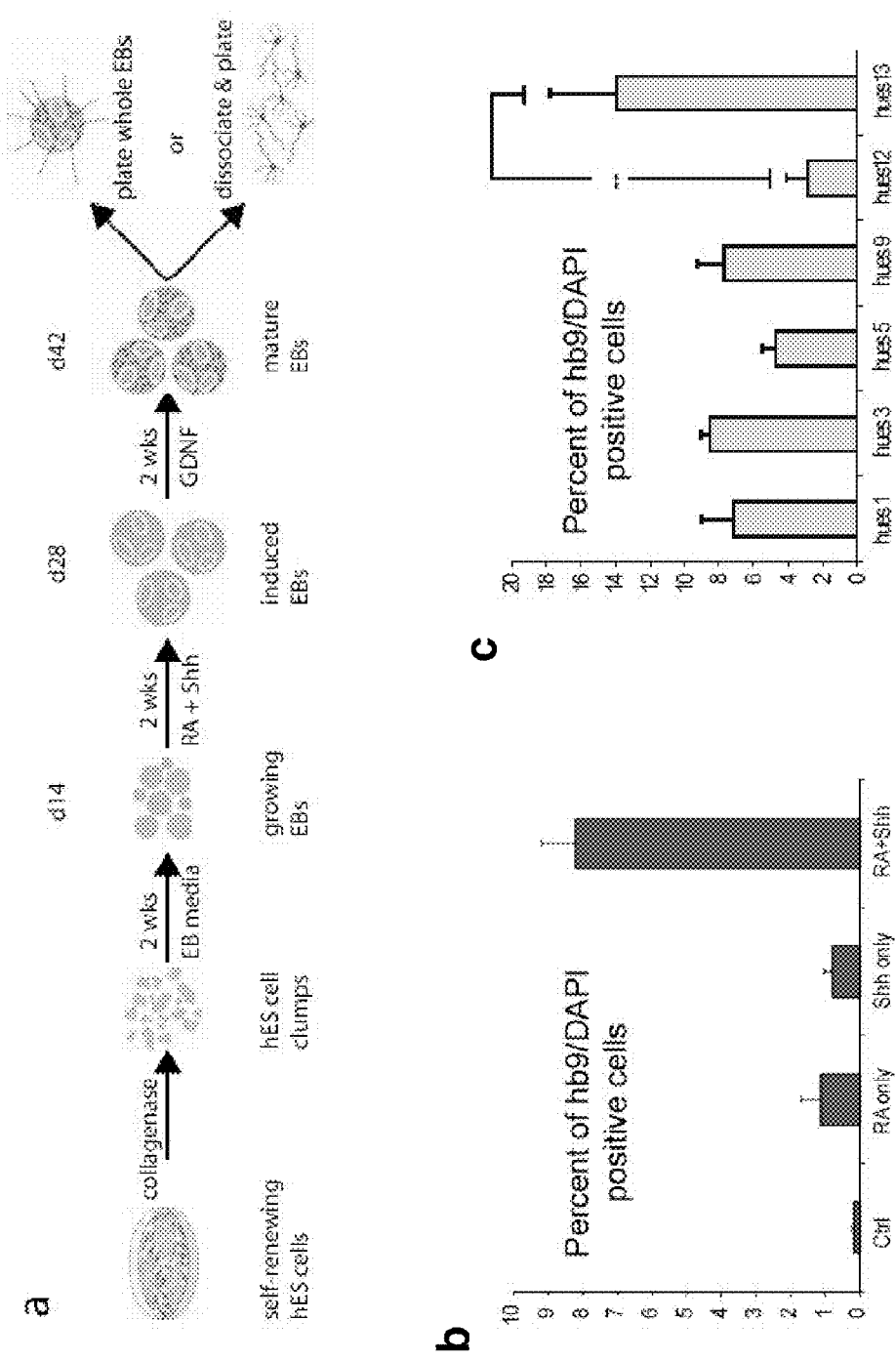
FIG. 8 shows one embodiment of differentiation of human ES cells into motor neurons.
Figure 12:
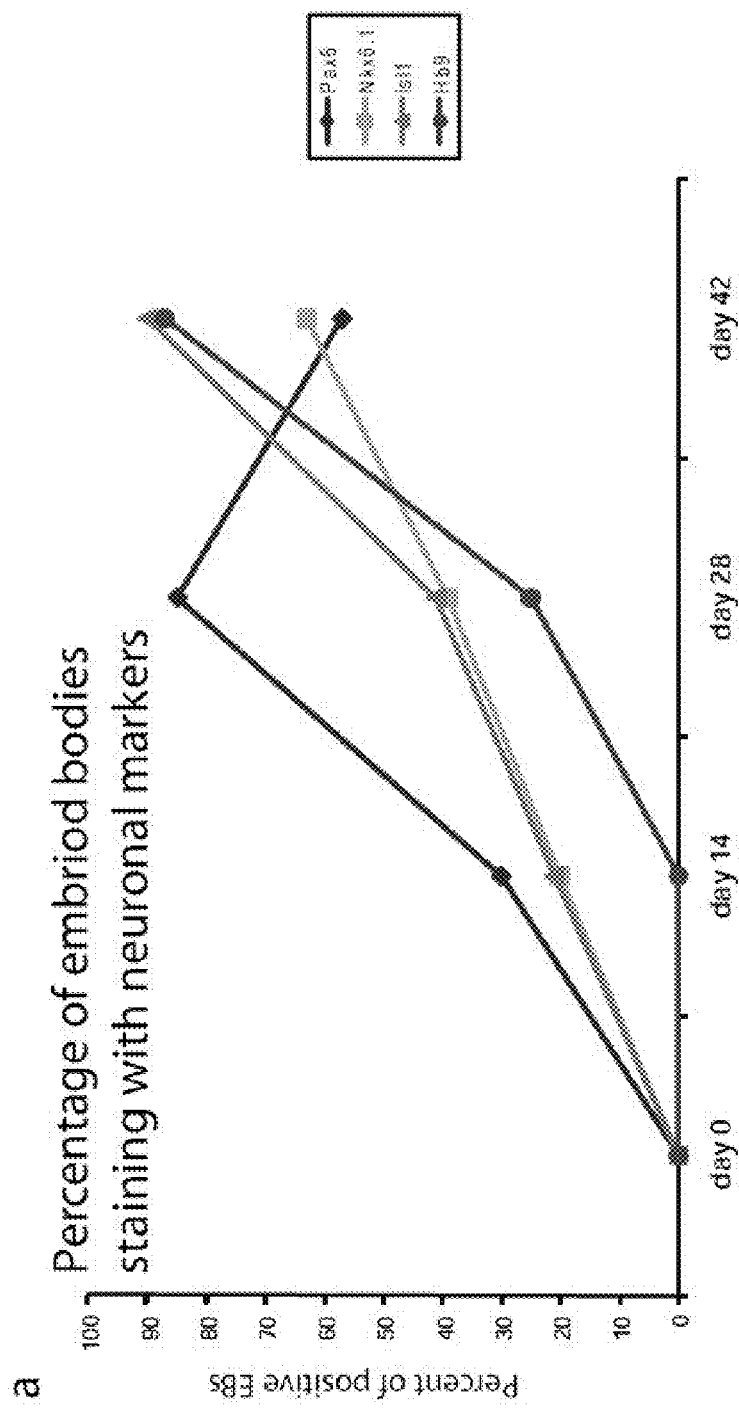
FIG. 12 shows neuronal marker expression at different time points during one embodiment of differentiation from human ES cells toward the motor neuron fate.
Figure 12:
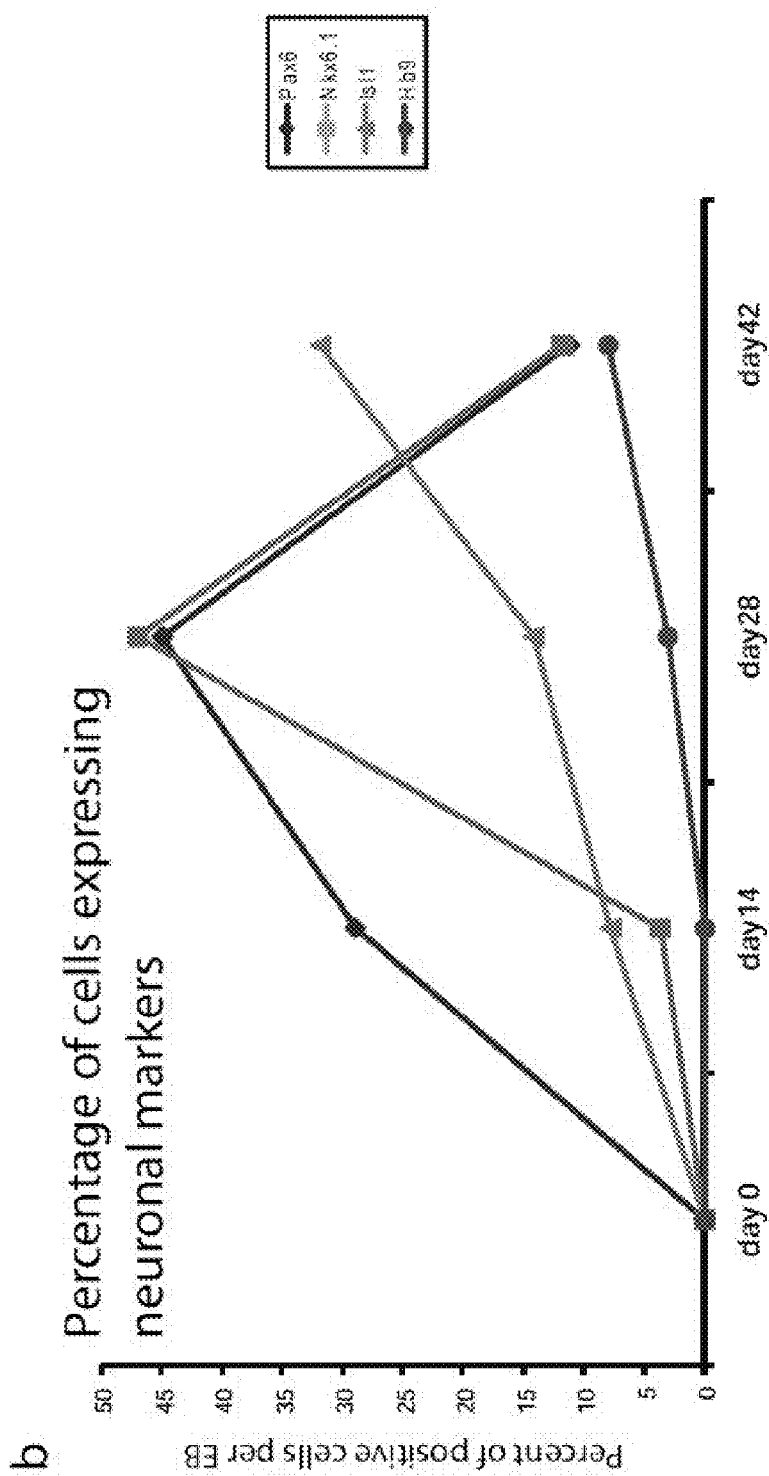

To generate a large supply of motor neurons from human ES cells for the study of ALS we adapted a recently reported method for the production of these cells within embryoid bodies (EBs) (Singh Roy, N. et al. Enhancer-specified GFP-based FACS purification of human spinal motor neurons from embryonic stem cells. *Exp Neurol*. December; 196(2):224-34, 2005) (FIG. 8A). Undifferentiated, self-renewing HuES 3 ES cells (Cowan, C. A. et al. Derivation of embryonic stem-cell lines from human blastocysts. *N Engl J. Med*. March 25; (13):1353-6, 2004) were dissociated into small clumps using collagenase treatment and then allowed to spontaneously differentiate in suspension for 14 days (FIG. 8A). Staining of the resulting EBs with the neuronal progenitor marker PAX6 (data not shown) demonstrated that a substantial percentage (29%+/−16%, FIG. 12a, b) contained cells differentiating down the neuronal lineage. To direct these progenitors towards an anterior and ventral motor neuron identity, we cultured the EBs another 14 days in the presence of retinoic acid (RA) and a small molecule agonist of the sonic hedgehog (SHH) pathway. Under the influence of these morphogens the population of PAX6 positive progenitors expanded (45%+/−15%; FIG. 1b; FIG. 12a, b) and expression of the ventral progenitor markers NKX6.1 and ISL1/2 was induced (FIGS. 12A and 12B). To promote motor neuron differentiation and survival, we then transferred these 28 day-old EBs to media containing neurotrophic factors for a final 14 days. After 42 days of differentiation, the number of progenitors expressing PAX6 and NKX6.1 had begun to decline (FIGS. 12A and 12B), while the number of cells expressing Isl1/2 continued to increase (FIGS. 12A and 12B). In addition, expression of the HB9 transcription factor, which is expressed in maturing post-mitotic motor neurons, was detected in 8% of all cells (FIGS. 12A and 12B). Furthermore, when plated on laminin, these EBs elaborated impressive neuronal processes (FIG. 8).

To further characterize the putative motor neurons contained within these EBs, the 42 day-old EBs were dissociated with papain and the resulting cells plated directly onto glial mono layers prepared from the cortex of neonatal mice (data not shown). We found, as had been previously reported with neurons derived from mouse ES cells (Song, H. et al. Astroglia induce neurogenesis from adult neural stem cells. Nature. May 2; 417(6884):39-44, 2002) that culturing human ES cell derived neurons on a glial monolayer promoted their survival (data not shown). Co-staining of cells with antibodies specific to a neuronal form of tubulin (Tuj1) and the transcription factors Hb9 and Isl1/2 (data not shown), as well as co-staining for Hb9 and choline acetyl transferase (Chat) (data not shown) confirmed that many neurons isolated from these EBs were differentiating towards a motor neuron identity.

To ensure that the appearance of motor neurons within these EBs was dependent on the influences of RA and SHH, we repeated our differentiation scheme in the absence of one or both of these morphogens and counted the number of HB9 positive cells (FIG. 8B). When SHH or RA activity were removed individually, the frequency of cells expressing HB9 fell to 0.7% (+/−0.2) and 1.1% (+/−0.5%) respectively. If both signaling molecules were omitted, less than 0.2% of the dissociated cells expressed HB9 (0.17%+/−0.07%). We further confirmed the robustness of our approach for generating motor neurons by differentiating six independent human ES cells lines and then quantifying the number of HB9 positive cells within the resulting EBs (FIG. 8C). We found that HuES1, HuES3, HuES5 and HuES9 ES cell lines all differentiated with a similar efficiency (HuES 1: 7.1%+/−1.8%; HuES 3: 8.5%+/−0.5%; HuES 5: 4.7%+/−0.8%; HuES 9: 7.7%+/−1.5%), while HuES 12 cells differentiated at a lower efficiency (2.8%+/−1.3%) and HuES13 cells at a higher efficiency 13.9% (+/−3.8%). These results are consistent with a recent report that suggests independent human ES cell lines can have varying abilities to differentiate into certain cell types (Osafune, K. et al. Marked differences in differentiation propensity among human embryonic stem cell lines. *Nat. Biotechnol.* March; 26(3):313-5, 2008).

Figure 9:
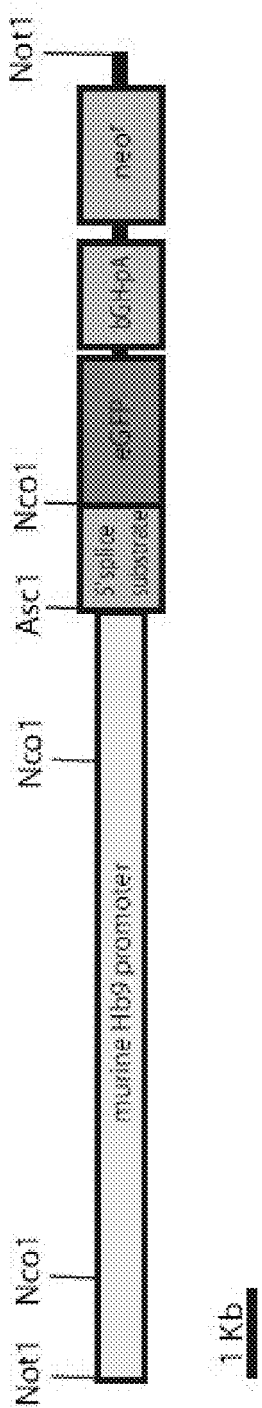
FIG. 9 shows characterization of the Hb9::GFP human ES cell line. DNA construct used for the electroporation of human ES cells.
Figure 13:
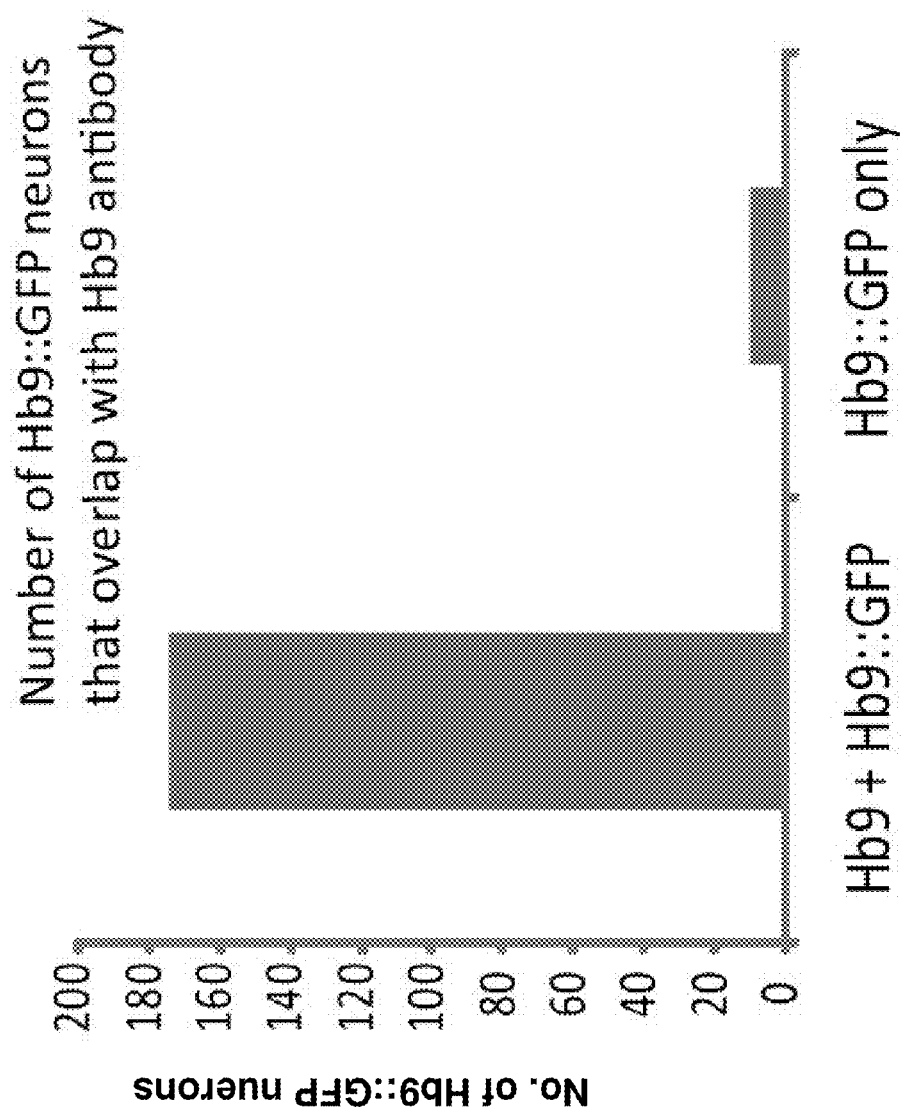
FIG. 13 shows characterization of a Hb9::GFP human ES cell line. Number of Hb9::GFP cells that are immunoreactive to Hb9 antibody (Hb9+Hb9::GFP).

In order to identify living motor neurons in cultures of differentiating human ES cells, we generated a stable transgenic human ES cell line in which sequences coding for the green fluorescent protein (GFP) were under the control of the murine Hb9 promoter (Wichterle et al., 2002) (FIG. 9). To validate that this transgenic cell line accurately reported HB9 expression, we differentiated the cells, plated them on glial monolayers and co-stained with antibodies specific to GFP and HB9. HB9 expression was observed in 95% of GFP positive cells (FIG. 13). We next investigated whether these GFP positive cells expressed other markers that would be consistent with a maturing motor neuron identity (FIG. 13). We observed considerable overlap between GFP and expression of NKX6.1 (data not shown) but no co-expression with NKX2.2 (data not shown), confirming that GFP positive cells had acquired the correct dorsal-ventral identity (Jessell T M. Neuronal specification in the spinal cord: inductive signals and transcriptional codes. *Nat Rev Genet*. October; 1(1):20-9, 2000). Additionally these cells expressed ISL1/2 (data not shown) and ChAT (data not shown) but no longer expressed the progenitor marker PAX6 (data not shown). Antibody co-staining experiments also demonstrated that GFP positive cells did not co-express makers found in other neuronal subtypes such as the interneuron markers CHX10 (data not shown) and LHX2 (data not shown).

Figure 10:
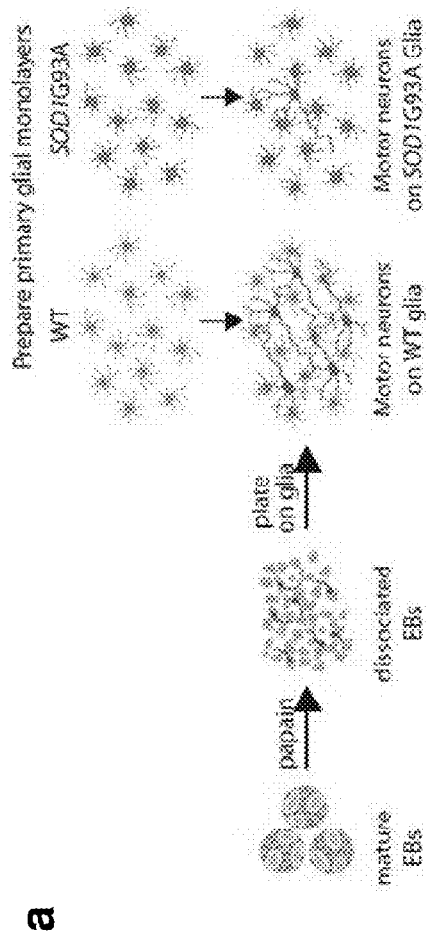
FIG. 10 shows the effect of glial cells over expressing SOD1G93A on human ES cell-derived motor neurons.
Figure 10:
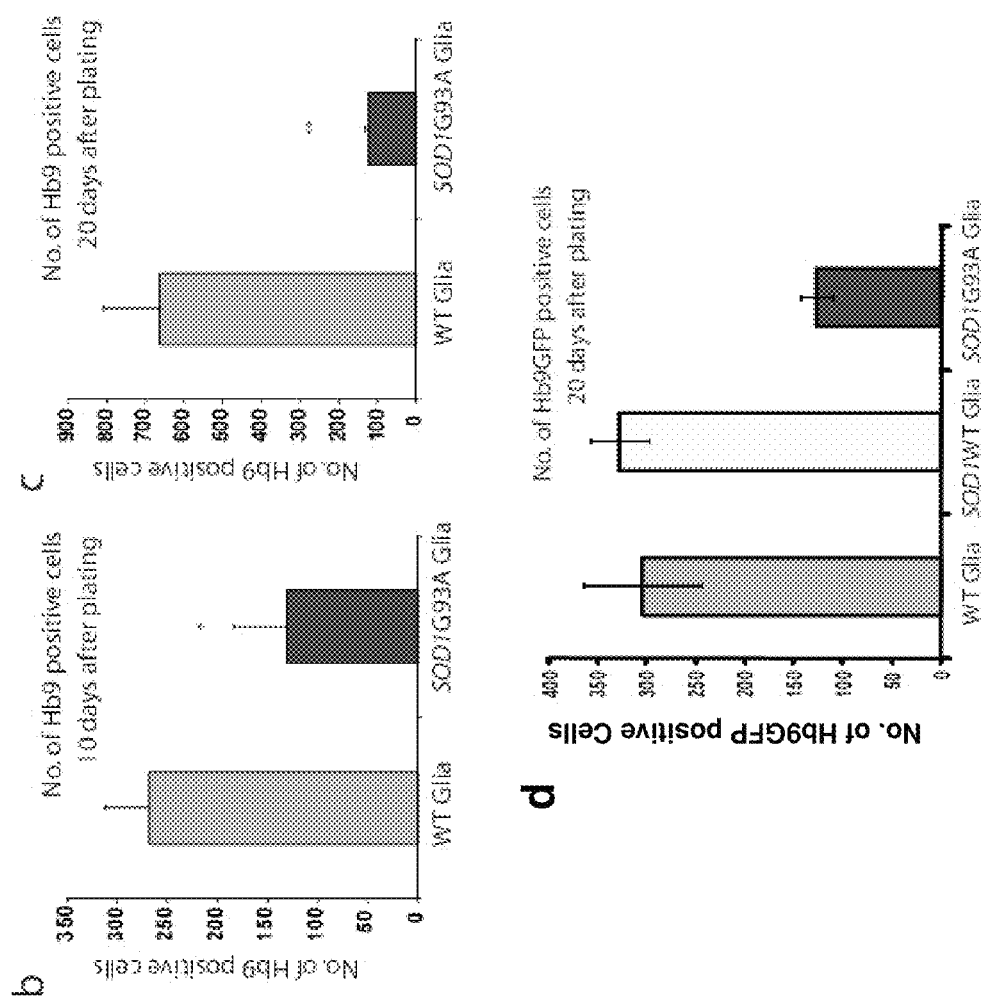

The results that we have described thus far confirm that it is possible to reproducibly generate a large supply of human motor neurons from embryonic stem cells. We next sought to use these human neurons to ask whether they, like their mouse counterparts, are sensitive to the non-cell autonomous effect of glial cells overexpressing a mutant SOD1 gene product. To this end, we dissociated 42 day-old EBs and plated the resulting cells on primary glial monolayers derived from either SOD1G93A transgenic or control mice (FIG. 10A). After 10 days a significant difference (p<0.05) in the number of HB9 positive motor neurons was seen between the two culture conditions (FIG. 10B) is already appreciable. In cultures containing SOD1G93A glia less than half as many motor neurons remained (131+/−53) as in cultures containing non-transgenic control glia (269+/−44) (FIG. 10B). The deficit in motor neuron survival in co-cultures with SOD1G93A glia became even more pronounced after 20 days (FIG. 10C). We next sought to confirm that the toxic effect of glia we observed in our initial experiments was due to the action of the mutant SOD1 protein rather than mere SOD1 protein over-expression. Motor neuron preparations were generated from the Hb9::GFP human ES cell line and co-cultured for 20 days with non-transgenic glia or glia which either over-expressed the wild-type human SOD1 protein or the mutant SOD1G93A protein (data not shown; FIG. 10D). There was no discernable difference between the number of GFP positive motor neurons present in culture with the non-transgenic Glia (304+/−60; data not shown; FIG. 10D) or with glia over-expressing the wild type SOD1 protein (328+/−30; data not shown; FIG. 10D). In contrast, there was a highly significant reduction (p<0.01) in the number GFP positive motor neurons (127+/−16; FIG. 10D) present in culture with the SOD1G93A Glia, confirming that the non-cell autonomous effect of glia was mediated through the mutant SOD1 protein.

In both patients and mice carrying mutant alleles of the SOD1 gene, intracellular aggregation of the SOD1 protein is often documented and has been associated with motor neuron death (Boillee et al., 2006). We therefore wondered whether the toxic effect of glial cells expressing the mutant SOD1 protein that we observed was a downstream consequence of protein aggregation. To address this, we separately cultured primary mouse glia and mouse ES cell derived motor neurons carrying the same SOD1G93A transgene and stained the cultures with antibodies specific for the human SOD1 protein. After 21 days in culture, the SOD1 protein in mouse motor neurons was observed to aggregate into cytoplasmic and perinuclear inclusions (data not shown) (Di Giorgio, F. P., Carrasco, M. A., Siao, M. C., Maniatis, T. & Eggan, K. Non-cell autonomous effect of glia on motor neurons in an embryonic stem cell-based ALS model. *Nat. Neurosci.* 10, 608-614, 2007). In contrast, even after more than 90 days in culture, the SOD1 protein was found to be broadly and diffusely localized in the cytoplasm of all glial cells (data not shown), suggesting that the mutant protein is mediating its effect in these cells through a mechanism independent of protein aggregation.

Figure 11:
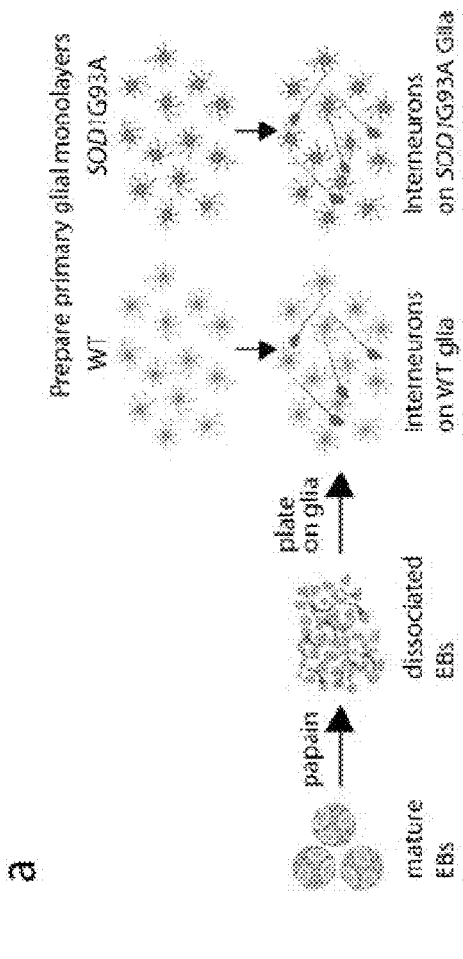
FIG. 11 shows the specificity of the toxic effect of glia overexpressing SOD1G93A on motor neurons.
Figure 11:
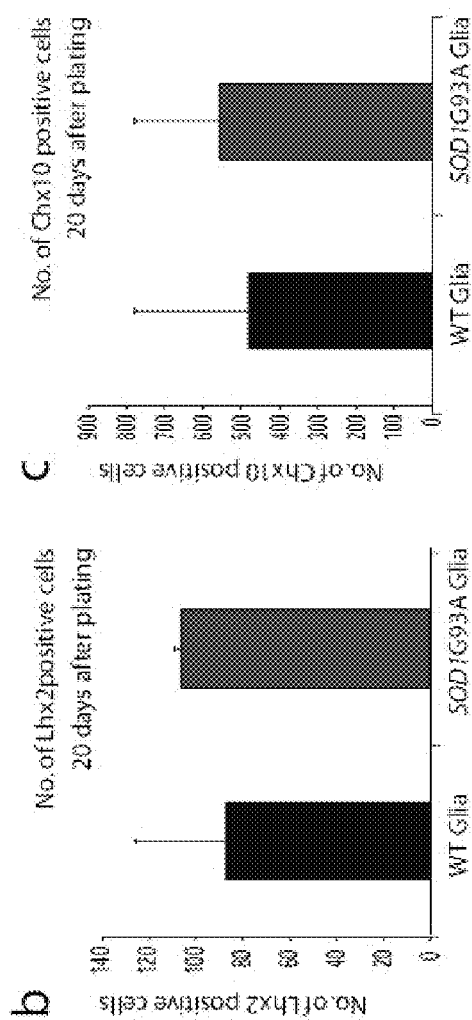
Figure 11:
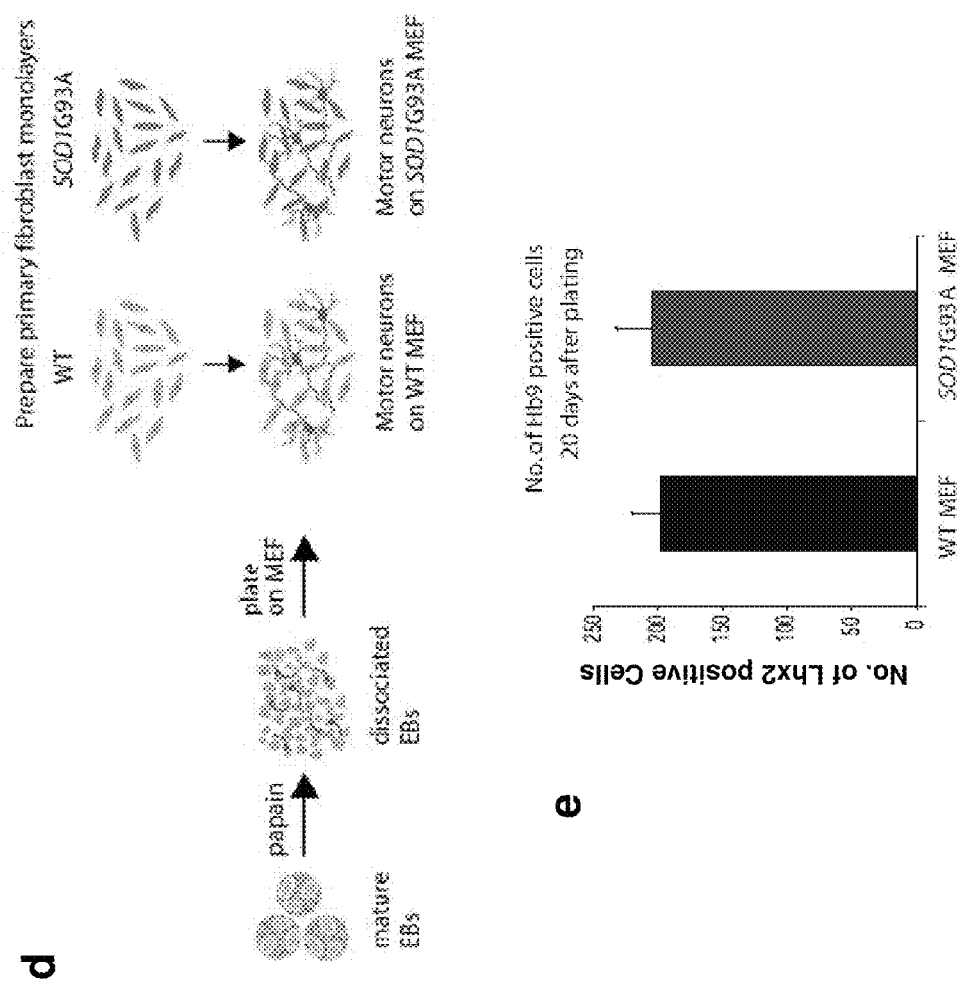

ALS leads to the specific degeneration of motor neurons. Therefore, if the toxic effect of glial cells that we have observed is relevant to ALS then we might expect that other spinal cord neuronal types such as interneurons would not be sensitive to it. During our characterization of human ES cell derived motor neurons we noted that additional neurons expressing the transcription factors CHX10 and LHX2, indicative of V2 and D1 interneuron differentiation, were also produced (data not shown). To test whether these neuronal types were affected by co-culture with mutant glia, we dissociated 42 day-old EBs, plated equal numbers of cells on either SOD1G93A glia or non-transgenic glia (FIGS. 11A-D) and after 20 days of culture stained for Tuj1 and either LHX2 (FIG. 3) or CHX10 (FIG. 11D). We found that neurons expressing either of these interneuron markers were unaffected by culture with mutant glia (FIG. 11B-C), in striking contrast to the sensitivity of motor neurons to this culture environment.

To determine if the toxic effect of mutant glial cells was the consequence of a specific activity within this cell type rather then a general property of any cell over expressing the SOD1G93A mutation, we plated motor neuron preparations on mouse embryonic fibroblasts (MEFs) prepared from SOD1G93A and non-transgenic sibling embryos (data not shown). After 20 days of co-culture we did not observe a significant difference between the number of HhB9, Ttuj1 double positive motor neurons present on SOD1G93A MEFs (204+/−28) or non-transgenic MEFs (197+/−23) (data not shown), consistent with the hypothesis that astrocytes are specifically responsible for the non-cell autonomous effect we observed (Di Giorgio et al., 2007; Nagai et al., 2007).

Example 8

Methods

Example 7 was performed using the following methods:
Growth of human Embryonic Stem Cells.

The HuES cell lines were obtained from Doug Melton and cultured as described by Cowan et al. (Cowan et al., 2004). The hESCs were maintained on a feeder layer of inactivated mouse embryonic fibroblasts (GlobalStem) in human ES cell media (KO-DMEM (Gibco), 10% KO Serum Replacement, 10,000 units Penicillin and 1 mg/ml Streptomicin (GIBCO), 2 mM Glutamine (GIBCO), 100 µM non-essential amino acids (GIBCO), 55 µM beta-mercapto-ethanol (GIBCO), 10% Plasmanate (Bayer), 10 ng/mL bFGF2 (GIBCO)). The cells were cultured at 37° C. and 5% $CO_2$. Media was replaced daily for the duration of hESC expansion and the cells in these conditions were passaged every 5-7 days using a solution with 0.05% trypsin (GIBCO).

Differentiation of human Embryonic Stem Cells into motor neurons. For differentiation into motor neurons, the cells were allowed to reach 80-90% confluency, washed once with PBS, and then incubated for 15 minutes at 37° C. in a solution of 1 g/L Collagenase IV (GIBCO) in DMEM-F12 (GIBCO).

Using a cell scraper, the ES cell colonies were scraped and washed off the plate, centrifuged for 5 minutes at 1000 RPM and resuspended in human ES cell media without bFGF2 or plasmanate in low attachment 6-well plates.

After 24 hours, the cells had aggregated to form embryoid bodies (EBs), and the media was changed to remove debris by centrifuging the EBs and resuspending in fresh in human ES cell media without bFGF2 or plasmanate in low attachment 6-well plates. EBs were cultured as such for 13 more days, with half of the media changed every two days, and a complete media change every week. After 14 days, the EBs were induced toward a caudal and ventral identity using retinoic acid (1 µM, Sigma) and an agonist of the Shh signaling pathway (1 µM) in N2 media: 1:1 DMEM:F-12+Glutamate (Gibco), 10,000 units Penicillin and 1 mg/mL Streptomicin (Gibco), 1% N2 Supplement (Gibco), 0.2 mM ascorbic acid (Sigma-Aldrich), 0.16% D-(+)-Glucose (Sigma-Aldrich), BDNF (10 ng/ml, R&D Systems), for another 14 days. The EBs were then matured for a final 14 days in N2 media with GNDF (10 ng/mL, R&D Systems). After 42 days of differentiation, the EBs were dissociated. To dissociate the EBs, they were centrifuged at 1000 rpm for 5 min in a 15 ml falcon tube, and then washed once with PBS to eliminate residual media. The EBs were then incubated for 60 minutes at 37° C. in Earle's Balanced Salt Solution with 20 units of papain and 1000 units of Deoxyribonuclease I (Worthington Biochemical Corporation). EBs were triturated using a 2 mL serological pipette every 15-20 minutes during this incubation. When an almost single cell suspension was achieved, the cells were centrifuged for 5 minutes at 1000 RPM. The resulting cell pellet was washed once with PBS and then resuspended in N2 media with neurotrophic factors (GDNF, and BDNF (10 ng/ml, R&D Systems)). These cells were then counted and plated on Poly-D-Lysine/Laminin CultureSlides (BD biosciences) or on a layer of primary glial cells. Depending on the experiment, motor neurons or interneurons were counted 10 or 20 days after plating.

Generation of the HuES 3 Hb9::GFP cell line. To generate the Hb9::GFP HuES 3 cell line, HuES 3 cells were electroporated with a plasmid containing a neomycin resistance cassette and the coding sequence of Green Fluorescent Protein under transcriptional control of a 9 kb murine Hb9 promoter restriction fragment. The plasmid was a kind gift of Hynek Witcherle (Columbia University) and was a modification of the construct described in Witcherle et al. (2002). The elctroporation was performed as described in Zwaka P T. et al. (Zwaka T P, Thomson J A. Homologous recombination in human embryonic stem cells. *Nat. Biotechnol*. March; 21(3): 319-21, 2003).

Undifferentiated HuES 3 cells were grown as described below. Once the cells reached 80-90% confluency, they were dissociated in trypsin and counted. Approximately $1.0 \times 10^7$ were resuspended in 0.7 mL of human ES cell media and mixed with 0.1 mL of the same media containing 30 µg of linearized vector. This mix of cells and DNA was then transferred to a 0.4 cm cuvette and exposed to a pulse of 320 V, 200 µF at room temperature. After 10 minutes at room temperature the cells were plated on a 10 cm dish of MEF, and 48 hours after electroporation the cells were switched to media containing G418 (50 µg/mL, GIBCO). Selection media was changed daily for 14 days, after which we picked and expanded 24 resistant human ES cell colonies. In order to assay GFP expression, we differentiated six of these resistant clones into motor neurons and immunostained for GFP and HB9 co-expression. Two of these clones gave rise GFP positive cells that elongate green axons, however only one clone was validated by immunoreactivity to the Hb9 antibody and used in subsequent experiments.

Immunocytochemistry Analysis.

Cells were fixed with 4% para-formaldehyde for 30 minutes at room temperature. After fixation, the cells were washed 3 times with PBS for 10 minutes and then treated for 1 hour in a blocking solution (PBS (Cellgro), donkey serum (10%, Jackson Immunoresearch)) plus Triton X (0.1%, Sigma) for permeabilization. After blocking, the cells were incubated overnight at 4° C. with primary antibodies: mouse anti-beta tubulin III (Covance); rabbit anti-beta tubulin III (SIGMA); Pax6, Nkx6.1, Nkx2.2, Isl 1, Hb9 (DSHB); Chx10, Lhx2 (Santa Cruz Technologies); ChAT (Chemicon); rabbit anti-GFP conjugated Alexa fluor 488 (Molecular Probes); in the blocking solution. After the overnight incubation the cells were washed 3 times in PBS for 10 minutes. Localization of antigens was visualized by incubating for 1 hour at room temperature using the respective secondary antibodies (Alexa fluor 594 or 488; Molecular Probes). Finally, the samples were washed again in PBS 3 times and mounted using a solution with or without DAPI. Images were taken using a fluorescent Olympus IX70 microscope.

Primary Glial Cultures.

P1-P3 mouse pups transgenic for SOD1G93A, SOD1WT or non-transgenic pups were sacrificed by using an approved method of euthanasia. Under a dissection microscope, the parenquima were isolated and the meninges were carefully stripped away with fine forceps. The tissue was then dissected into small pieces and transferred to a solution containing 12 ml of HBSS, 1.5 ml of trypsin (GIBCO) and 1% DNAse (Sigma) and incubated at 37° C. for 15 min, swirling the mixture periodically. The supernatant containing the dissociated cells was then collected and 3 ml of serum was added to inhibit trypsin activity.

The cells were then centrifuged at 1000 rpm for 5 min, resuspended in Glia medium: (Minimun Essential Medium with Earl's salts (GIBCO), D-(+)-Glucose 20% (Sigma), Penicillin-streptomycin (GIBCO), 10% Horse Serum (GIBCO)) and plated at the concentration of 80,000 cells per mL in T75 flasks (Falcon). After the glia reached confluency, they were replated onto Poly-D-Lysine/Laminin CultureSlides (BD biosciences).

Data analysis. Statistical analysis was performed using Student's t-Test and are expressed as arithmetic mean±S.D.; t-test values of * P<0.05, ** P<0.01, were considered statistically significant.

Example 9

Identification of Candidate Genes Involved in SOD1G93A Glial Toxicity

To better understand how the expression of a mutant gene that causes ALS can perturb the normal phenotype of astrocytes, and to identify genes that may have a role in their toxic effect on motor neurons, we used oligonucleotide arrays to compare the global gene expression profiles of glia overexpressing the mutant SOD1G93A protein with two different sets of controls: non-transgenic glia and glia overexpressing the wild type form of the human SOD1 protein.

Figure 14:
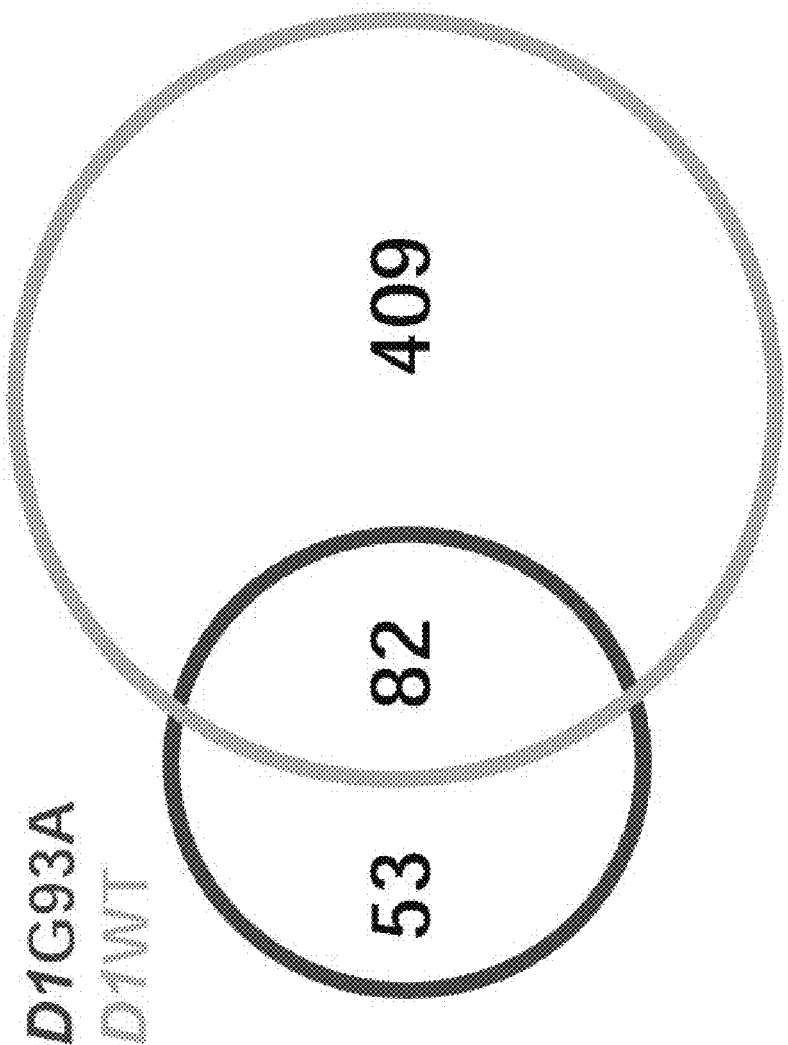
FIG. 14A is a Venn Diagram presenting the overlap among transcripts selectively over expressed in SOD1G93A glia and in SOD1WT glia with respect to WT glia.
FIG. 14B is a table listing a subset of genes over expressed in SOD1G93A glia but not in SOD1WT glia or WT glia.
FIG. 14C is a graph showing the percentage of Hb9::GFP cells remaining on non-transgenic (WT) glia after 20 days of treatment with GMFb, Rantes, Cxcl 7, Mcp 2, Shh or PGD2 compared to the untreated condition (Ctrl) (n=3).
FIG. 14D is a graph showing the percentage of Hb9::GFP cells remaining on WT glia or SOD1G93A glia after 20 days of treatment with the inhibitor of Prostaglandin D2 receptor, a DP1 antagonist MK 0524 (n=3).
FIG. 14E is a graph showing the percentage of Hb9::GFP cells remaining on WT glia or SOD1G93A glia after 10 days of treatment with the inhibitor of Prostaglandin D2 receptor, a DP2 antagonist BAY-u3405.
FIG. 14F is a graph showing the percentage of Hb9::GFP cells remaining on WT glia or SOD1G93A glia after 10 days of treatment with the inhibitor of Prostaglandin D2 receptor, a DP1 antagonist BW868C.
Figure 14:
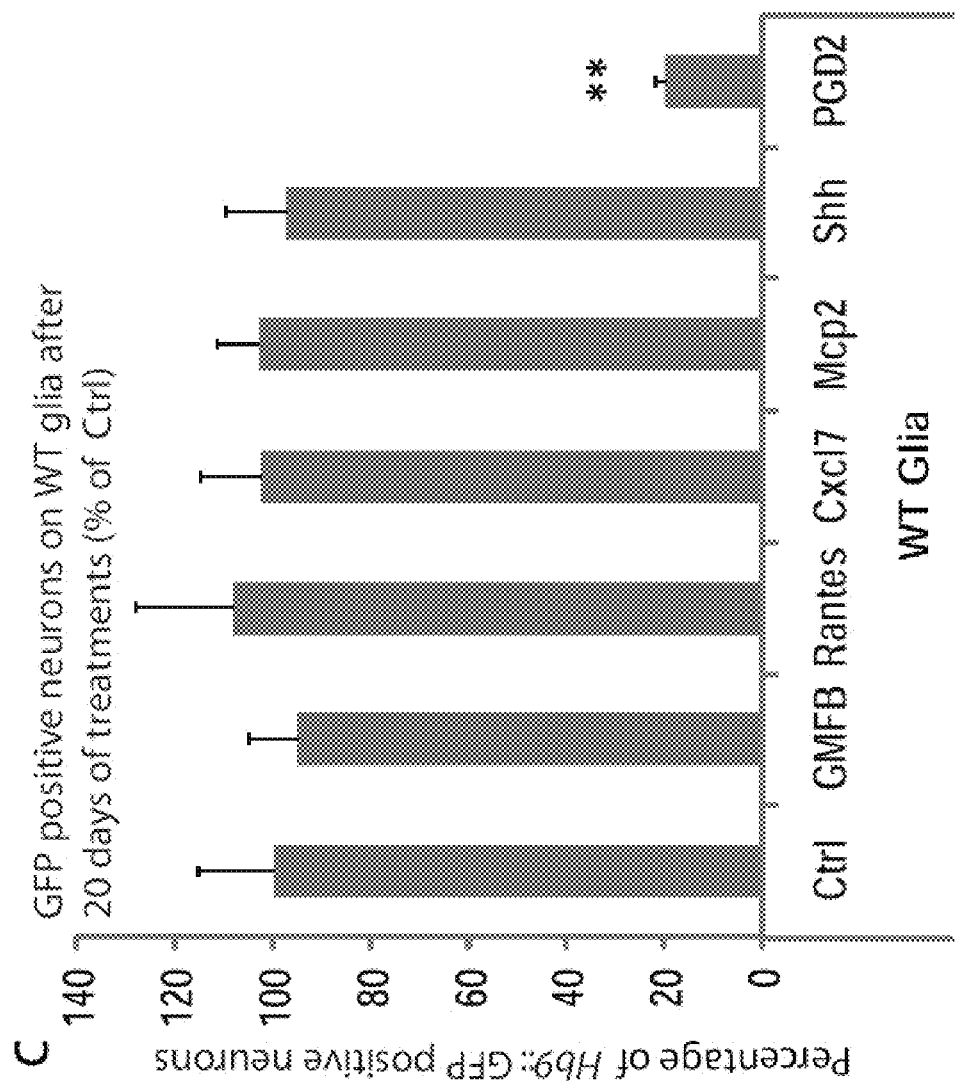
Figure 14:
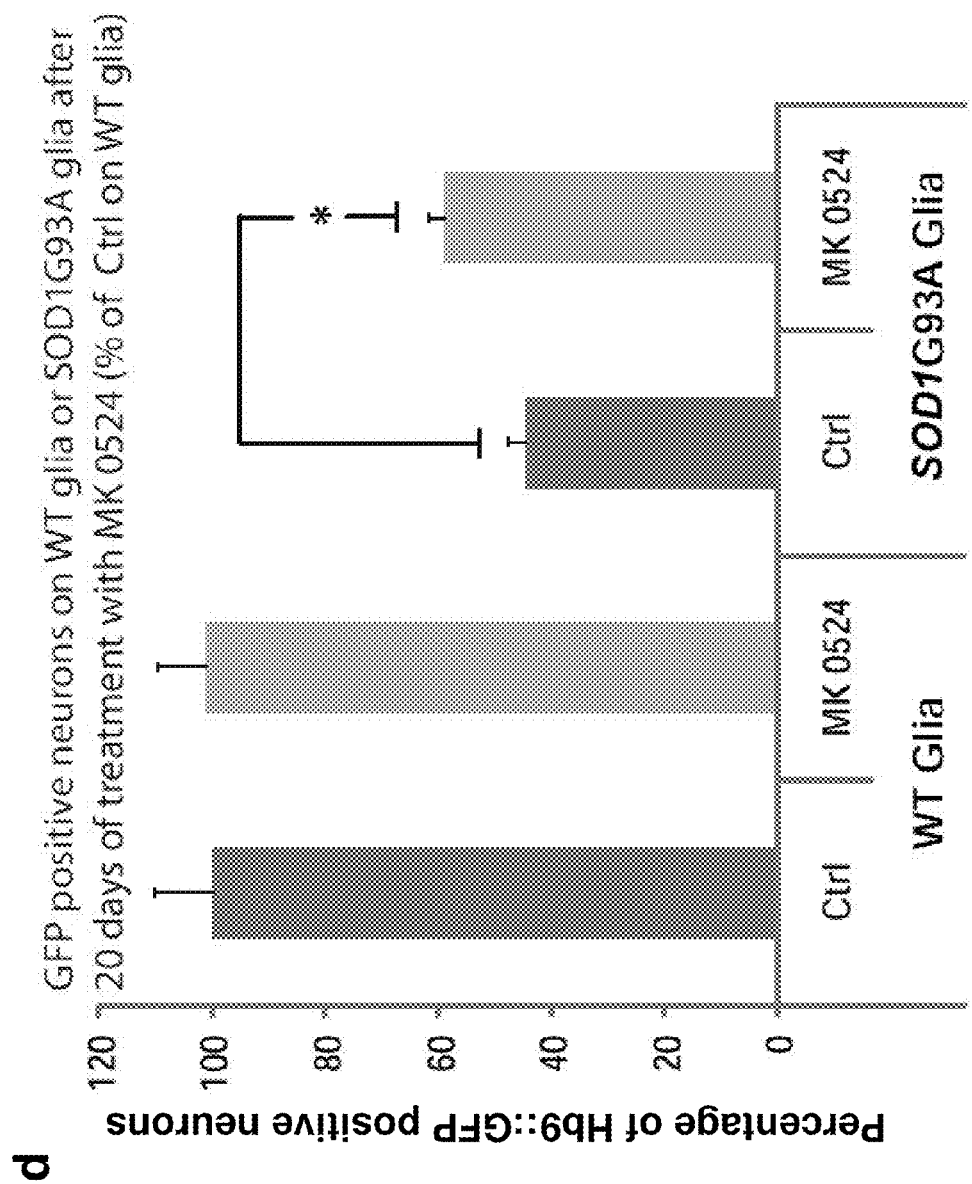
Figure 14:
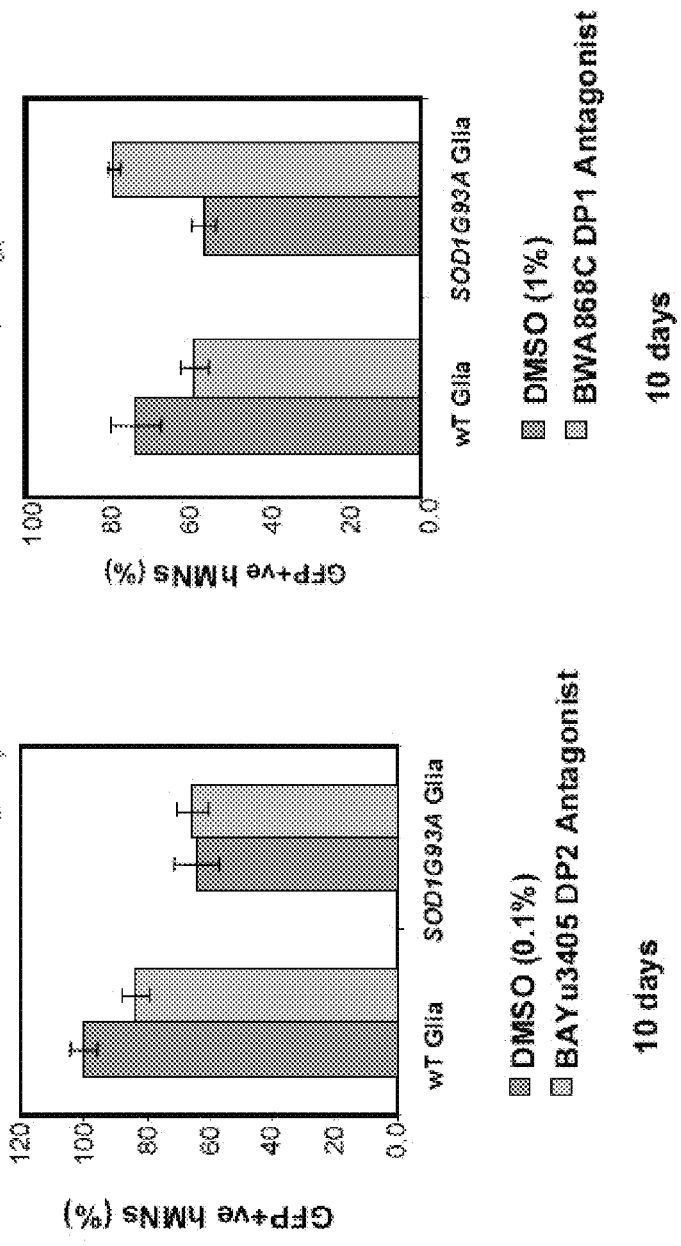

We identified 135 genes whose expression was significantly (P<0.001) increased more than 2 fold in SOD1G93A glia when compared to non-transgenic glia. Of these 135 genes, 53 genes were exclusively up-regulated in the mutant glia, and not in glia over-expressing the wt SOD1 protein (FIG. 14A). We found that 13 of these 53 genes (24%) have previously been identified to have a role either in inflammatory or immune processes. Genes overexpressed more than 2 fold (P<0.001) in SOD1G93A glia with respect to WT glia and SOD1 WT glia are listed in Table 2. We narrowed our analysis to a subset of these genes deemed to be of particular interest because of their known role as pro-inflammatory factors and their substantially increased expression in mutant glia (FIG. 14B). The prostaglandin D2 (PGD2) receptor was up-regulated more than 14 fold in SOD1G93A glia compared to the control sample. Three different cytokines were also shown to be over expressed in mutant glia: Mcp2, Cxcl7, and Rantes. Also found to be highly (>13 fold) up-regulated in these microarrays, was the gene encoding glial maturation factor beta (GMFb), which has been shown to induce a pro-inflammatory state in astrocytes (Zaheer et al., J. Neurochem. 101:364-376, 2007). Finally, we found that the expression of SHH and the SHH responsive genes NKX2.2 and DBX2 was modestly increased in the mutant glia, suggesting that this signaling pathway might be activated in response to the actions of the mutant SOD1 protein.

Microarray Analysis.

Glia were derived from P1-P3 mouse pups as described above. Once the cells reached confluence, total RNA was isolated using Trizol (Invitrogen) from three different biological replicates for each type of glia. RNA was amplified by one round of T7 transcription using the Illumina TotalPrep RNA Amplification Kit. Illumina Bead Array Reader. Analysis was done using the Illumina Bead Studio Program.

Data Analysis.

Statistical analysis was performed using Student's t-Test and are expressed as arithmetic mean±S.D.; t-test values of * P<0.05, ** P<0.01, were considered statistically significant.

TABLE 2

Genes overexpressed in SOD1G93A mutant glia

| SYMBOL | SEARCH_KEY | Fold diff. G93A vs N.T | Gene function |
| --- | --- | --- | --- |
| Serpina1b | NM_009244.2 | 17.64285714 | protease |
| Ptpn7 | scl0320139.8_83 | 15.5 | signaling/immuno response |
| Zc3hdc1 | NM_172893.1 | 14.61111111 | unknown |
| Ptgdr | NM_008962.2 | 14.125 | inflammation |
| Gmfb | NM_022023.1 | 13.07692308 | inflammation |
| Abca5 | NM_147219.1 | 11.45454545 | signaling |
| Dbx2 | scl0223843.1_155 | 11.35714286 | transcription factor |
| Rab6b | scl0270192.9_201 | 6.363157895 | signaling |
| Cutl1 | scl013047.4_12 | 5.4 | transcription factor |
| Ada | NM_007398.2 | 4.962962963 | metabolic |
| Ncoa6ip | NM_054089.2 | 4.654545455 | unknown |
| Ifi35 | scl40880.4.1_8 | 4.369047619 | inflammation |
| Rabl2a | NM_026817.1 | 4.081081081 | unknown |
| Al481214 | scl0004149.1_262 | 3.84 | unknown |
| Cygb | NM_030206.1 | 3.833333333 | transport |
| Dfy | NM_010045.1 | 3.305084746 | inflammation |
| Chodl | scl48930.7.1_272 | 3.186440678 | structural |
| Nrxn1 | scl0001711.1_8 | 3.178723404 | signaling |
| Defb11 | NM_139221.1 | 3.164556962 | immuno response |
| Rusc2 | scl25518.12_3 | 3.086787565 | unknown |
| Nrxn1 | scl0001711.1_8 | 3.023584906 | signaling |
| Matn4 | NM_013592.2 | 3.006147541 | structural |
| Xlr3a | NM_011726.1 | 2.837696335 | unknown |
| Ccl8 | NM_021443.1 | 2.776623377 | inflammation |
| Timd4 | scl41638.9.1_29 | 2.760869565 | immuno response |
| Osr2 | scl47995.5.83_129 | 2.738461538 | transcription factor |
| 9130213B05Rik | scl27589.4_81 | 2.6 | unknown |
| Reck | scl053614.23_117 | 2.594262295 | signaling |
| Olfr116 | NM_146632.1 | 2.574712644 | unknown |
| A230098A12Rik | scl36723.20_445 | 2.505050505 | unknown |
| Shh | scl28000.7.1_29 | 2.475247525 | signaling |
| Fpr1 | scl50268.2.1_13 | 2.447058824 | inflammation |
| Cxcl7 | NM_023785.1 | 2.43324937 | inflammation |
| Dnajb3 | scl16502.1.45_71 | 2.429906542 | structural |
| Defb10 | NM_139225.1 | 2.348387097 | immuno response |
| Apoa2 | NM_013474.1 | 2.335526316 | metabolic |
| Col1a2 | scl012843.30_10 | 2.326599327 | structural |
| 1700030B17Rik | scl16712.12_256 | 2.319796954 | unknown |

TABLE 2-continued

Genes overexpressed in SOD1G93A mutant glia

| SYMBOL | SEARCH_KEY | Fold diff. G93A vs N.T | Gene function |
| --- | --- | --- | --- |
| Atp9a | scl18294.24.1__12 | 2.317307692 | metabolic |
| Ccl5 | NM_013653.1 | 2.299539171 | inflammation |
| Slc39a14 | scl00213053.1__19 | 2.288590604 | transporter |
| Saa3 | scl31343.5.1__35 | 2.25437788 | inflammation |
| 3632451O06Rik | scl45626.8__445 | 2.203812317 | unknown |
| Atrnl1 | scl0226255.12__147 | 2.14556962 | unknown |
| Alms1 | scl29818.18.1__0 | 2.137614679 | unknown |
| Nkx2-2 | scl18553.4.1__4 | 2.112612613 | transcription factor |
| Prss19 | NM_008940.1 | 2.076923077 | signaling |
| Hist1h4k | NM_178211.1 | 2.038550501 | unknown |
| Ephb2 | scl0013844.2__257 | 2.017094017 | receptor |
| Syt12 | NM_134164.2 | 2.016666667 | signaling |
| Foxq1 | NM_008239.3 | 2.016666667 | transcription factor |
| Sfrs16 | scl31678.22.1__32 | 2.01518785 | unknown |
| Lancl1 | NM_021295.1 | 2.010822511 | immuno response |
| Mlp | scl0017357.2__67 | 2.010471204 | signaling |

Example 10

Human ES Cell Derived Motor Neurons can be Used to Identify Neurotoxic Factors

In order to investigate the possible involvement of candidate factors and signaling pathways in the glial mediated neurotoxicity we have observed, we tested the effect of these candidate gene products, or molecules that activate them, on motor neuron survival in co-cultures with wild type glial cells. Non-transgenic glia were individually pretreated for 1 day with either one of the three cytokines MCP2, Cxcl7, or Rantes; with GMFb; an agonist of SHH pathway; or with PGD2. Glia were pretreated for 1 day with either MCP2 (100 ng/ml; Peprotech), Cxcl7 (100 ng/ml; Peprotech), Rantes (100 ng/ml; Peprotech), GMFb (250 ng/ml; Peprotech), an agonist of Shh pathway (1 µM), PGD2 (10 µM; Chayman Chemical) or MK 0524 (10 µM; Chayman Chemical). After the pretreatment for 24 hours, a cellular preparation containing Hb9::GFP human ES cell-derived motor neurons, dissociated from EBs, was added to the glia at the concentration of 30,000 cells/well. Replicate cultures were individually maintained for 20 days in the presence of each of the 6 factors, fixed, and the numbers of GFP positive motor neurons quantified.

We found that treatment with GMFb did not significantly affect the number of human ES cell derived motor neurons compared to the control condition (95%+/−9%). Likewise, the presence of any one of the three cytokines (Rantes, Cxcl7 and Mcp2), or the SHH agonist, did not seem to negatively affect the number of GFP positive motor neurons (respectively 108%+/−20%; 102%+/−12%; 103%+/−8%; 97%+/−12%) (FIG. 20C). However, when the cells were treated for 20 days with PGD2, we found a dramatic decrease in the number of motor neurons compared to the control condition (19%+/−2%; p<0.01) (FIG. 14C), suggesting that prostaglandin D2 signaling contributes to motor neuron toxicity in this system.

Example 11

Inhibition of the Prostaglandin D2 Receptor Rescues Motor Neuron Loss

To determine if there was a direct relationship between the toxic effect of prostaglandin signaling on motor neurons and the SOD1G93A glial mediated neurotoxicity, we tested whether a specific antagonist of the prostaglandin D2 receptor, MK 0524 (Sturino et al., J. Med. Chem., 50:794-806, 2007), could counteract or ameliorate the toxic effect of mutant glia on motor neurons. SOD1G93A glia and wt glia were pretreated for 1 day with the prostaglandin D2 receptor inhibitor, human motor neurons were added, and cultures were maintained for 20 days both in the presence and absence of the drug. We found that the presence of MK 0524 did not affect motor neuron numbers when they were co-cultured with wildtype glia. (100%+/8%, FIG. 14D). However, when human motor neurons plated on SOD1G93A glia were treated with the inhibitor, there was a statistically significant (p<0.05) increase in the number of GFP positive neurons (32%, relative to untreated neurons plated on the same glia) (FIG. 14D). In a similar experiment using another prostaglandin D2 receptor DP1 specific antagonist BWA868C, BWA868C significantly reduced cell death of motor neurons that were cultured on SOD1G93A glia (FIG. 14F). This protection property was specific for DP1 receptor and not for the DP2 receptor as a DP2 receptor specific antagonist, BAY-u3405, had no effect on promoting survival of motor neurons cultured on SOD1G93A glia (FIG. 14E).

These experiments suggest that inhibitors of PGD2 signaling do not generally act to promote motor neuron survival and instead act to specifically counteract the toxic effects of glial cells carrying the ALS mutation.

The foregoing description is to be understood as being representative only and is not intended to be limiting. Alternative methods and materials for implementing the invention and also additional applications will be apparent to one of skill in the art, and are intended to be included within the accompanying claims

What is claimed is:

1. A method of treating motor neuron disease, the method comprising administering an inhibitor of a prostaglandin D2 DP1 receptor comprising the compound of formula (II)

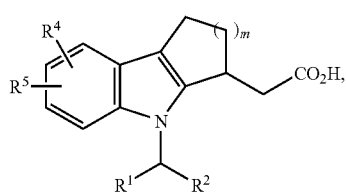

Formula (II)

to a subject in need thereof, wherein the inhibitor inhibits expression or activity the prostaglandin D2 DP1 receptor, wherein the motor neuron disease is amyotrophic lateral sclerosis (ALS), and wherein: $R^1$ is H or $C_1$-$C_6$ alkyl; $R^2$ is aryl or heteroaryl, each of which can be optionally substituted; $R^3$ and $R^4$ are each independently is halo, —$CF_3$, —CN, —$NO_2$, —S(=O)alkyl, —$SO_2$alkyl, $C_1$-$C_6$ alkyl; —C(O)alkyl, —CH(OH)alkyl; and m is 1, 2 or 3.

2. The method of claim 1, wherein the method further comprising selecting a subject diagnosed with motor neuron disease.

3. The method of claim 1, wherein the motor neuron disease is associated with a SOD1 mutation in at least one allele.

4. The method of claim 1, wherein the inhibitor is:

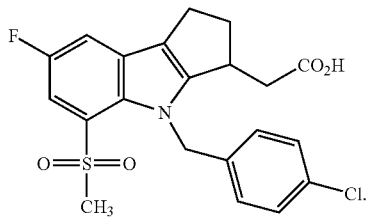

5. The method of claim 1, wherein the inhibitor is:

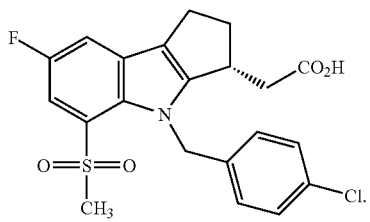

6. A method of treating motor neuron disease associated with a SOD1 mutation in at least one allele, the method comprising administering an inhibitor of a prostaglandin D2 DP1 receptor comprising the compound of formula (II)

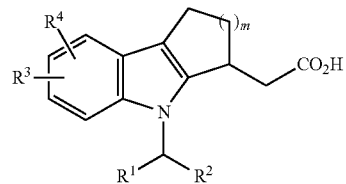

to a subject in need thereof,
wherein:
$R^1$ is H or $C_1$-$C_6$ alkyl;
$R^2$ is aryl or heteroaryl, each of which can be optionally substituted;
$R^3$ and $R^4$ are each independently is halo, —$CF_3$, —CN, —$NO_2$, —$SO_2$alkyl, $C_1$-$C_6$ alkyl; —C(O)alkyl, —CH(OH)alkyl; and
m is 1, 2 or 3.

7. The method of claim 6, wherein the compound is:

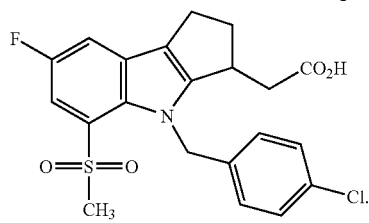

8. The method of claim 7, wherein the compound is:

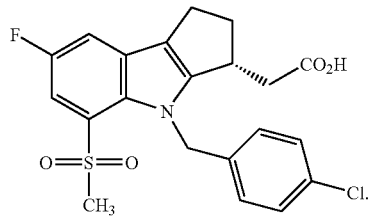 [SMILES: CS(=O)(=O)c1cc(F)cc2c3c(n(Cc4ccc(Cl)cc4)c12)C(CC(=O)O)CC3]

9. The method of claim 6, wherein the method further comprising selecting a subject diagnosed with motor neuron disease.

10. The method of claim 9, wherein the motor neuron disease is selected from a group consisting of amyotrophic lateral sclerosis (ALS), primary lateral sclerosis (PLS), progressive muscular atrophy (PMA), pseudobulbar palsy, progressive bulbar palsy, spinal muscular atrophy (SMA) and post-polio syndrome.

* * * * *

UNITED STATES PATENT AND TRADEMARK OFFICE
CERTIFICATE OF CORRECTION

| | | |
|---|---|---|
| PATENT NO. | : 9,180,114 B2 | Page 1 of 1 |
| APPLICATION NO. | : 12/570476 | |
| DATED | : November 10, 2015 | |
| INVENTOR(S) | : Kevin C. Eggan | |

It is certified that error appears in the above-identified patent and that said Letters Patent is hereby corrected as shown below:

In the Claims:

Column 65, claim 1, line 34, the phrase "is halo" should read "halo".

Column 65, claim 2, line 37, the phrase "wherein the method" should read "the method".

Column 66, claim 6, line 31, the phrase "is halo" should read "halo".

Signed and Sealed this
Third Day of May, 2016

Michelle K. Lee
*Director of the United States Patent and Trademark Office*